(12) United States Patent
Jacobs

(10) Patent No.: US 9,655,849 B2
(45) Date of Patent: May 23, 2017

(54) SOLID PARTICULATE COMPOSITIONS COMPRISING COENZYME Q10

(75) Inventor: Irwin C. Jacobs, St. Louis, MO (US)

(73) Assignee: Particle Dynamics International, LLC, St. Louis, MO (US)

(*) Notice: Subject to any disclaimer, the term of this patent is extended or adjusted under 35 U.S.C. 154(b) by 237 days.

(21) Appl. No.: 14/000,902

(22) PCT Filed: Mar. 16, 2012

(86) PCT No.: PCT/US2012/029358
§ 371 (c)(1),
(2), (4) Date: Aug. 22, 2013

(87) PCT Pub. No.: WO2012/129072
PCT Pub. Date: Sep. 27, 2012

(65) Prior Publication Data
US 2013/0330408 A1 Dec. 12, 2013

Related U.S. Application Data

(60) Provisional application No. 61/454,111, filed on Mar. 18, 2011.

(51) Int. Cl.
*A61K 9/16* (2006.01)
*A61K 31/122* (2006.01)
*A61K 9/107* (2006.01)

(52) U.S. Cl.
CPC .............. *A61K 9/16* (2013.01); *A61K 9/1617* (2013.01); *A61K 9/1652* (2013.01); *A61K 31/122* (2013.01); *A61K 9/107* (2013.01)

(58) Field of Classification Search
CPC ........ A61K 31/122; A61K 9/107; A61K 9/16; A61K 9/1617; A61K 9/1652; E21B 10/22; F03B 13/00; F03B 17/063; F05B 2220/20; F05B 2220/602; F05B 2240/13; F05B 2240/2411; Y02B 10/50; Y02E 10/28

See application file for complete search history.

(56) References Cited

U.S. PATENT DOCUMENTS

| | | |
|---|---|---|
| 5,891,469 A | 4/1999 | Amselem |
| 5,989,583 A | 11/1999 | Amselem |
| 6,056,971 A | 5/2000 | Goldman |
| 6,086,915 A | 7/2000 | Zeligs et al. |
| 6,299,896 B1 | 10/2001 | Cooper et al. |
| 6,300,377 B1 | 10/2001 | Chopra |
| 6,303,139 B1 | 10/2001 | Passi et al. |
| 6,361,800 B1 | 3/2002 | Cooper et al. |
| 6,416,793 B1 | 7/2002 | Zeligs et al. |
| 6,740,338 B1 | 5/2004 | Chopra |
| 6,855,733 B2 | 2/2005 | Udell et al. |
| 6,861,447 B2 | 3/2005 | Moldenhauer et al. |
| 6,953,588 B2 | 10/2005 | Cooper et al. |
| 7,026,361 B2 | 4/2006 | Minemura et al. |
| 7,030,102 B1 | 4/2006 | Madhavi et al. |
| 7,060,263 B2 | 6/2006 | Udell et al. |
| 7,273,622 B2 | 9/2007 | Udell et al. |
| 7,407,670 B2 | 8/2008 | Six et al. |
| 7,438,903 B2 | 10/2008 | Parkhideh |
| 7,645,816 B2 | 1/2010 | Borowy-Borowski et al. |
| 7,708,990 B2 | 5/2010 | Fujii et al. |
| 7,713,523 B2 | 5/2010 | Fantuzzi et al. |
| 7,803,366 B2 | 9/2010 | Parkhideh |
| 7,910,340 B2 | 3/2011 | Yajima et al. |
| 2003/0105168 A1 | 6/2003 | Minemura et al. |
| 2005/0037073 A1 | 2/2005 | Schwarz |
| 2005/0069582 A1 | 3/2005 | Fantuzzi |
| 2006/0018891 A1 | 1/2006 | Udell et al. |
| 2006/0051462 A1 | 3/2006 | Wang |
| 2006/0078609 A1 | 4/2006 | Vandecruys et al. |
| 2006/0275358 A1 | 12/2006 | Lin |
| 2007/0184040 A1 | 8/2007 | Clouatre |
| 2007/0259034 A1 | 11/2007 | Steele et al. |
| 2008/0020022 A1 | 1/2008 | Udell |
| 2008/0089877 A1 | 4/2008 | Udell et al. |
| 2008/0171373 A1 | 7/2008 | Yajima et al. |
| 2008/0254188 A1 | 10/2008 | Borowy-Borowski et al. |
| 2009/0060891 A1 | 3/2009 | Harris et al. |

(Continued)

FOREIGN PATENT DOCUMENTS

| | | |
|---|---|---|
| KR | 20080097072 | 11/2008 |
| WO | 0152822 A1 | 7/2001 |

(Continued)

OTHER PUBLICATIONS

International Search Report, PCT/US2012/029358, dated Sep. 4, 2012, 4 pages.
Written Opinion, PCT/US2012/029358, dated Sep. 4, 2012, 11 pages.
Abstract of KR20080097072; Nov. 4, 2008.
Ullmann et al., "A new Coenzyme Q10 tablet-grade formulation (all-Q) is bioequivalent to Q-Gel and both have better bioavailability properties than Q-SorB", J. Med. Food, 2005 Fall; 8(3):397-9.
Wolters et al., "Plasma ubiquinone status and response to six-month supplementation combined with multivitamins in healthy elderly women—results of a randomized, double-blind, placebocontrolled study", International Journal for Vitamin and Nutrition Research, vol. 73, No. 3, May 2003, pp. 207-214 (Abstract provided).
Alehagen et al., "Cardiovascular mortality and N-terminal-proBNP reduced after combined selenium and coenzyme Q10 supplementation: A 5-year prospective randomized double-blind placebo-controlled trial among elderly Swedish citizens", International Journal of Cardiology, 2012, 7 pages.

(Continued)

*Primary Examiner* — Snigdha Maewall
(74) *Attorney, Agent, or Firm* — Senniger Powers LLP

(57) ABSTRACT

The present invention generally relates to improvements in the bioavailability and/or solubility of coenzyme Q10. For example, the present invention relates to methods for preparing particulate compositions including coenzyme Q10 that generally comprise dispersing and/or dissolving the coenzyme Q10 throughout a suitable solvent, and combining the coenzyme Q10 and an encapsulating (e.g., microencapsulating) agent. The present invention also generally relates to particulate compositions comprising coenzyme Q10 that exhibit improved bioavailability and/or solubility as compared to previous coenzyme Q10 products.

15 Claims, 45 Drawing Sheets

(56) References Cited

U.S. PATENT DOCUMENTS

| | | | |
|---|---|---|---|
| 2009/0060993 A1 | 3/2009 | Schwarz et al. | |
| 2010/0004473 A1 | 1/2010 | Kanaya et al. | |
| 2010/0021573 A1 | 1/2010 | Gonzalez et al. | |
| 2010/0062040 A1 | 3/2010 | Ackley et al. | |
| 2010/0092560 A1* | 4/2010 | Akao | A23F 3/163 424/484 |
| 2010/0151037 A1* | 6/2010 | Jiang | A61K 9/145 424/499 |
| 2011/0064711 A1 | 3/2011 | Eidenberger | |
| 2012/0100123 A1 | 4/2012 | Gonzalez et al. | |

FOREIGN PATENT DOCUMENTS

| | | | |
|---|---|---|---|
| WO | 2007086689 | | 8/2007 |
| WO | WO 2007/086689 | * | 8/2007 |
| WO | 2009027753 | | 3/2009 |

OTHER PUBLICATIONS

Dr. Robert Barry, "The Power of Ubiquinol (Kaneka QH)), The Key to Energy Vitality, and a Healthy Heart", Health Point Press, 2008, 46 pages.

Hsu et al., "Preparation and Characterization of Novel Coenzyme Q10 Nanoparticles Engineered from Microemulsion Precursors", AAPS PharmSciTech 2003; 4 (3) Article 32, 12 pages, <http://www.pharmscitech.org>.

Leary et al., "Magnesium and deaths ascribed to ischaemic heart disease in South Africa", SA Medical Journal, vol. 64, Nov. 5, 1983, pp. 775-776.

David L. Muss, "Relationship Between Water Quality and Deaths From Cardiovascular Disease", Journal (American Water Works Association), vol. 54, No. 11, Nov. 1962, pp. 1371-1378.

* cited by examiner

Database: CoQ10
cumulative distribution

| $x_0/\mu m$ | $Q_0/\%$ | $x_0/\mu m$ | $Q_0/\%$ | $x_0/\mu m$ | $Q_0/\%$ | $x_0/\mu m$ | $Q_0/\%$ |
|---|---|---|---|---|---|---|---|
| 0.90 | 75.58 | 3.70 | 98.44 | 15.00 | 99.93 | 61.00 | 100.00 |
| 1.10 | 85.55 | 4.30 | 98.72 | 18.00 | 99.96 | 73.00 | 100.00 |
| 1.30 | 90.55 | 5.00 | 98.96 | 21.00 | 99.98 | 87.00 | 100.00 |
| 1.50 | 93.27 | 6.00 | 99.23 | 25.00 | 99.99 | 103.00 | 100.00 |
| 1.80 | 95.43 | 7.50 | 99.50 | 30.00 | 99.99 | 123.00 | 100.00 |
| 2.20 | 96.82 | 9.00 | 99.67 | 36.00 | 100.00 | 147.00 | 100.00 |
| 2.60 | 97.53 | 10.50 | 99.78 | 43.00 | 100.00 | 175.00 | 100.00 |
| 3.10 | 98.05 | 12.50 | 99.87 | 51.00 | 100.00 | | | density distribution (log.)

| $x_m/\mu m$ | $q_{lg}$ | $x_m/\mu m$ | $q_{lg}$ | $x_m/\mu m$ | $q_{lg}$ | $x_m/\mu m$ | $q_{lg}$ |
|---|---|---|---|---|---|---|---|
| 0.67 | 1.29 | 3.39 | 0.02 | 13.69 | 0.00 | 55.78 | 0.00 |
| 0.99 | 0.50 | 3.99 | 0.02 | 16.43 | 0.00 | 66.73 | 0.00 |
| 1.20 | 0.30 | 4.64 | 0.02 | 19.44 | 0.00 | 79.69 | 0.00 |
| 1.40 | 0.19 | 5.48 | 0.01 | 22.91 | 0.00 | 94.66 | 0.00 |
| 1.64 | 0.12 | 6.71 | 0.01 | 27.39 | 0.00 | 112.56 | 0.00 |
| 1.99 | 0.07 | 8.22 | 0.01 | 32.86 | 0.00 | 134.47 | 0.00 |
| 2.39 | 0.04 | 9.72 | 0.01 | 39.34 | 0.00 | 160.39 | 0.00 |
| 2.84 | 0.03 | 11.46 | 0.01 | 46.83 | 0.00 | | |

Database: CoQ10
cumulative distribution

| x₀/μm | Q₀/% | x₀/μm | Q₀/% | x₀/μm | Q₀/% | x₀/μm | Q₀/% |
|---|---|---|---|---|---|---|---|
| 0.90 | 74.84 | 3.70 | 98.45 | 15.00 | 99.94 | 61.00 | 100.00 |
| 1.10 | 85.01 | 4.30 | 98.75 | 18.00 | 99.97 | 73.00 | 100.00 |
| 1.30 | 90.14 | 5.00 | 99.01 | 21.00 | 99.98 | 87.00 | 100.00 |
| 1.50 | 92.97 | 6.00 | 99.28 | 25.00 | 99.99 | 103.00 | 100.00 |
| 1.80 | 95.23 | 7.50 | 99.54 | 30.00 | 100.00 | 123.00 | 100.00 |
| 2.20 | 96.70 | 9.00 | 99.70 | 36.00 | 100.00 | 147.00 | 100.00 |
| 2.60 | 97.47 | 10.50 | 99.81 | 43.00 | 100.00 | 175.00 | 100.00 |
| 3.10 | 98.03 | 12.50 | 99.90 | 51.00 | 100.00 | | | density distribution (log.)

| x₀/μm | q₀lg | x₀/μm | q₀lg | x₀/μm | q₀lg | x₀/μm | q₀lg |
|---|---|---|---|---|---|---|---|
| 0.67 | 1.27 | 3.39 | 0.02 | 13.69 | 0.00 | 55.78 | 0.00 |
| 0.99 | 0.51 | 3.99 | 0.02 | 16.43 | 0.00 | 66.73 | 0.00 |
| 1.20 | 0.31 | 4.64 | 0.02 | 19.44 | 0.00 | 79.69 | 0.00 |
| 1.40 | 0.20 | 5.48 | 0.01 | 22.91 | 0.00 | 94.66 | 0.00 |
| 1.64 | 0.12 | 6.71 | 0.01 | 27.39 | 0.00 | 112.56 | 0.00 |
| 1.99 | 0.07 | 8.22 | 0.01 | 32.86 | 0.00 | 134.47 | 0.00 |
| 2.39 | 0.05 | 9.72 | 0.01 | 39.34 | 0.00 | 160.39 | 0.00 |
| 2.84 | 0.03 | 11.46 | 0.00 | 46.83 | 0.00 | | |

Database: CoQ10
cumulative distribution

| $x_0/\mu m$ | $Q_0/\%$ | $x_0/\mu m$ | $Q_0/\%$ | $x_0/\mu m$ | $Q_0/\%$ | $x_0/\mu m$ | $Q_0/\%$ |
|---|---|---|---|---|---|---|---|
| 0.90 | 74.33 | 3.70 | 98.44 | 15.00 | 99.94 | 61.00 | 100.00 |
| 1.10 | 84.65 | 4.30 | 98.75 | 18.00 | 99.97 | 73.00 | 100.00 |
| 1.30 | 89.76 | 5.00 | 99.03 | 21.00 | 99.98 | 87.00 | 100.00 |
| 1.50 | 92.65 | 6.00 | 99.31 | 25.00 | 99.99 | 103.00 | 100.00 |
| 1.80 | 94.99 | 7.50 | 99.57 | 30.00 | 100.00 | 123.00 | 100.00 |
| 2.20 | 96.54 | 9.00 | 99.73 | 36.00 | 100.00 | 147.00 | 100.00 |
| 2.60 | 97.37 | 10.50 | 99.82 | 43.00 | 100.00 | 175.00 | 100.00 |
| 3.10 | 97.98 | 12.50 | 99.90 | 51.00 | 100.00 | | | density distribution (log.)

| $x_m/\mu m$ | $q_0lg$ | $x_m/\mu m$ | $q_0lg$ | $x_m/\mu m$ | $q_0lg$ | $x_m/\mu m$ | $q_0lg$ |
|---|---|---|---|---|---|---|---|
| 0.67 | 1.26 | 3.39 | 0.03 | 13.69 | 0.00 | 55.79 | 0.00 |
| 0.99 | 0.51 | 3.99 | 0.02 | 16.43 | 0.00 | 66.73 | 0.00 |
| 1.20 | 0.31 | 4.64 | 0.02 | 19.44 | 0.00 | 79.69 | 0.00 |
| 1.40 | 0.20 | 5.48 | 0.02 | 22.91 | 0.00 | 94.66 | 0.00 |
| 1.64 | 0.13 | 6.71 | 0.01 | 27.39 | 0.00 | 112.56 | 0.00 |
| 1.99 | 0.08 | 8.22 | 0.01 | 32.86 | 0.00 | 134.47 | 0.00 |
| 2.39 | 0.05 | 9.72 | 0.01 | 39.34 | 0.00 | 160.39 | 0.00 |
| 2.84 | 0.03 | 11.46 | 0.00 | 46.83 | 0.00 | | |

Database: CoQ10
cumulative distribution

| $x_0/\mu m$ | $Q_0/\%$ | $x_0/\mu m$ | $Q_0/\%$ | $x_0/\mu m$ | $Q_0/\%$ | $x_0/\mu m$ | $Q_0/\%$ |
|---|---|---|---|---|---|---|---|
| 0.90 | 74.97 | 3.70 | 98.39 | 15.00 | 99.93 | 61.00 | 100.00 |
| 1.10 | 85.01 | 4.30 | 98.69 | 18.00 | 99.97 | 73.00 | 100.00 |
| 1.30 | 90.09 | 5.00 | 98.96 | 21.00 | 99.98 | 87.00 | 100.00 |
| 1.50 | 92.88 | 6.00 | 99.24 | 25.00 | 99.99 | 103.00 | 100.00 |
| 1.80 | 95.13 | 7.50 | 99.52 | 30.00 | 100.00 | 123.00 | 100.00 |
| 2.20 | 96.60 | 9.00 | 99.69 | 36.00 | 100.00 | 147.00 | 100.00 |
| 2.60 | 97.38 | 10.50 | 99.80 | 43.00 | 100.00 | 175.00 | 100.00 |
| 3.10 | 97.95 | 12.50 | 99.88 | 51.00 | 100.00 | | | density distribution (log.)

| $x_m/\mu m$ | $q_0 lg$ | $x_m/\mu m$ | $q_0 lg$ | $x_m/\mu m$ | $q_0 lg$ | $x_m/\mu m$ | $q_0 lg$ |
|---|---|---|---|---|---|---|---|
| 0.67 | 1.23 | 3.39 | 0.02 | 13.69 | 0.00 | 55.78 | 0.00 |
| 0.99 | 0.50 | 3.99 | 0.02 | 16.43 | 0.00 | 66.73 | 0.00 |
| 1.20 | 0.30 | 4.64 | 0.02 | 19.44 | 0.00 | 79.69 | 0.00 |
| 1.40 | 0.20 | 5.48 | 0.02 | 22.91 | 0.00 | 94.66 | 0.00 |
| 1.64 | 0.12 | 6.71 | 0.01 | 27.39 | 0.00 | 112.56 | 0.00 |
| 1.99 | 0.07 | 8.22 | 0.01 | 32.86 | 0.00 | 134.47 | 0.00 |
| 2.39 | 0.05 | 9.72 | 0.01 | 39.34 | 0.00 | 160.39 | 0.00 |
| 2.84 | 0.03 | 11.46 | 0.00 | 46.83 | 0.00 | | |

Database: CoQ10
cumulative distribution

| $x_0/\mu m$ | $Q_0/\%$ | $x_0/\mu m$ | $Q_0/\%$ | $x_0/\mu m$ | $Q_0/\%$ | $x_0/\mu m$ | $Q_0/\%$ |
|---|---|---|---|---|---|---|---|
| 0.90 | 74.98 | 3.70 | 98.36 | 15.00 | 99.93 | 61.00 | 100.00 |
| 1.10 | 84.99 | 4.30 | 98.67 | 18.00 | 99.96 | 73.00 | 100.00 |
| 1.30 | 90.05 | 5.00 | 98.94 | 21.00 | 99.98 | 87.00 | 100.00 |
| 1.50 | 92.84 | 6.00 | 99.23 | 25.00 | 99.99 | 103.00 | 100.00 |
| 1.80 | 95.08 | 7.50 | 99.51 | 30.00 | 100.00 | 123.00 | 100.00 |
| 2.20 | 96.56 | 9.00 | 99.66 | 36.00 | 100.00 | 147.00 | 100.00 |
| 2.60 | 97.34 | 10.50 | 99.79 | 43.00 | 100.00 | 175.00 | 100.00 |
| 3.10 | 97.92 | 12.50 | 99.88 | 51.00 | 100.00 | | | density distribution (log.)

| $x_m/\mu m$ | $q_0 l g$ | $x_m/\mu m$ | $q_0 l g$ | $x_m/\mu m$ | $q_0 l g$ | $x_m/\mu m$ | $q_0 l g$ |
|---|---|---|---|---|---|---|---|
| 0.67 | 1.28 | 3.39 | 0.02 | 13.69 | 0.00 | 55.78 | 0.00 |
| 0.99 | 0.50 | 3.99 | 0.02 | 16.43 | 0.00 | 66.73 | 0.00 |
| 1.20 | 0.30 | 4.64 | 0.02 | 19.44 | 0.00 | 79.69 | 0.00 |
| 1.40 | 0.20 | 5.48 | 0.02 | 22.91 | 0.00 | 94.66 | 0.00 |
| 1.64 | 0.12 | 6.71 | 0.01 | 27.35 | 0.00 | 112.56 | 0.00 |
| 1.99 | 0.07 | 8.22 | 0.01 | 32.86 | 0.00 | 134.47 | 0.00 |
| 2.39 | 0.05 | 9.72 | 0.01 | 39.34 | 0.00 | 160.39 | 0.00 |
| 2.84 | 0.03 | 11.46 | 0.00 | 46.83 | 0.00 | | |

Database: CoQ10
cumulative distribution

| x₀/μm | Q₀/% | x₀/μm | Q₀/% | x₀/μm | Q₀/% | x₀/μm | Q₀/% |
|---|---|---|---|---|---|---|---|
| 0.90 | 75.11 | 3.70 | 98.33 | 15.00 | 99.93 | 61.00 | 100.00 |
| 1.10 | 85.06 | 4.30 | 98.64 | 18.00 | 99.96 | 73.00 | 100.00 |
| 1.30 | 90.08 | 5.00 | 98.91 | 21.00 | 99.98 | 87.00 | 100.00 |
| 1.50 | 92.85 | 6.00 | 99.20 | 25.00 | 99.99 | 103.00 | 100.00 |
| 1.80 | 95.08 | 7.50 | 99.49 | 30.00 | 100.00 | 123.00 | 100.00 |
| 2.20 | 96.55 | 9.00 | 99.67 | 36.00 | 100.00 | 147.00 | 100.00 |
| 2.60 | 97.32 | 10.50 | 99.78 | 43.00 | 100.00 | 175.00 | 100.00 |
| 3.10 | 97.89 | 12.50 | 99.87 | 51.00 | 100.00 | | | density distribution (log.)

| x₀/μm | q₀lg | x₀/μm | q₀lg | x₀/μm | q₀lg | x₀/μm | q₀lg |
|---|---|---|---|---|---|---|---|
| 0.67 | 1.28 | 3.39 | 0.02 | 13.69 | 0.00 | 55.78 | 0.00 |
| 0.99 | 0.50 | 3.99 | 0.02 | 16.43 | 0.00 | 66.73 | 0.00 |
| 1.20 | 0.30 | 4.64 | 0.02 | 19.44 | 0.00 | 79.69 | 0.00 |
| 1.40 | 0.19 | 5.48 | 0.02 | 22.91 | 0.00 | 94.66 | 0.00 |
| 1.64 | 0.12 | 6.71 | 0.01 | 27.39 | 0.00 | 112.56 | 0.00 |
| 1.99 | 0.07 | 8.22 | 0.01 | 32.86 | 0.00 | 134.47 | 0.00 |
| 2.39 | 0.05 | 9.72 | 0.01 | 39.34 | 0.00 | 160.39 | 0.00 |
| 2.84 | 0.03 | 11.46 | 0.01 | 46.83 | 0.00 | | |

Database: CoO10
cumulative distribution

| x₀/μm | Q₃/% | x₀/μm | Q₃/% | x₀/μm | Q₃/% | x₀/μm | Q₃/% |
|---|---|---|---|---|---|---|---|
| 0.90 | 1.60 | 3.70 | 6.80 | 15.00 | 47.15 | 61.00 | 97.50 |
| 1.10 | 2.22 | 4.30 | 7.89 | 18.00 | 56.75 | 73.00 | 99.18 |
| 1.30 | 2.75 | 5.00 | 9.43 | 21.00 | 64.44 | 87.00 | 100.00 |
| 1.50 | 3.22 | 6.00 | 12.17 | 25.00 | 72.44 | 103.00 | 100.00 |
| 1.80 | 3.82 | 7.50 | 17.30 | 30.00 | 79.84 | 123.00 | 100.00 |
| 2.20 | 4.59 | 9.00 | 23.25 | 36.00 | 86.14 | 147.00 | 100.00 |
| 2.60 | 5.11 | 10.50 | 29.50 | 43.00 | 91.13 | 175.00 | 100.00 |
| 3.10 | 5.86 | 12.50 | 37.71 | 51.00 | 94.79 | | | density distribution (log.)

| x₀/μm | q₃lg | x₀/μm | q₃lg | x₀/μm | q₃lg | x₀/μm | q₃lg |
|---|---|---|---|---|---|---|---|
| 0.67 | 0.03 | 3.39 | 0.05 | 13.69 | 0.52 | 55.78 | 0.15 |
| 0.99 | 0.03 | 3.99 | 0.07 | 16.43 | 0.53 | 66.73 | 0.09 |
| 1.20 | 0.03 | 4.64 | 0.10 | 19.44 | 0.50 | 79.69 | 0.05 |
| 1.40 | 0.03 | 5.48 | 0.15 | 22.91 | 0.46 | 94.66 | 0.00 |
| 1.64 | 0.03 | 6.71 | 0.23 | 27.39 | 0.41 | 112.56 | 0.00 |
| 1.99 | 0.03 | 8.22 | 0.33 | 32.86 | 0.35 | 134.47 | 0.00 |
| 2.39 | 0.04 | 9.72 | 0.41 | 39.34 | 0.28 | 160.39 | 0.00 |
| 2.84 | 0.04 | 11.46 | 0.47 | 46.83 | 0.21 | | |

Database: CoQ10
cumulative distribution

| $x_0/\mu m$ | $Q_3/\%$ | $x_0/\mu m$ | $Q_3/\%$ | $x_0/\mu m$ | $Q_3/\%$ | $x_0/\mu m$ | $Q_3/\%$ |
|---|---|---|---|---|---|---|---|
| 0.90 | 1.75 | 3.70 | 7.86 | 15.00 | 49.39 | 61.00 | 97.68 |
| 1.10 | 2.46 | 4.30 | 9.15 | 18.00 | 59.20 | 73.00 | 99.24 |
| 1.30 | 3.07 | 5.00 | 10.94 | 21.00 | 66.36 | 87.00 | 100.00 |
| 1.50 | 3.60 | 6.00 | 14.03 | 25.00 | 74.17 | 103.00 | 100.00 |
| 1.80 | 4.29 | 7.50 | 19.61 | 30.00 | 81.17 | 123.00 | 100.00 |
| 2.20 | 5.10 | 9.00 | 25.87 | 36.00 | 87.09 | 147.00 | 100.00 |
| 2.60 | 5.83 | 10.50 | 32.29 | 43.00 | 91.76 | 175.00 | 100.00 |
| 3.10 | 6.72 | 12.50 | 40.57 | 51.00 | 95.16 | | | density distribution (log.)

| $x_m/\mu m$ | $q_3lg$ | $x_m/\mu m$ | $q_3lg$ | $x_m/\mu m$ | $q_3lg$ | $x_m/\mu m$ | $q_3lg$ |
|---|---|---|---|---|---|---|---|
| 0.67 | 0.03 | 3.39 | 0.06 | 13.69 | 0.31 | 55.78 | 0.14 |
| 0.99 | 0.03 | 3.99 | 0.09 | 16.43 | 0.31 | 66.73 | 0.09 |
| 1.20 | 0.04 | 4.64 | 0.12 | 19.44 | 0.48 | 79.69 | 0.04 |
| 1.40 | 0.04 | 5.48 | 0.17 | 22.91 | 0.44 | 94.66 | 0.00 |
| 1.64 | 0.04 | 6.71 | 0.25 | 27.39 | 0.38 | 112.56 | 0.00 |
| 1.99 | 0.04 | 8.22 | 0.34 | 32.86 | 0.32 | 134.47 | 0.00 |
| 2.39 | 0.04 | 9.72 | 0.42 | 39.34 | 0.26 | 160.39 | 0.00 |
| 2.84 | 0.05 | 11.46 | 0.48 | 46.83 | 0.20 | | |

Database: CoQ10
cumulative distribution

| $x_0/\mu m$ | $Q_3/\%$ | $x_0/\mu m$ | $Q_3/\%$ | $x_0/\mu m$ | $Q_3/\%$ | $x_0/\mu m$ | $Q_3/\%$ |
|---|---|---|---|---|---|---|---|
| 0.90 | 1.89 | 3.70 | 8.84 | 15.00 | 52.32 | 61.00 | 97.79 |
| 1.10 | 2.65 | 4.30 | 10.35 | 18.00 | 61.31 | 73.90 | 99.27 |
| 1.30 | 3.32 | 5.00 | 12.40 | 21.00 | 68.37 | 87.90 | 100.00 |
| 1.50 | 3.90 | 6.00 | 15.84 | 25.00 | 75.62 | 103.00 | 100.00 |
| 1.80 | 4.68 | 7.50 | 21.84 | 30.00 | 82.25 | 123.00 | 100.00 |
| 2.20 | 5.60 | 9.00 | 28.36 | 36.00 | 87.83 | 147.00 | 100.00 |
| 2.60 | 6.45 | 10.50 | 34.91 | 43.00 | 92.21 | 175.00 | 100.00 |
| 3.10 | 7.50 | 12.50 | 43.19 | 51.00 | 95.42 | | | density distribution (log.)

| $x_m/\mu m$ | $q_3 lg$ | $x_m/\mu m$ | $q_3 lg$ | $x_m/\mu m$ | $q_3 lg$ | $x_m/\mu m$ | $q_3 lg$ |
|---|---|---|---|---|---|---|---|
| 0.67 | 0.03 | 3.39 | 0.08 | 13.69 | 0.50 | 55.76 | 0.13 |
| 0.99 | 0.04 | 3.99 | 0.10 | 16.43 | 0.49 | 66.73 | 0.08 |
| 1.20 | 0.04 | 4.64 | 0.14 | 19.44 | 0.46 | 79.69 | 0.04 |
| 1.40 | 0.04 | 5.48 | 0.19 | 22.91 | 0.42 | 94.66 | 0.00 |
| 1.64 | 0.04 | 6.71 | 0.27 | 27.39 | 0.36 | 112.56 | 0.00 |
| 1.99 | 0.05 | 8.22 | 0.36 | 32.36 | 0.31 | 134.47 | 0.00 |
| 2.39 | 0.05 | 9.72 | 0.42 | 39.34 | 0.25 | 160.39 | 0.00 |
| 2.84 | 0.06 | 11.46 | 0.48 | 46.83 | 0.19 | | |

Database: CoQ10

Database: CoQ10
cumulative distribution

| $x_0/\mu m$ | $Q_3/\%$ | $x_0/\mu m$ | $Q_3/\%$ | $x_0/\mu m$ | $Q_3/\%$ | $x_0/\mu m$ | $Q_3/\%$ |
|---|---|---|---|---|---|---|---|
| 0.90 | 1.66 | 3.70 | 7.44 | 15.00 | 49.54 | 61.00 | 97.67 |
| 1.10 | 2.30 | 4.30 | 8.72 | 18.00 | 58.89 | 73.00 | 99.24 |
| 1.30 | 2.87 | 5.00 | 10.50 | 21.00 | 66.30 | 87.00 | 100.00 |
| 1.50 | 3.36 | 6.00 | 13.60 | 25.00 | 73.97 | 103.00 | 100.00 |
| 1.80 | 4.01 | 7.50 | 19.19 | 30.00 | 81.03 | 123.00 | 100.00 |
| 2.20 | 4.77 | 9.00 | 25.46 | 36.00 | 87.00 | 147.00 | 100.00 |
| 2.60 | 5.47 | 10.50 | 31.89 | 43.00 | 91.70 | 175.00 | 100.00 |
| 3.10 | 6.33 | 12.50 | 40.19 | 51.00 | 95.14 | | | density distribution (log.)

| $x_m/\mu m$ | $q_3 lg$ | $x_m/\mu m$ | $q_3 lg$ | $x_m/\mu m$ | $q_3 lg$ | $x_m/\mu m$ | $q_3 lg$ |
|---|---|---|---|---|---|---|---|
| 0.67 | 0.03 | 3.39 | 0.06 | 13.69 | 0.51 | 55.78 | 0.14 |
| 0.99 | 0.03 | 3.99 | 0.09 | 16.43 | 0.51 | 66.73 | 0.09 |
| 1.20 | 0.03 | 4.64 | 0.12 | 19.44 | 0.48 | 79.69 | 0.04 |
| 1.40 | 0.03 | 5.48 | 0.17 | 22.91 | 0.44 | 94.66 | 0.00 |
| 1.64 | 0.04 | 6.71 | 0.25 | 27.39 | 0.39 | 112.56 | 0.00 |
| 1.99 | 0.04 | 8.22 | 0.34 | 32.86 | 0.33 | 134.47 | 0.00 |
| 2.39 | 0.04 | 9.72 | 0.42 | 39.34 | 0.26 | 160.39 | 0.00 |
| 2.84 | 0.05 | 11.46 | 0.48 | 46.83 | 0.20 | | |

SOLID PARTICULATE COMPOSITIONS COMPRISING COENZYME Q10

FIELD OF THE INVENTION

The present invention generally relates to improvements in the bioavailability and/or solubility of coenzyme Q10. For example, the present invention relates to methods for preparing particulate compositions including coenzyme Q10 that generally comprise dispersing and/or dissolving the coenzyme Q10 throughout a suitable solvent, and combining the coenzyme Q10 and an encapsulating (e.g., microencapsulating) agent. The present invention also generally relates to particulate compositions comprising coenzyme Q10 that exhibit improved bioavailability and/or solubility as compared to previous coenzyme Q10 products.

BACKGROUND OF THE INVENTION

Coenzyme Q10, also known as ubiquinone or CoQ10, is a lipophilic, vitamin-like substance present in most eukaryotic cells. Coenzyme Q10 acts as a component of the cellular respiration chain, which generates cellular energy in the form of ATP. It has also been used for the treatment of several diseases, including cardiovascular disease, high blood pressure, muscular dystrophy, and periodontal disease.

Due to its size and structure, coenzyme Q10 is practically insoluble in water, exhibiting an extremely low water solubility of, for example, between 2-3 parts per million (ppm) (i.e., 2-3 mg/L). Because of its low water solubility, previous coenzyme Q10 formulations have shown very low bioavailability when taken as an oral supplement.

Various approaches to improving the bioavailability of coenzyme Q10 have been attempted in the prior art. A common approach involves placing coenzyme Q10 into solution with a water-miscible organic solvent, usually in combination with one or more emulsifiers to form a liquid coenzyme Q10 formulation. For example, U.S. Pat. No. 6,056,971 discloses that the water solubility of coenzyme Q10 is increased when dissolved in a mixture of an edible polyhydric alcohol and a nonionic surfactant. Liquid coenzyme Q10 formulations, however, frequently require the use of soft gelatin capsules, which are relatively expensive to manufacture and exhibit a reduced shelf life as compared to solid tablets. A few approaches use variations on this theme that allow production of solid coenzyme Q10 compositions. For example, U.S. Pat. No. 5,989,583 discloses a composition wherein coenzyme Q10 is dissolved in a digestible fat that is solid at room temperature. This formulation can be spray-chilled to produce solid particles with improved dispersibility in water. Such dried powder coenzyme Q10 formulations in the prior art, however, still exhibit lower levels of water solubility and bioavailability than are desired for effective oral supplementation.

Another method reported to increase the bioavailability of coenzyme Q10 is reducing the particle size to the submicron range. The production of submicron particle sizes through traditional techniques, however, requires significant effort, energy, and expense. For example, U.S. Pat. No. 6,861,447 discloses a method to increase bioavailability by forming a complex of coenzyme Q10 and cyclodextrin, which is subsequently ground into a fine powder using a ball mill. Mechanical milling processes are labor-intensive and expensive to operate, and as such are not ideal for production on a commercial scale.

One approach to increasing the bioavailability of highly lipophilic substances involves the use of colloidal particle compositions. The technology of mixing hydrophobic substances in coating materials, described by Sair et al. in U.S. Pat. No. 4,230,687, has been the basis for creating various forms of stable microdispersions. For example, the process of spray drying an emulsion of lecithin, organic oil and a nonionic poloxamer surfactant was developed for the creation of shelf stable flavorants in the food industry (U.S. Pat. No. 5,362,425). A similar approach has been used to increase the solubility of phytochemicals, described in U.S. Pat. No. 6,086,915 to Zeligs et al. The method of the '915 patent involves co-dissolving the phytochemicals in an appropriate solvent, an emulsifier, and phospholipids, followed by spray-drying the resulting mixture to create solid particles. This process was found to promote enhanced absorption of the phytochemicals when dissolved and emulsified within the small intestine of a human or animal.

Recently, the prior art has begun to apply colloidal technology to improve the solubility of coenzyme Q10 compositions. For example, U.S. Pat. No. 7,026,361 discloses that aqueous dispersibility may be improved by encasing coenzyme Q10 within a protective, water-soluble colloid, which is formed by emulsifying coenzyme Q10 in an aqueous medium in the presence of an organic acid. The composition of the '361 patent can be formulated as either a liquid composition, or as solid particles formed by spray drying. While this technology offers improved solubility relative to more traditional formulations of coenzyme Q10 (e.g., gelatin capsule formulations), it still does not provide the desired level of bioavailability necessary for cost-effective coenzyme Q10 supplementation.

One goal of the present invention is to improve on the methods and compositions in the prior art by producing coenzyme Q10 compositions with improved bioavailability and/or solubility. Another goal of the present invention is to produce a dry powder composition comprising coenzyme Q10 including, for example, dry powder compositions having moisture contents of less than about 2% by weight, or lower. A further goal of the present invention is the provision of coenzyme Q10 products that allow preparation of coenzyme Q10 formulations that exhibit greater stability (e.g., storage stability) than prior coenzyme Q10 formulations. There is significant evidence that ingestion of coenzyme Q10 supplements provides beneficial effects, particularly in the prevention and treatment of various diseases, including cardiovascular disease. Currently available supplements, however, must contain relatively high doses of coenzyme Q10 to compensate for the low bioavailability, resulting in additional expense that is detrimental to consumers. There is therefore a need in the art for an improved coenzyme Q10 composition that exhibits improved bioavailability and/or solubility, is economical for mass production, and suitable for preparation of coenzyme Q10 formulations exhibiting improved storage stability.

SUMMARY OF THE INVENTION

The present invention generally relates to coenzyme Q10 compositions exhibiting improved bioavailability, improved rates of solubility (i.e., release rate), and/or improved overall, or total solubility as compared to conventional coenzyme Q10 products, and further provides methods for preparing such coenzyme Q10 compositions.

Briefly, therefore, in various embodiments, the present invention is directed to a method for preparing a particulate composition comprising coenzyme Q10, the method comprising: combining an organic phase and an aqueous phase, thereby forming an emulsion, wherein the organic phase comprises coenzyme Q10 and a solvent and the aqueous phase comprises a water-soluble encapsulator; and drying the emulsion, thereby forming a composition comprising solid particles comprising coenzyme Q10.

In various other embodiments, the present invention is directed to a method for preparing a particulate composition comprising coenzyme Q10, the method comprising: combining coenzyme Q10, a solvent, and a first surfactant to form an organic phase; combining water, a water-soluble encapsulator, and a second surfactant to form an aqueous phase; combining the organic phase with the aqueous phase under agitation, thereby forming an emulsion; and drying the emulsion, thereby forming a composition comprising solid particles comprising coenzyme Q10.

In further embodiments, the present invention is directed to a solid particulate composition comprising coenzyme Q10, a first surfactant having a hydrophile-lipophile balance (HLB) of at least 8, a second surfactant having a hydrophile-lipophile balance (HLB) of less than 8, and a water-soluble encapsulator.

In still further embodiments, the present invention is directed to a solid particulate composition comprising coenzyme Q10, wherein the solid particles have a particle size distribution such that at least about 50% by weight of the particles have an overall particle size of from about 8 μm to about 15 μm in diameter, and wherein the solid particles are in the form of a water-soluble matrix comprising an encapsulator and having discrete microparticulates of coenzyme Q10 dispersed throughout the water-soluble matrix.

In further embodiments, the present invention is directed to a tablet dosage form comprising a solid particulate composition comprising coenzyme Q10 and one or more biologically acceptable excipients, wherein the particulate coenzyme Q10 composition comprises a solid matrix comprising an encapsulator, and microparticulates are dispersed throughout the solid matrix, wherein the microparticulates comprise coenzyme Q10, a first surfactant, and a second surfactant.

In various other embodiments, the present invention is directed to a formulation for oral administration comprising coenzyme Q10, wherein the total exposure of coenzyme Q10, as determined by the area under the plasma concentration vs. time curve at 4 hours following oral administration of a dose containing about 60 (milligrams) mg of coenzyme Q10, is at least about 0.15 mg·h/L (milligrams*hour per liter).

In further embodiments, the present invention is directed to a formulation for oral administration comprising coenzyme Q10, wherein the total exposure of coenzyme Q10, as determined by the area under the plasma concentration vs. time curve at 6 hours following oral administration of a dose containing about 60 mg of coenzyme Q10, is at least about 0.5 mg·h/L.

In still further embodiments, the present invention is directed to a formulation for oral administration comprising coenzyme Q10, wherein the total exposure of coenzyme Q10, as determined by the area under the plasma concentration vs. time curve at 8 hours following oral administration of a dose containing about 60 mg of coenzyme Q10, is at least about 1 mg·h/L.

In further embodiments, the present invention is directed to a formulation for oral administration comprising coenzyme Q10, wherein the total exposure of coenzyme Q10, as determined by the area under the plasma concentration vs. time curve at 10 hours following oral administration of a dose containing about 60 mg of coenzyme Q10, is at least about 1.5 mg·h/L.

In even further embodiments, the present invention is directed to a formulation for oral administration comprising coenzyme Q10, wherein the total exposure of coenzyme Q10, as determined by the area under the plasma concentration vs. time curve at 12 hours following oral administration of a dose containing about 60 mg of coenzyme Q10, is at least about 2.0 mg·h/L.

In still further embodiments, the present invention is directed to a formulation for oral administration comprising coenzyme Q10, wherein the total exposure of coenzyme Q10, as determined by the area under the plasma concentration vs. time curve at 14 hours following oral administration of a dose containing about 60 mg of coenzyme Q10, is at least about 2.5 mg·h/L.

In even further embodiments, the present invention is directed to a formulation for oral administration comprising coenzyme Q10, wherein the maximum plasma concentration ($C_{max}$), as determined by the maximum concentration value reached on the plasma concentration vs. time curve, is achieved in less than 7 hours following oral administration of a dose containing about 60 mg coenzyme Q10.

In various other embodiments, the present invention is directed to a formulation for oral administration comprising coenzyme Q10, wherein the time of the first observed rise in plasma concentration from 0 mg/L ($t_{lag}$) following administration of a dose containing about 60 mg coenzyme Q10 is less than 1 hour.

In still further embodiments, the present invention is directed to a formulation for oral administration comprising coenzyme Q10, wherein: (i) the formulation comprises coenzyme Q10, a first surfactant having a hydrophile-lipophile balance (HLB) of at least 8, a second surfactant having a hydrophile-lipophile balance (HLB) of less than 8, and a water-soluble encapsulator; and (ii) the total exposure of coenzyme Q10 (AUC), as determined by the area under the plasma concentration vs. time curve at 24 hours following oral administration of a dose containing about 60 mg of coenzyme Q10, is at least about 4 mg·h/L.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE PREFERRED EMBODIMENTS

Figure 1:
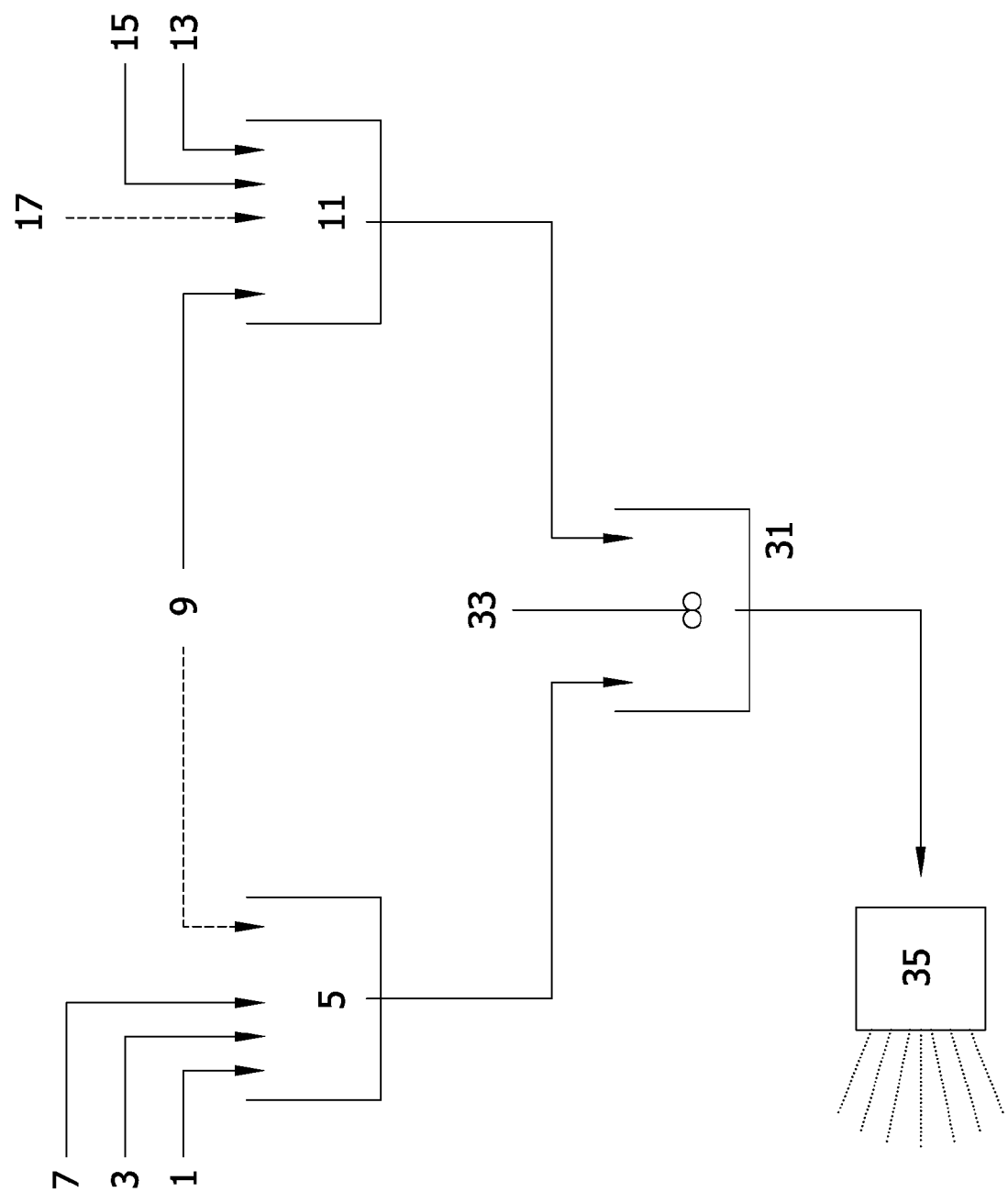
FIG. 1 provides an overview of one embodiment of the present invention, which is a method of preparing solid particulate compositions comprising coenzyme Q10.

Described herein are methods for preparing novel coenzyme Q10 compositions exhibiting improved stability, solubility, and/or bioavailability of the coenzyme Q10 active ingredient as compared to conventional coenzyme Q10 products.

Generally, various embodiments of the present invention include combining particulate coenzyme Q10 with a suitable solvent, one or more surfactants, and an encapsulating medium (i.e., encapsulator) to provide a novel, solid particulate coenzyme Q10 composition. In accordance with the present invention, combining the particulate coenzyme Q10, a suitable solvent, one or more surfactants, and an encapsulator (e.g., a starch) provides an emulsion of very fine droplets (e.g., microdroplets), wherein the coenzyme Q10 is associated with the surfactant(s) and is dispersed throughout an aqueous mixture comprising the encapsulating medium. From this mixture may be prepared the novel, particulate coenzyme Q10 composition in the form of solid particles. Generally, each solid particle itself contains discrete "microparticulates" including coenzyme Q10 associated with the surfactant(s) that are dispersed throughout a solid matrix defining the solid particles and including the encapsulator. In this manner, the particles of the compositions of the present invention are often referred to herein as "colloidal particles."

The solid particulate product is typically prepared upon removal of water from the aqueous mixture, for example, by spray drying, to provide the solid coenzyme Q10 particles that comprise a water-soluble matrix, wherein microparticulates of coenzyme Q10 associated with the one or more surfactants are dispersed throughout the encapsulating medium. These microparticulates are typically in an amorphous, non-crystalline form and are easily released from the water-soluble encapsulator upon contact with intestinal fluids. Upon release into the digestive tract, the microparticulates are compatible and coalesce with intestinal phospholipid/bile salt micelles, resulting in increased absorption through the intestinal wall.

As detailed elsewhere herein, the nature of the solvent and/or one or more surfactants may be selected to promote formation of the novel composition. For example, in various preferred embodiments, the solvent with which the particulate coenzyme Q10 is combined is partly water miscible. Due to this partial water miscibility, along with solubility of coenzyme Q10 within the organic phase, dispersion of the coenzyme Q10 microdroplets throughout the aqueous encapsulating medium occurs.

Advantageously, the novel compositions of the present invention provide improved bioavailability and/or solubility of coenzyme Q10 over prior products. In particular, the novel compositions of the present invention are believed to provide improved rates of solubility and/or improved overall solubility. In this manner, the present invention provides for compositions containing lower doses of coenzyme Q10, but that are nonetheless as effective as other, higher dosage compositions. Accordingly, the present invention allows for lower cost coenzyme Q10 compositions, from the perspective of both the manufacturer and the end consumer. Likewise, the compositions of the present invention are suitable for preparing dosage forms having comparable dosages to those of conventional coenzyme Q10 formulations, but improved effectiveness based on the improvement in bioavailability and/or stability. Further in accordance with the present invention, the novel, particulate coenzyme Q10 composition exhibiting advantageous bioavailability and/or solubility is suitable for preparing tablet compositions. Since tablet compositions are easier to manufacture than conventional forms of coenzyme Q10 formulations (e.g., gelatin capsules or soft gels), and exhibit greater stability and increased shelf life compared to conventional delivery forms, this likewise represents an advantage over the prior art.

As used herein, the term "microdispersion" refers to an oil-in-water emulsion wherein very fine droplets of coenzyme Q10 solution, typically associated with one or more surfactants, are dispersed throughout an aqueous mixture.

The term "microdroplets" refers to very fine particles of coenzyme Q10, typically associated with one or more surfactants, which are dispersed throughout the aqueous phase comprising the encapsulating medium. Similarly, the term "microparticulates" generally refers to very small particulates of coenzyme Q10, typically associated with one or more surfactants, which are dispersed throughout the solid particles of the present invention.

In the context of the methods of the present invention, the term "organic phase" generally refers to a phase comprising coenzyme Q10. The term "aqueous phase" generally refers to a phase comprising a water-soluble encapsulator.

A. Coenzyme Q10

Generally, the term "coenzyme Q" refers to a class of fat-soluble 1,4-benzoquinone compounds having a long tail of multiple isoprenyl chemical subunits.

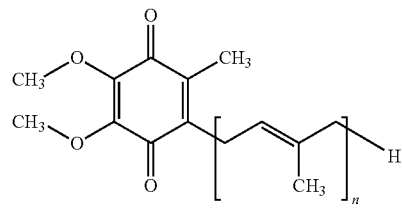

Coenzyme Q10 is the species of coenzyme Q most prevalent in human mitochondria, wherein the notation 'Q' refers to the quinone chemical group, and '10' refers to the number of isoprenyl chemical subunits in its tail. In animals other than humans, different structures of coenzyme Q may be more prevalent. Coenzyme Q9, for example, is the most prevalent species of coenzyme Q found in rats and mice. Accordingly, as used throughout this application, the term "coenzyme Q10" refers generally to a coenzyme Q having from 7 to 11 isoprene units. In various embodiments, however, coenzyme Q10 refers to a coenzyme Q having 10 isoprene units (i.e., n=10 in the above formula).

Additionally, coenzyme Q10 is commercially sold in its fully oxidized form (also known as "ubiquinone"). In the body, however, more than 90% of coenzyme Q compounds are present in the active antioxidant form (also known as "ubiquinol"). As used herein, the term "coenzyme Q10"

generally refers to all structures of coenzyme Q regardless of oxidation status, as well as various salts and derivatives thereof.

Industrially produced coenzyme Q10 is widely available from a number of suppliers. Commercially available, USP grade powders typically take the form of a dry, yellow-orange colored solid powder. Preferred embodiments of the present invention utilize a coenzyme Q10 starting material with a purity of at least about 98% by weight. Suitable sources of coenzyme Q10 include those prepared in accordance with U.S. Pat. No. 7,910,340, the entire contents of which are incorporated by reference for all relevant purposes. For example, one suitable source of coenzyme Q10 is KANEKA Q10 (Kaneka Nutrients L.P.)

As noted above, coenzyme Q10 exhibits extremely low solubility in water. Accordingly, the term "organic phase" is used throughout to refer to the phase comprising coenzyme Q10. Conversely, the term "aqueous phase" refers to the phase comprising water and one or more water-soluble encapsulators.

As detailed in Example 6, commercially available coenzyme Q10 powders typically have a mean particle size that is significantly larger than the microparticulates of coenzyme Q10 achieved by the present invention. Typically, commercial powders have an average particle size, on a mass basis, of approximately 15 μm, with approximately 90% by mass of the particles having a largest dimension greater than 5 μm. In contrast, for the microparticulates achieved by the present invention, at least about 90% by weight of the microparticulates of the particles have a largest dimension of from about 1 to about 4 μm. As noted above and detailed elsewhere herein, it is currently believed that the particle size of the microparticulates provided by the present invention contribute to enhanced solubility of the coenzyme Q10.

B. Methods of Preparation

Referring now to FIG. 1, to prepare the particulate compositions, generally coenzyme Q10 1 is mixed with an organic solvent 3 to form the organic phase 5, and a water soluble encapsulator 15 is combined with water 13 to form an aqueous phase 11. The organic phase 5 is then combined with the aqueous phase 11.

A combination of surfactants is typically employed: a first surfactant to promote the solubility of the coenzyme Q10 throughout the organic solvent (often referred to herein as a solubilizing surfactant), and a second surfactant to act as an emulsifier when the organic phase is combined with an aqueous phase (often referred to herein as an emulsifying surfactant).

The solubilizing surfactant has a hydrophilic-lipophilic balance (HLB) that is high enough to promote increased solubility of coenzyme Q10 in the organic phase. In contrast, the emulsifying surfactant has a lower HLB and promotes a reduction in the size of the dispersed coenzyme Q10 organic phase upon mixing in the aqueous phase. Together, this combination of surfactants serves to maintain a stable dispersion of coenzyme Q10 microdroplets within the aqueous phase. The surfactants also serve to increase the bioavailability of the coenzyme Q10 when the particles are dispersed in the intestinal tract.

The aqueous phase is a liquid medium comprising one or more water-soluble encapsulators. When the organic and aqueous phases are combined, typically by mixing under high shear, the result is an emulsion of very fine droplets comprising coenzyme Q10 dispersed throughout the aqueous phase. When this mixture is dried (e.g., by spray-drying), the result is a fine powder comprising solid particles. Each solid particle itself comprises discrete microparticulates of coenzyme Q10, associated with one or more surfactants, dispersed throughout the encapsulating medium.

1. Solvent

Because of its structure and high molecular weight, coenzyme Q10 has an extremely low solubility in water, and is soluble in only a limited number of oils. Accordingly, a suitable solvent typically exhibits good solubility of coenzyme Q10, and typically is at least partly immiscible in water. To the extent that the solvent is partly miscible in water, it will help promote the formation of a fine emulsion of coenzyme Q10 when added to an aqueous solution. Accordingly, it is desirable to select a solvent that provides an appropriate balance between high degree of solubility of coenzyme Q10, a highly lipophilic compound, while retaining partial miscibility in water.

Again with reference to FIG. 1, coenzyme Q10 1 and a suitable solvent 3 are mixed to form an organic phase 5. Typical organic solvents generally include biologically acceptable alcohols, ketones, and esters, and mixtures thereof. Non-limiting examples of preferred alcohol solvents include hexanol, ethanol, butanol, heptanol, 2-methyl-1-pentanol, and propylene glycol. Non-limiting examples of preferred ketone solvents include methyl ethyl ketone and acetone. A non-limiting example of a preferred ester solvent is ethyl acetate. In various preferred embodiments, the organic solvent is hexanol or acetone. Hexanol is particularly preferred, as it is partly miscible in water and coenzyme Q10 is more soluble in hexanol as compared to other solvents. As detailed elsewhere herein, the improved solubility of coenzyme Q10 allows a stable emulsion to be achieved with a smaller amount of surfactant, thereby allowing for and increased proportion of coenzyme Q10 in the final composition.

Typically, the weight ratio of organic solvent to coenzyme Q10 in the organic phase is from about 0.25:1 to about 4:1, more typically from about 0.75:1 to about 1.25:1, still more typically from about 0.8:1 to about 1:1 (e.g., about 0.9:1).

2. Solubilizing Surfactants

As noted above, coenzyme Q10 is not only relatively insoluble in water, but exhibits less than the desired solubility in many organic solvents as well. Accordingly, one or more solubilizing surfactants are added to the organic phase to promote dissolution in the organic solvent. The increased solubility of coenzyme Q10 also promotes the formation of a more stable emulsion when the coenzyme Q10-containing organic phase is combined with an aqueous phase.

In the methods of the present invention, the solubilizing surfactant may be mixed with the coenzyme Q10 before, during, or after combining coenzyme Q10 with the organic solvent. In preferred embodiments, the solubilizing surfactant is mixed with the coenzyme Q10 before combining with the solvent, thereby promoting more efficient dissolution of the coenzyme Q10 throughout the solvent.

Again with reference to FIG. 1, solubilizing (i.e., first) surfactant 7 is introduced into organic phase 5. Suitable surfactants for this purpose generally have an HLB that is high enough to promote increased solubility in the organic phase. Typically, the HLB of the solubilizing surfactant is at least about 8, more typically at least about 9, more typically at least about 10, more typically at least about 11, more typically at least about 12, more typically at least about 13, and still more typically at least about 14. In some embodiments, a combination of two or more solubilizing surfactants may be used.

Non-limiting examples of suitable solubilizing (first) surfactants include polyvinylpyrrolidone, polyoxyethylene stearate, sodium cholate, deoxycholate, taurocholate, carboxylic acid esters of polyethylene glycol, tocopherol polyethylene glycol succinate, and various semi-solid industrial excipients. The use of tocopherol polyethylene glycol succinate ("TPGS"), in particular, is known to increase uptake/absorption of lipophilic compounds across the intestinal wall.

In more preferred embodiments, an amphiphilic excipient is utilized as the solubilizing surfactant. In various embodiments, the solubilizing surfactant comprises an alkoxylated fatty acid glyceride or fatty acid ester. Non-limiting examples of suitable alkoxylated fatty acid glycerides include polyoxyglycerides such as pegylated glyerols esterified with lauric acid (often referred to as lauroyl macroglycerides, e.g., lauroyol polyoxyl-32-glycerides) and pegylated glycerols esterified with stearic acid (often referred to as stearoyl macroglycerides, e.g., stearoyl polyoxyl-32-glycerides). Additional suitable alkoxylated fatty acid glycerides include polyethyleneglycol stearates and caproyl polyoxy glycerides. The polyoxyglyceride is typically a lauroyl macroglyceride. Suitable fatty acid esters include polyoxyethyleneoxypropyleneglycol fatty acid esters.

In some cases, commercially available semi-solid industrial excipients may provide a higher melting point and a more favorable hydrophilic-lipophilic balance than other surfactants. One suitable amphiphilic excipient comprising a polyoxyglyceride, and specifically a lauroyl macroglyceride, is sold under the trade name GELUCIRE 44/14. GELUCIRE 44/14, in particular, is also believed to overcome the p-glycoprotein efflux pump in the human intestinal tract, which helps it to increase the bioavailability of coenzyme Q10 when the product is consumed orally.

Generally, the weight ratio of solubilizing surfactant to coenzyme Q10 is selected to maximize the stability of the emulsion. Typically, the weight ratio of solubilizing surfactant to coenzyme Q10 is typically from about 0.25:1 to about 2:1, more typically from about 0.5:1 to about 1:1, more typically from about 0.6:1 to about 0.85:1, and more typically from about 0.7:1 to about 0.8:1. If hexanol is selected as the organic solvent, less solubilizing surfactant will be required, as coenzyme Q10 is more soluble in hexanol than in other preferred solvents. In these more preferred embodiments, the ratio of the first surfactant to coenzyme Q10 is typically from about 0.6:1 to about 0.85:1, more typically from about 0.7:1 to about 0.8:1.

3. Emulsifying Surfactants

In addition to the solubilizing surfactant, a second emulsifying surfactant with hydrophilic-lipophilic balance lower than the solubilizing surfactant is typically also employed. The addition of an emulsifying surfactant promotes a reduction in the size of the dispersed coenzyme Q10 organic phase upon mixing with an aqueous solution. When the resulting mixture is placed under high shear, the result is the production of an extremely fine suspension of coenzyme Q10 in an intimate mixture with at least one surfactant, and preferably with both the solubilizing and emulsifying surfactants.

In the methods of the present invention, the emulsifying surfactant may be added to the aqueous phase before, during, or after combining the aqueous phase and the coenzyme Q10-containing organic phase. In some embodiments, the emulsifying surfactant is added to the aqueous phase before combination with the coenzyme Q10 organic phase, thereby promoting the formation of an oil-in-water emulsion of very fine drops. Again with reference to FIG. 1, second surfactant 9 is incorporated as a component of aqueous phase 11. Alternatively, and as optionally shown in FIG. 1 via dashed lines, second surfactant 9 may be incorporated as a component of the coenzyme Q10-containing organic phase.

Suitable emulsifying (second) surfactants generally have a hydrophilic-lipophilic balance (HLB) that is low enough to promote a reduction in size of the dispersed coenzyme Q10 droplets upon mixing with water. Typically, the HLB of the emulsifying surfactant is less than about 8, more typically less than about 7, more typically less than about 6.5, more typically less than about 6, more typically less than about 5.5, more typically less than about 5, more typically less than about 4.5, and still more typically less than about 4.

Non-limiting examples of suitable emulsifying surfactants include phosphatidyl choline, phosphatidyl serine, phosphatidyl inositol, phosphatidylglycerol, dioleoyl phosphatidylcholine, dioleoylphosphatidylglycerol, dimyristoylphosphatidylcholine, dipalmitoylphosphatidylcholine, phosphatidylethalolamines, phosphatidylserines, sphingomyelins, poly gylcerol esters, ethoxylated castor oils, phospholipids derived from soy, or phospholipids derived from milk-fat globule membrane. In some preferred embodiments, the emulsifying surfactant is lecithin. In some preferred embodiments, the emulsifying surfactant is phosphatidyl choline. In some embodiments, a combination of emulsifying surfactants may be used. In various preferred embodiments, the emulsifying surfactant comprises a phosphatidyl choline component exhibiting a relatively high phosphatidyl choline content (e.g., greater than 90 wt. % or greater than 95 wt. %). Such a suitable component includes commercially available PHOSPHOLIPON 90G.

In various embodiments, the HLB of the solubilizing surfactant(s) is between 8 and about 14 (e.g., from about 9 to about 12) while the HLB of the emulsifying surfactant(s) is from about 4 to 8 (e.g., from about 7 to 8 or from about 7 to about 7.5).

Typically, the weight ratio of the solubilizing surfactant to the emulsifying surfactant is from about 1:1 to about 10:1, from about 2:1 to about 7:1, or from about 4:1 to about 6:1. Typically, the weight ratio of coenzyme Q10 to the emulsifying surfactant is from about 2:1 to about 15:1, from about 4:1 to about 10:1, or from about 5:1 to about 8:1.

Typically in accordance with the foregoing, coenzyme Q10 constitutes from about 25 to about 50 wt. % of the organic phase, more typically from about 30 to about 40 wt. % of the organic phase and, still more typically, from about 35 to about 40 wt. % of the organic phase.

Further in accordance with the foregoing, the organic solvent typically constitutes from about 20 to about 60 wt. % of the organic phase, more typically from about 25 to about 40 wt. % of the organic phase and, still more typically, from about 30 to about 40 wt. % of the organic phase.

The solubilizing surfactant typically constitutes from about 10 to about 40 wt. % of the organic phase, more typically from about 20 to about 35 wt. % of the organic phase and, still more typically, from about 25 to about 30 wt. % of the organic phase.

The emulsifying surfactant constitutes from about 1 to about 15 wt. % of the organic phase, more typically from about 2 to about 12 wt. % of the organic phase and, still more typically, from about 4 to about 8 wt. % (e.g., from about 4 to about 6 wt. %) of the organic phase.

4. Encapsulating Medium

In a further step of the method of the present invention, a water-soluble encapsulator is mixed with water to form an aqueous phase comprising the encapsulating medium.

The encapsulating medium or encapsulator may comprise any polysaccharide or polymeric binder composition that is soluble in water and suitable for spray- or freeze-drying. Thus, non-limiting examples of suitable encapsulating media include starches, cellulose, chitin or chitosan, and arabinoxylans. In some preferred embodiments, a chemically modified starch is employed. Non-limiting examples of chemically modified starches include dextrins, succinylated starches, alkaline-modified starches, bleached starches, oxidized starches, enzyme-treated starches, distarch phosphates, acetylated starches, hydroxypropyl starches, hydroxyethyl starches, octenyl succinic anhydride starch, cationic starches, carboxymethylated starches, and combinations thereof. Preferred chemically modified starches include maltodextrin and succinylated starches. An exemplary suitable chemically modified starch is CAPSUL, commercially available from National Starch, Inc.

Suitable polymeric binder compositions include methylcellulose, hydroxypropyl methylcellulose, hydroxyethylcellulose, hydroxypropylethylcellulose, sodium carboxymethylcellulose, crystalline cellulose, ethylcellulose, polyvinylpyrrolidone, pectin, gum arabic, gum tragacanth, acacia, gelatin, or any other polymeric matrix-forming preparation known to those skilled in the art. In preferred embodiments, hydroxylpropyl methylcellulose or a cold water soluble starch is typically selected. In more preferred embodiments, the starch is typically a succinylated starch. Further, in some embodiments, a combination of encapsulators may also be used.

The encapsulating medium should be mixed with a sufficient amount of water such that the encapsulating medium becomes fully dissolved. Generally, the encapsulating medium, or encapsulator constitutes at least about 1 wt. %, at least about 2 wt. %, at least about 4 wt. %, or at least about 5 wt. % of the aqueous phase. In various embodiments, the encapsulator constitutes from about 15 to about 70 wt. %, from about 20 to about 50 wt. %, or from about 25 to about 30 wt. % of the aqueous phase. In various other embodiments in which the aqueous phase is more dilute, the encapsulator typically constitutes from about 1 to about 25 wt. %, from about 2 to about 20 wt. %, or from about 5 to about 10 wt. % of the aqueous phase. For example, in various preferred embodiments in which the encapsulator comprises starch, the aqueous phase initially comprises a solution having about 20% starch by weight, which is later diluted to about 5% starch by weight.

The weight ratio of the encapsulating medium to the solubilizing surfactant is typically from about 0.5:1 to about 4:1, more typically from about 1:1 to about 2:1, still more typically from about 1:1 to about 1.5:1, and most typically about 1.25:1. Typically, the weight ratio of the encapsulator to emulsifying surfactant is from about 2:1 to about 15:1, more typically from about 4:1 to about 10:1 and, still more typically, from about 5:1 to about 8:1.

5. pH Adjustment

Optionally, as shown in FIG. 1, in a further step of the method of the present invention, an acid 17 may be added to the aqueous solution. Typically, the acid is an organic acid, which is more typically selected from the group consisting of citric acid, succinic acid, and ascorbic acid. In preferred embodiments, the organic acid is typically ascorbic acid. When added to the aqueous solution, the acid is believed to provide an increased rate of dissolution of coenzyme Q10, and further increases the total dissolution that can be obtained in aqueous solution.

Also optionally, in a further step of the method of the present invention, a base may be added to the aqueous solution. Particularly where the optional step of adding an organic acid has been performed, it may be desirable to alter the pH of the aqueous solution to a more preferred range. The pH of the aqueous solution is typically maintained between 4 and 10, more typically between 5 and 9, more typically between 6 and 8, and most typically at about 7. Generally, any alkaline substance may be used for this purpose, provided that it does not substantially alter the solubility, bioavailability, or other characteristics of coenzyme Q10 or other active ingredients. A non-limiting list of suitable bases for this purpose includes sodium bicarbonate, sodium carbonate, and sodium hydroxide.

6. Mixing & Agitation

Again with reference to FIG. 1, in a further step of the method of the present invention, organic phase 5 is mixed with aqueous phase 11 using suitable apparatus 33. When the two phases are mixed, the result is an oil-in-water emulsion in which the coenzyme Q10 organic phase forms a microdispersion throughout the encapsulating medium. The microdispersion resists coalescence, and maintains discrete microdroplets of coenzyme Q10 that are associated with one or more surfactants.

In a preferred embodiment, the organic phase and aqueous phase are combined by mixing under agitation that provides moderate to high shear. The agitation may be conducted using any conventional mixing apparatus known in the art. Non-limiting examples of possible mixing apparatus include mechanical agitators, static agitators, rotating tank agitators and high pressure homogenizers, and the mixing may occur as part of a batch, semi-batch, or continuous process. The mixing typically is sufficient to produce a generally uniform emulsion of fine particles of coenzyme Q10 associated with one or more surfactants dispersed throughout the aqueous medium. Preferably, the fine particles of coenzyme Q10 associated with surfactant(s) are isotropically dispersed throughout the aqueous medium.

The discrete coenzyme Q10 microdroplets typically have a droplet size distribution such that at least about 50%, at least about 60%, at least about 70%, at least about 80%, or at least about 90% by weight of the coenzyme Q10 microdroplets have a largest dimension of less than about 20 μm, less than about 15 μm, less than about 10 μm, less than about 5 μm, or less than about 3 μm.

More typically, the discrete coenzyme Q10 microdroplets have a droplet size distribution such that at least about 50%, at least about 60%, at least about 70%, at least about 80%, or at least about 90% by weight of the microdroplets have a largest dimension of from about 0.5 to about 15 μm, from about 1 to about 8 μm, or from about 1 to about 4 μm.

On a number basis, the discrete microdroplets of coenzyme Q10 typically have a droplet size distribution such that at least about 1%, at least about 5%, at least about 10%, at least about 20%, at least about 30%, at least about 40%, or at least about 45% by number basis of the coenzyme Q10 microdroplets have a largest dimension of less than about 0.5 μm.

More typically, the discrete microdroplets of coenzyme Q10 have a droplet size distribution such that at least about 50%, at least about 60%, at least about 70%, at least about 80%, or at least about 90% by number basis of the coenzyme Q10 microdroplets have a largest dimension of less than about 1 μm.

In terms of volume weighted mean particle size, the discrete microdroplets of coenzyme Q10 typically have a droplet size distribution such that the volume weighted mean droplet size is from about 0.5 to about 5 μm, from about 1 to about 2.5 µm, from about 1 to about 2 µm, from about 1.2 to about 1.8 µm, or about 1.6 µm.

During its preparation and prior to its combination with the aqueous phase, the organic phase is typically heated and maintained at a temperature of from about 55° C. to about 75° C. and, more typically, from about 60° C. to about 70° C. (e.g., about 65° C.). The temperature of the aqueous phase combined with the organic phase is typically from about 45° C. to about 65° C. and, more typically, from about 50° C. to about 60° C. (e.g., about 55° C.). As noted, when combined under agitation, the organic phase and aqueous phase form an emulsion. The temperature of this emulsion is typically from about 70° C. to about 85° C. and, more typically, from about 75° C. to about 80° C.

7. Drying Process

In a further step of the method of the present invention, the microdispersion described above is dried to form solid particles using a known evaporative process. Non-limiting examples of known evaporative processes include spray drying, freeze drying, and fluid bed drying. The drying step typically comprises spray drying.

During the drying process, the solvent is substantially evaporated. The coenzyme Q10 and associated surfactant(s) are co-precipitated, remaining dispersed within the encapsulating medium. This results in the formation of a solid matrix, in which the microdispersion formed during the previous step remains essentially intact. In the spray drying process, the inlet temperature of the spray dryer is typically at least about 160° C., or at least about 170° C. (e.g., about 180° C.). During the spray drying operation, water is removed from the aqueous phase and the solid matrix particles are typically formed at a temperature of from about 60° C. to about 75° C. and, more typically, from about 65° C. to about 70° C. The outlet temperature of the spray dryer is typically from about 70° C. to about 90° C. (e.g., about 80° C.)

Upon completion of the drying process, the solidified microdroplets of co-precipitated coenzyme Q10 and associated surfactants are generally believed to be in an amorphous, non-crystalline form. In particular, it is currently believed that a significant fraction of the coenzyme Q10 in the final dried product is in an amorphous form (e.g., at least about 70 wt. %, at least about 80 wt. %, at least about 90 wt. %, or higher, such as for example at least about 95 wt. %). It is currently believed that formation of this significant fraction of amorphous coenzyme Q10 is provided by the processing temperatures discussed above (e.g., the temperature of the organic phase and the temperature of the spray drying operation). The melting point of coenzyme Q10 is 49° C. Since these processing temperatures are above the melting point of coenzyme Q10, they promote formation of coenzyme Q10 in an amorphous form in the final product. In addition, spray drying operations are generally known to one skilled in the art to alter the morphology of crystalline material to form amorphous material.

The solid colloidal particles including CoQ10-containing microparticulates typically have a particle size distribution such that at least about 50%, at least about 60%, at least about 70%, at least about 80%, or at least about 90% by weight of the solid particles have a largest dimension of from about 1 to about 100 µm, more typically from about 2 to about 50 µm, more typically from about 5 to about 30 µm, more typically from about 6 to about 25 µm, and more typically from about 8 to about 15 µm in diameter.

Figure 2:
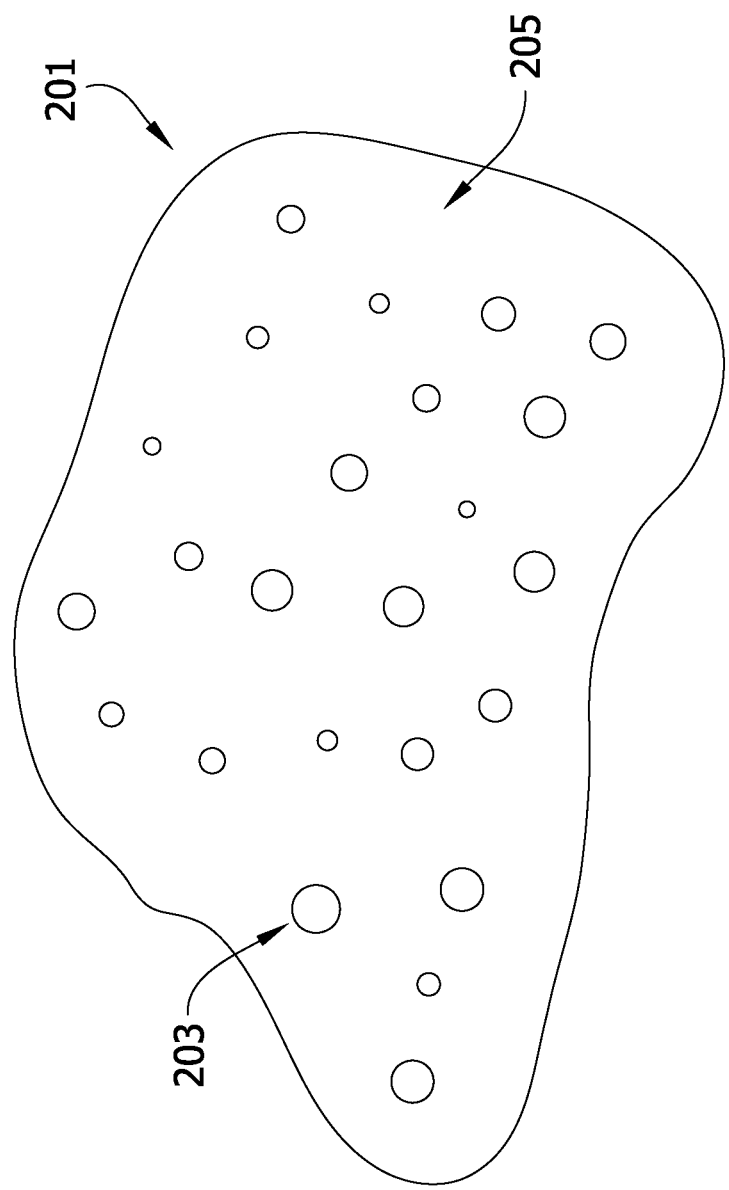
FIG. 2 is a representation of the internal structure of the solid particles comprising coenzyme Q10 that constitute one embodiment of the present invention.

FIG. 2 provides a representation of the internal structure of a preferred embodiment of the solid colloidal particles 201, in which microparticulates of coenzyme Q10 associated with surfactant(s) 203 are dispersed throughout the encapsulating medium 205. The dispersion of microparticulates throughout the encapsulating medium is typically isotropic in nature.

C. Particulate Compositions

The present invention further provides for novel particulate compositions comprising coenzyme Q10 as an active ingredient. In particular, the invention provides for a solid particulate composition comprising coenzyme Q10, at least one surfactant (e.g., a combination of at least one solubilizing surfactant and at least one emulsifying surfactant), and an encapsulating medium. In some embodiments, the solid particles further comprise one or more residual components.

The structure of the solid particles is novel, and provides for increased stability, dispersibility, solubility and/or bioavailability of the coenzyme Q10 active ingredient. In particular, each of the solid particles itself comprises discrete "microparticulates" of coenzyme Q10, associated with surfactant(s), which are dispersed throughout a solid matrix comprising the encapsulating medium. These amorphous, non-crystalline microparticulates are easily released from the water-soluble encapsulator upon contact with intestinal fluids, resulting in increased absorption through the intestinal wall.

The solid particles typically have a particle size distribution as set forth above as provided by drying of the aqueous mixture comprising CoQ10-containing microdroplets.

The discrete coenzyme Q10 microparticulates typically have a particle size distribution such that at least about 50%, at least about 60%, at least about 70%, at least about 80%, or at least about 90% by weight of the coenzyme Q10 microparticulates have a largest dimension of less than about 20 µm, less than about 15 µm, less than about 10 µm, less than about 5 µm, less than about 3 µm, less than about 2 µm, or less than about 1 µm.

More typically, the discrete coenzyme Q10 microparticulates have a particle size distribution such that at least about 50%, at least about 60%, at least about 70%, at least about 80%, or at least about 90% by weight of the microparticulates have a largest dimension of from about 0.5 to about 15 µm, from about 1 to about 8 µm, or from about 1 to about 4 µm.

On a number basis, the discrete microparticulates of coenzyme Q10 typically have a particle size distribution such that at least about 1%, at least about 5%, at least about 10%, at least about 20%, at least about 30%, at least about 40%, or at least about 45% by number basis of the coenzyme Q10 microparticulates have a largest dimension of less than about 0.5 µm.

More typically, the discrete microparticulates of coenzyme Q10 have a droplet size distribution such that at least about 50%, at least about 60%, at least about 70%, at least about 80%, or at least about 90% by number basis of the coenzyme Q10 microparticulates have a largest dimension of less than about 1 µm.

In terms of volume weighted mean particle size, the discrete microparticulates of coenzyme Q10 typically have a particle size distribution such that the volume weighted mean particle size is from about 0.5 to about 5 µm, from about 1 to about 2.5 µm, from about 1 to about 2 µm, from about 1.2 to about 1.8 µm, or about 1.6 µm.

1. Coenzyme Q10

In the compositions of the present invention, coenzyme Q10 is present in a therapeutically effective amount. The therapeutically effective amount will vary in accordance with the intended application and the form of delivery, and may depend upon factors including the age, medical history, and medical condition of the particular patient.

With respect to the solid particles of the present invention, coenzyme Q10 will typically comprise from about 10% to about 50% by weight of the solid particulate composition. In preferred embodiments, coenzyme Q10 comprises from about 15% to about 45%, more typically from about 25% to about 40%, and most typically from about 30% to about 35% by weight of the solid particulate composition.

In some embodiments, a significant amount of the coenzyme Q10 is present in an amorphous, non-crystalline state. More typically, at least about 50%, at least about 60%, at least about 70%, at least about 80%, or at least about 90% of the coenzyme Q10 is present in an amorphous state.

2. Encapsulating Medium

The encapsulating medium typically comprises from about 10% to about 50% by weight of the solid particles. In more preferred embodiments, the encapsulating medium comprises from about 20% to about 35%, more typically from about 20% to about 30%, and most typically about 25% by weight of the solid particulate composition.

3. Surfactants

The composition of the present invention further comprises a combination of at least one surfactant, preferably at least one solubilizing surfactant and at least one emulsifying surfactant.

The solubilizing surfactant typically constitutes from about 5% to about 40% by weight of the solid particulate composition. In preferred embodiments, the solubilizing surfactant constitutes from about 15% to about 30%, more typically from about 20% to about 30%, and most typically about 25% by weight of the solid particulate composition.

Additionally, the weight ratio of encapsulating medium to the solubilizing surfactant is typically from about 0.5:1 to about 4:1, more typically from about 1:1 to about 2:1, still more typically from about 1:1 to about 1.5:1, and more typically about 1.25:1.

The emulsifying surfactant typically constitutes from about 0.1% to about 25% by weight of the solid particulate composition. In preferred embodiments, the emulsifying surfactant constitutes from about 1% to about 10%, more typically from about 2% to about 8%, and most typically from about 3% to about 6% by weight of the solid particulate composition.

Additionally, the weight ratio of encapsulating medium to the emulsifying surfactant is typically from about 2:1 to about 15:1, more typically from about 2:1 to about 15:1, still more typically from about 4:1 to about 10:1, and more typically about 5:1 to about 8:1.

4. Residual Components

In some embodiments, the compositions of the present invention may further comprise one or more residual components remaining from the method of preparation described in detail above.

For example, in some embodiments, the composition further comprises one or more solvents. Spray-drying is a preferred method of forming the solid particles of the present invention, and typically results in a substantial portion of the solvent being evaporated. In some embodiments, the solvent is evaporated completely, such that no significant amount of solvent remains in the solid particles. In other embodiments, however, a measurable amount of solvent may remain in the final product. For example, where the solvent is hexanol, the concentration of hexanol in the dried product is typically less than about 200 ppm. The concentration of solvent in the solid particulate composition is typically less than about 1000 ppm, more typically less than about 500 ppm, more typically less than about 200 ppm, more typically less than about 100 ppm, still more typically less than about 50 ppm, still more typically less than about 25 ppm, and still more typically less than about 20 ppm.

In some embodiments, the compositions of the present invention may further comprise one or more pH adjustment agents.

For example, in some embodiments, the compositions of the present invention may further comprise an acid. The acid is typically an organic acid, and more typically is ascorbic acid. In those embodiments of the present invention that comprise an acid, the acid typically comprises from about 1% to about 25% by weight of the solid particulate composition, more typically from about 2% to about 15% by weight, more typically from about 4% to about 12% by weight, and still more typically from about 8% to about 10% by weight of the solid particulate composition.

In some embodiments of the present invention, the composition further comprises a base. A non-limiting example of a preferred base is sodium bicarbonate. In those embodiments of the present invention that comprise a base, the base typically comprises less than about 5% by weight of the solid particulate composition, more typically less than about 2%, more typically less than about 1%, and still more typically less than about 0.5% by weight of the solid particulate composition. In accordance with such embodiments, the base typically constitutes at least about 0.05 wt % of the composition.

5. Solubility and Bioavailability

As noted, particulate CoQ10 compositions of the present invention are currently believed to exhibit improved release rates (i.e., rate of solubility) and overall or total solubility as compared to conventional and commercially-available CoQ10 products. Example 3 provides absorbance results of dissolution testing for particulate (i.e., powder) CoQ10 formulations prepared in accordance with the present invention. As described in Example 3 and shown in FIG. 3, the results of dissolution testing for CoQ10 products of the present invention indicate an increased rate of release (i.e., increased rate of solubility) and also exhibit greater overall or total solubility as compared to a sample including a conventional CoQ10 product. This greater solubility is currently believed to be an indication that the CoQ10 products of the present invention provide improved bioavailability when incorporated into a suitable dosage form.

In addition, Examples 8 and 9 present pharmacokinetic data for test compositions comprising the CoQ10 formulations of the present invention. This testing was generally conducted by oral administration of a capsule dosage form including 60 mg coenzyme Q10 and testing of blood plasma levels after administration (e.g., at various time intervals).

Advantageously, the compositions of the present invention have been observed to provide enhanced bioavailability as evidenced by blood plasma concentration at various time intervals following administration.

For example, in various embodiments, the total exposure of coenzyme Q10, as determined by the area under the plasma concentration vs. time curve at a particular point following administration of a dose containing about 60 mg coenzyme Q10, one or more of the following levels of exposure at the prescribed time interval is achieved:

(i) at 4 hours following oral administration of a dose containing about 60 mg of coenzyme Q10, the area under the plasma concentration vs. time curve is at least about 0.15 mg·h/L, at least about 0.175 mg·h/L, at least about 0.2 mg·h/L, at least about 0.225 mg·h/L, or at least about 0.25 mg·h/L; and/or (ii) at 6 hours following oral administration of a dose containing about 60 mg of coenzyme Q10, the area under the plasma concentration vs. time curve is at least about 0.5 mg·h/L, at least about 0.6 mg·h/L, at least about 0.65 mg·h/L, at least about 0.7 mg·h/L, or at least about 0.75 mg·h/L; and/or (iii) at 8 hours following oral administration of a dose containing about 60 mg of coenzyme Q10, the area under the plasma concentration vs. time curve is at least about 1 mg·h/L, at least about 1.1 mg·h/L, at least about 1.2 mg·h/L, at least about 1.3 mg·h/L, or at least about 1.4 mg·h/L; and/or (iv) at 10 hours following oral administration of a dose containing about 60 mg of coenzyme Q10, the area under the plasma concentration vs. time curve is at least about 1.5 mg·h/L, at least about 1.6 mg·h/L, at least about 1.7 mg·h/L, or at least about 1.8 mg·h/L; and/or (v) at 12 hours following oral administration of a dose containing about 60 mg of coenzyme Q10, the area under the plasma concentration vs. time curve is at least about 2.0 mg·h/L, at least about 2.1 mg·h/L or at least about 2.2 mg·h/L; and/or (vi) at 14 hours following oral administration of a dose containing about 60 mg of coenzyme Q10, the area under the plasma concentration vs. time curve is at least about 2.5 mg·h/L.

Further advantageously, CoQ10 compositions of the present invention have been observed to provide a maximum plasma concentration in a relatively rapid period of time following administration. For example, in accordance with various compositions and formulations of the present invention, the maximum plasma concentration ($C_{max}$), as determined by the maximum concentration value reached on the plasma concentration vs. time curve, is achieved in less than 7 hours or in less than about 6 hours following oral administration of a dose containing about 60 mg coenzyme Q10.

Further in accordance with these and various other embodiments, the time of the first observed rise in plasma concentration from 0 mg/L ($t_{lag}$) occurs relatively rapidly following oral administration of a dose containing about 60 mg coenzyme Q10. For example, in various embodiments, $t_{lag}$ occurs in less than about 3 hours, less than about 2 hours, or less than about 1 hour following administration.

Additionally or alternatively, compositions of the present invention have been observed to provide total exposures (areas under the curve, or AUC) that are at relatively high levels and achieved over relatively long periods of time. For example, in various embodiments, the total exposure (AUC), as determined by the area under the plasma concentration vs. time curve at 24 hours following oral administration of a does containing about 60 mg coenzyme Q10 is at least about 2 mg·h/L, at least about 3 mg·h/L, at least about 4 mg·h/L, or a least about 4.5 mg·h/L. Accordingly, in this manner, compositions of the present invention provide release of the coenzyme Q10 at levels sufficient for treatment for a relatively long period of time. As compared to currently available commercial products, the compositions of the present invention provide elevated CoQ10 blood levels for a longer period of time after oral administration. As a result, the present compositions should provide benefits for individuals taking coenzyme Q10 as part of a medium- or long-term therapy.

D. Dosage Forms

The compositions of the present invention may be formulated into any dosage form suitable for administration to a human or other mammal. The dosage form may generally comprise any biologically acceptable excipient known in the art. Generally, preparation of any of the dosage forms described herein may be accomplished by one skilled in the art using established methods of preparation.

A primary advantage of the present invention, as compared to the prior art, is that the solid particles of the present invention may be readily incorporated into a solid tablet dosage form. Tablets are a preferred form of administration, as they are generally less expensive to manufacture and exhibit a longer shelf life than capsules or liquid-based formulations. The availability of high-speed tablet presses provides a further advantage over other dosage forms, which are typically more difficult to produce.

An additional advantage of the present invention is that, due to the increased bioavailability of the coenzyme Q10, beneficial effects may be achieved with lower doses of CoQ10 relative to the prior art. For example, where the intended use of the coenzyme Q10 is for dietary supplementation, the amount will typically range from about 5 mg to about 1000 mg per dosage. More typically, the amount of coenzyme Q10 is from about 10 mg to about 250 mg per dosage, more typically from about 15 mg to about 200 mg per dosage, and more typically from about 20 mg to about 100 mg per dosage.

1. Excipients and Preparation of Dosage Forms

In some embodiments, the compositions of the present invention are formulated into a solid oral dosage form. Non-limiting examples of solid oral dosage forms include tablets, soft chewable tablets, hard or soft gelatin capsules, pills, pellets, and troches and/or lozenges.

Excipients typically used in the preparation of solid oral dosage forms include components such as binders, fillers and diluents, disintegrators, surfactants, lubricants, fluidity accelerators, sweetening agents, flavorants, colorants, and perfumes. Various other materials may be also present as coatings or to otherwise modify the physical form of the dosage unit. For example, tablets, pills or capsules may be coated with shellac, sugar, or both.

Non-limiting examples of binders include starch, dextrin, gum arabic, gum tragacanth, acacia, gelatin, hydroxypropyl starch, methylcellulose, sodium carboxymethylcellulose, hydroxypropylcellulose, crystalline cellulose, ethylcellulose, and/or polyvinylpyrrolidone. Non-limiting examples of fillers and diluents include dicalcium phosphate, lactose, sucrose, glucose, mannitol, sorbitol, calcium carbonate, and magnesium stearate. Where the dosage form is a capsule, the filler or diluent typically further includes a vegetable oil. Non-limiting examples of disintegrators include corn starch, hydroxypropyl starch, sodium carboxymethylcellulose, cross-linked sodium carboxymethylcellulose, calcium carboxymethylcellulose, carboxymethylcellulose, and hydroxypropylcellulose. Non-limiting examples of surfactants include sodium lauryl sulfate, soybean lecithin, sucrose fatty acid ester, and POLYSORBATE 80. Non-limiting examples of lubricants include talc, waxes, hydrogenated vegetable oils, sucrose fatty acid ester, magnesium stearate, calcium stearate, aluminum stearate, and polyethylene glycol. Non-limiting examples of fluidity accelerators include light anhydrous silicic acid, dry aluminum hydroxide gel, synthetic aluminum silicate, and magnesium silicate. Non-limiting examples of sweetening agents include sucrose, lactose or saccharin. Non-limiting examples of flavorants include peppermint, oil of wintergreen, or natural and artificial fruit flavorings.

Tablets according to the present invention may be prepared using any conventional tabletting methods known in the art, including by granulation, compression, or molding methods. In a preferred embodiment, the tablet has a hardness of at least about 5 kilopascals (kPa).

The compositions of the present invention may also be formulated as liquid compositions, either for oral ingestion or as an injectable medium. Non-limiting examples of liquid compositions suitable for oral ingestion include elixirs, solutions, suspensions and syrups.

The compositions of the present invention may also be formulated as a granulation. In some embodiments, the granulation may be ingested directly. More typically, the granulation is incorporated into food or drink prior to ingestion. To provide a non-limiting example, sprinkles are a type of food product which may be prepared from a granulation prepared in accordance with the present invention. Similarly, the compositions of the present invention may also be formulated as a powder for use in a powdered drink mix.

The compositions of the present invention may also be incorporated into creams, ointments or gels. Typically, the cream or ointment is topically applied to the skin, gingiva, mucosal tissue, or other area that would obtain benefit from coenzyme Q10 supplementation. In some embodiments, the cream is used to treat and/or prevent the formation of wrinkles in the skin, particularly on or near the face. In other embodiments, an ointment or gel is formulated for application to the gingiva as a treatment for gingivitis. Ointments are typically prepared by adding a base component which is used according to a conventional method. Typically, such an ointment composition will contain about 0.5% to about 30% by weight of coenzyme Q10.

In still further embodiments, the compositions of the present invention may also be formulated as thin films. Thin film formulations typically comprise a dissolving film or a thin drug strip, wherein the composition is absorbed through the mouth.

With respect to any of the above dosage forms, the compositions of the present invention may be incorporated into sustained-release preparations and formulations. Using methods known in the art, the compositions may be made into a rapid release preparation, suspended release preparation, or a slow release preparation.

2. Secondary Bioactive Agents

In some embodiments, the particulate composition of the present invention further comprises one or more secondary bioactive agents. The secondary bioactive agents preferably provide a therapeutic effect when ingested by a mammal.

In some embodiments, the additional therapeutic agents may be combined with the coenzyme Q10 organic phase during the preparation of the present invention. In these embodiments, it is preferred that the additional therapeutic agents are insoluble in water, as the method of the present invention could be used to simultaneously increase the bioavailability of all the active ingredients. In other embodiments, the solid particles comprising coenzyme Q10 are combined with the additional therapeutic agents during the preparation of an appropriate pharmaceutical dosage form. In either case, it is preferred that the additional therapeutic agents are chemically stable when included in the composition, and do not reduce the bioavailability or impair the uptake of coenzyme Q10 in vivo.

Generally, the additional therapeutic agents may comprise any substance that provides a beneficial effect to humans or other mammals. In preferred embodiments, the additional therapeutic agent provides an effect that is compatible with, and does not interfere with, the beneficial effects provided by coenzyme Q10 supplementation. Nutraceuticals, vitamins, and minerals are particularly preferred for this purpose.

Non-limiting examples of neutraceuticals include α-carotene, β-carotene, lycopene, lutein, riboflavin, resveratrol, retinol, and omega-3 fatty acids, and/or mixtures thereof.

Non-limiting examples of vitamins include retinol, retinal, carotenoids, thiamine, riboflavin, niacin, niacinamide, pantothenic acid, pyridoxine, pyridoxamine, pyridoxal, biotin, folic acid, folinic acid, cyanocobalamin, hydroxycobalamin, methylcobalamin, ascorbic acid, ergocalciferol, cholecalciferol, tocopherols, tocotrienols, phylloquinone, menaquinones, and/or mixtures thereof.

Non-limiting examples of minerals include potassium, chlorine, sodium, calcium, phosphorus, magnesium, zinc, iron, manganese, copper, iodine, selenium, chromium, molybdenum, and/or mixtures thereof.

In some embodiments, the solid particulate coenzyme Q10 composition is incorporated into a multivitamin comprising a plurality of other vitamins, minerals and/or nutraceuticals.

In some embodiments, the additional therapeutic agents may comprise substances with medicinal properties. In preferred embodiments, the medicinal substance has a utility in treating diseases or conditions for which coenzyme Q10 supplementation may provide benefit. Non-limiting examples of diseases and/or conditions that may benefit from coenzyme Q10 supplementation along with a therapeutic agent include neurogenerative diseases, cardiovascular disease, stroke, cardiac arrest, high blood pressure, periodontal disease, migraine headaches, cancer, radiation injury, and mitochondrial disorders that inhibit the cellular production of coenzyme Q10. Non-limiting examples of specific neurodegenerative diseases that may benefit from coenzyme Q10 supplementation include muscular dystrophy, Parkinson's disease, Huntington's disease, and amyotrophic lateral sclerosis (ALS).

In a particularly preferred embodiment, the compositions of the present invention are advantageously taken as part of a regimen that also includes statins.

E. Methods of Administration

The present invention is further directed to methods comprising the administration of a composition comprising coenzyme Q10 to a mammal. Typically, the mammal is a human. The therapeutically effective dose will vary in accordance with the intended application, and may depend upon factors including the age, medical history, and medical condition of the particular patient. In some embodiments, the patient has a disease and/or condition that may benefit from coenzyme Q10 supplementation.

For example, where the intended use of the coenzyme Q10 is for dietary supplementation, the amount of active ingredient will typically range from 5 mg to 1000 mg per dosage. More typically, the amount of coenzyme Q10 is from about 10 to 250 mg per dosage, more typically from about 15 to 200 mg per dosage, and more typically from about 20 to 100 mg per dosage.

Having described the invention in detail, it will be apparent that modifications and variations are possible without departing from the scope of the invention defined in the appended claims.

EXAMPLES

The following non-limiting examples are provided to further illustrate the present invention.

Example 1

Water (380.0 g) was introduced into a 500 ml Pyrex beaker, set on a hotplate/mixer and heated to 80° C. CAP- SUL succinylated starch (25.0 g) was added and mixed for 1 hour. The resulting mixture was cooled to 50° C., and sodium bicarbonate (0.2 g) was added to partially neutralize the mixture.

GELUCIRE 44/14 (15.8 g) was introduced into a 100 ml Pyrex beaker, set on a hotplate/mixer and heated to 60° C. Coenzyme Q10 (21.8 g) was added to the GELUCIRE and stirred until a clear solution was achieved. Hexanol (20.0 g) was then added to the coenzyme Q10-GELUCIRE mixture and stirred for 5 minutes.

The aqueous starch solution was agitated with a Ross homogenizer. PHOSPHOLIPON 90G (3.3 g), a product including at least 94% phosphatidyl choline, was added to the starch solution and mixed until dissolved. The coenzyme Q10-GELUCIRE mixture was then slowly added to the aqueous starch solution, and was mixed on high for 20 minutes. The resulting mixture was then spray dried using a NIRO MOBILE MINOR spray dryer, producing a yellow orange powder.

Example 2

Water (380.0 g) was introduced into a 500 ml Pyrex beaker, set on a hotplate/mixer and heated to 80° C. CAP-SUL succinylated starch (25.0 g) was added and mixed for 1 hour. The resulting mixture was cooled to 50° C. Ascorbic acid (6.25 g) and sodium bicarbonate (0.2 g) were then added to the aqueous starch solution.

GELUCIRE 44/14 (15.8 g) was introduced into a 100 ml Pyrex beaker, set on a hotplate/mixer and heated to 60° C. Coenzyme Q10 (21.8 g) was added to the GELUCIRE and stirred until a clear solution was achieved. Hexanol (20.0 g) was then added to the coenzyme Q10-GELUCIRE mixture and stirred for 5 minutes.

The aqueous starch solution was agitated with a Ross homogenizer. PHOSPHOLIPON 90G (3.3 g), a product including at least 94% phosphatidyl choline, was added to the starch solution and mixed until dissolved. The coenzyme Q10-GELUCIRE mixture was then slowly added to the aqueous starch solution, and was mixed on high for 20 minutes. The resulting mixture was then spray dried using a NIRO MOBILE MINOR spray dryer, producing a yellow orange powder.

Example 3

Dissolution Test

One gram of each powder formulation, prepared as described in Examples 1 and 2, was weighed into a suitable vessel for mixing. Maltodextrin (49.000 g) was added to each mixing vessel, and each mixture was blended to uniformity. A sample of the maltodextrin blend (0.500 g) of each powder formulation was added to deionized water (0.900 L) containing 0.1% Polysorbate 80, which was preheated to 37° C. The resulting solution was placed in an FDA Apparatus II vessel with paddles, and stirring was set at 50 revolutions per minute (rpm). Samples were taken by removal of 3 mL, and each sample was filtered with a 1 micron syringe filter. An initial sample was taken after 5 minutes, with further samples taken at prescribed 15 minute intervals based upon the starting time. The absorbance for each sample was measured in a 1 cm cell at 275 nm, using a VARIAN UV spectrophotometer. The same volume of 0.1% polysorbate 80 was returned to the vessel after each sample.

A reference sample was formulated using the following procedure. Maltodextrin (49.67 g) was introduced into a blender. KANEKA QH coenzyme Q10 (0.33 g) was added to the blender. The mixture was blended for 20 minutes until a uniform blend was achieved. Samples of the blended mixture (500 mg) were used as a reference for the dissolution test. Absorbance for samples of the reference mixture was measured as described above.

Figure 3:
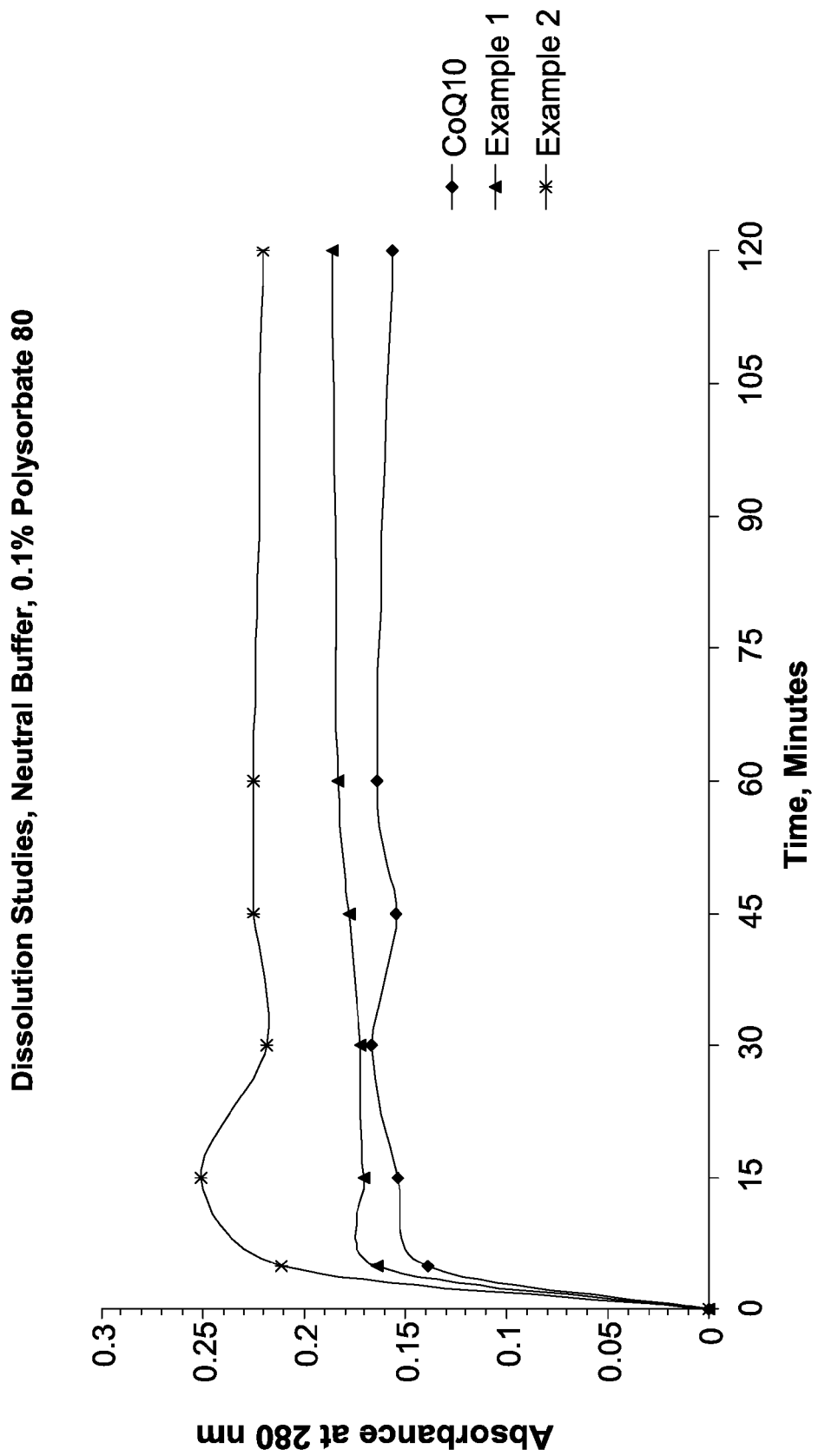
FIG. 3 is a representation of the dissolution data that was obtained pursuant to the procedure described in Example 3.

The absorbance results for the samples of the powders of Examples 1 and 2 and the reference sample are shown in FIG. 3. As shown in FIG. 3, beginning at a sample time of about 5 minutes and continuing up to a sample time of 120 minutes, the samples of the powder formulations of Examples 1 and 2 exhibit greater absorbance than the reference sample containing the commercially-available CoQ10 product. This higher absorbance indicates greater solubility of the powder samples of Examples 1 and 2 as compared to the commercially-available CoQ10 product. In particular, the increased absorbance at a sample time of 5 minutes indicates an increased rate of solubility for the CoQ10 products of the present invention and the increased absorbance continuing up to a sample time of 120 minutes indicates an increased overall or total solubility for the CoQ10 products of the present invention. As detailed elsewhere herein, the higher solubility of the CoQ10 formulations of the present invention as exhibited in this Example is currently believed to provide improved bioavailability of CoQ10 when the particulate compositions of the present invention (e.g., the powders of Examples 1 and 2) are incorporated into a suitable dosage form.

Example 4

Particle Size Analysis

This example details the results of particle size analysis for a CoQ10 powder prepared according to the procedure described in Example 2 and a powder obtained from a commercially-available CoQ10 product (Q-GEL available from Tishcon Corp.) used as a reference sample.

Samples were prepared by dispersing a powder sample in a small amount of water under a cover slide, and then further dispersing the sample by gently moving the cover slip over the bottom slide. Photomicrographs were taken at 400× magnification using an AMERICAN OPTICAL microscope equipped with phase inversion.

Figure 4:
FIG. 4 is a photomicrograph obtained during particle size analysis as described in Example 4.
Figure 5A:
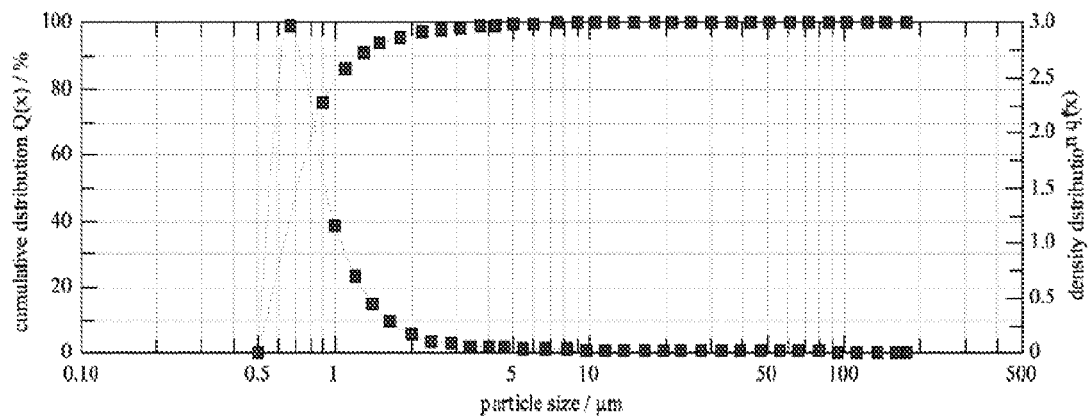
FIGS. 5A-5F provide results of particle size analysis as described in Example 6.
Figure 5B:
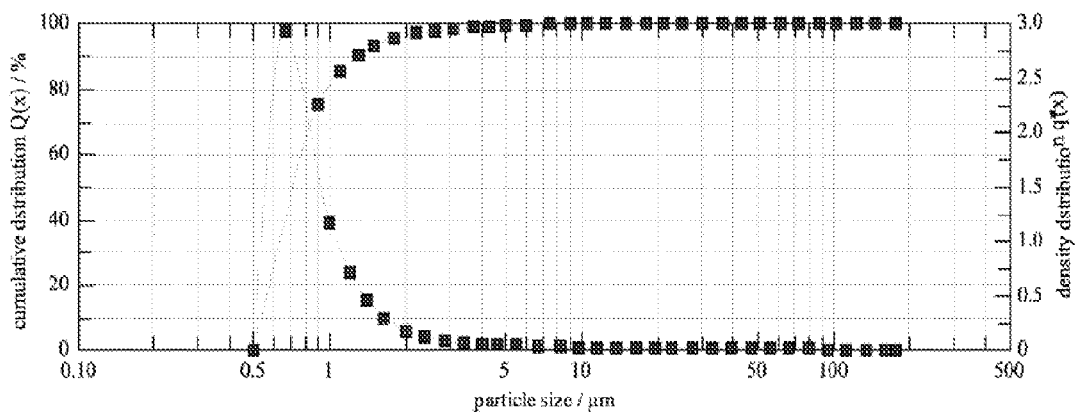
Figure 5C:
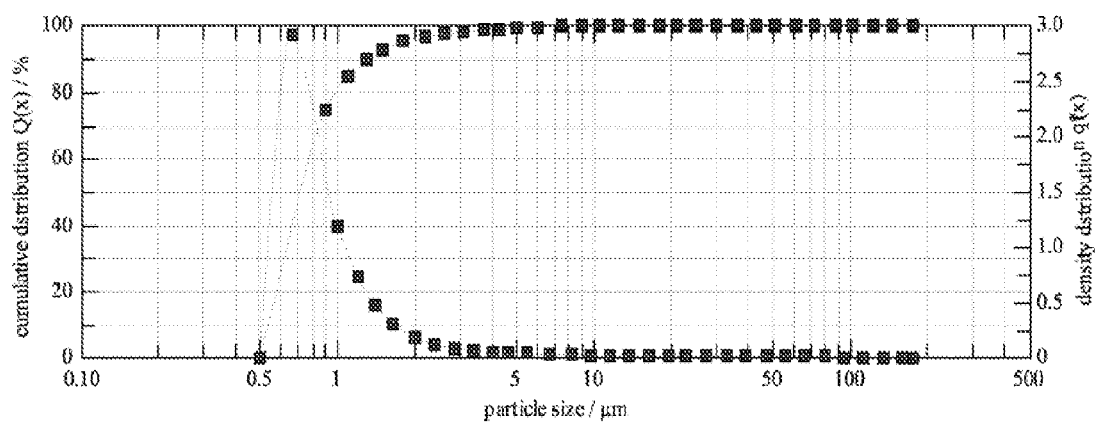
Figure 5D:
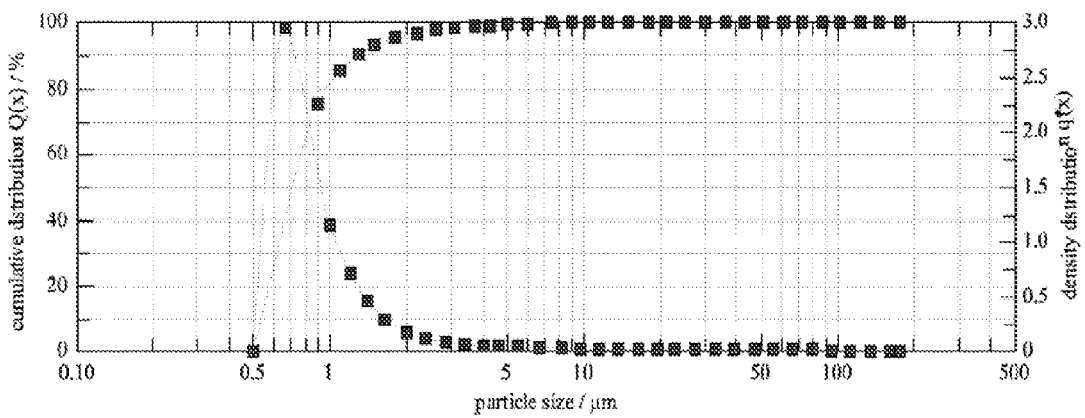
Figure 5E:
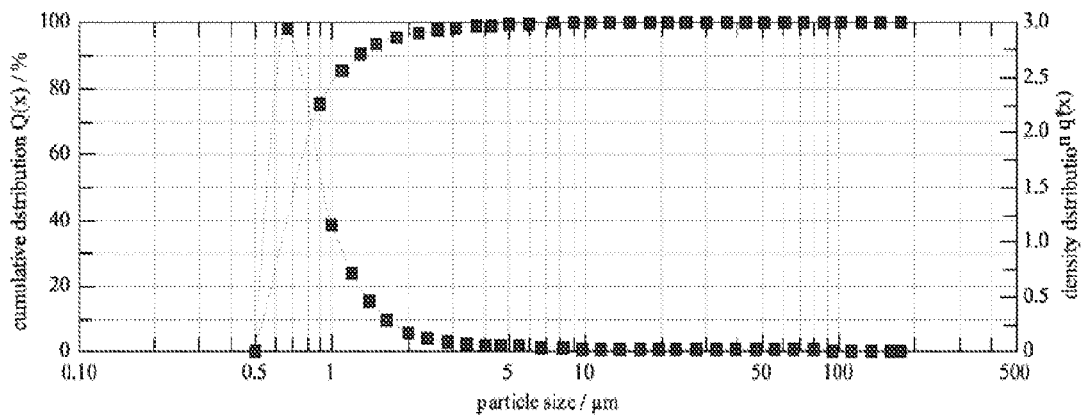
Figure 5F:
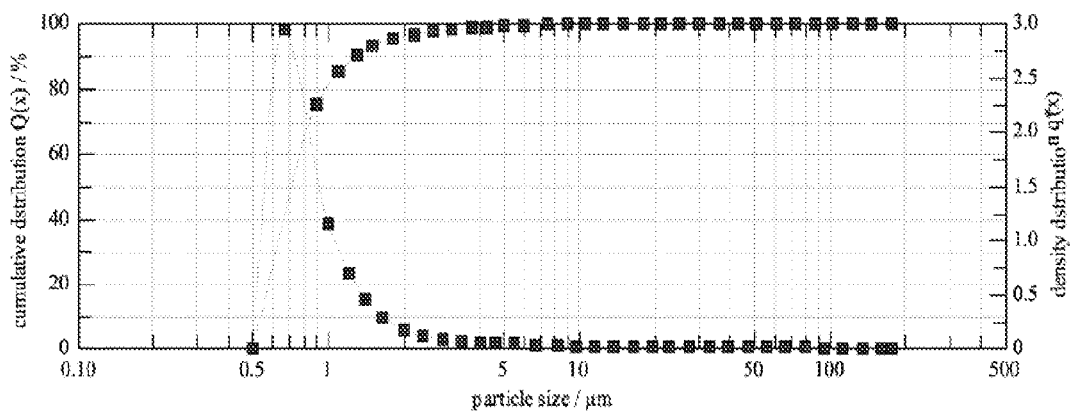
Figure 6A:
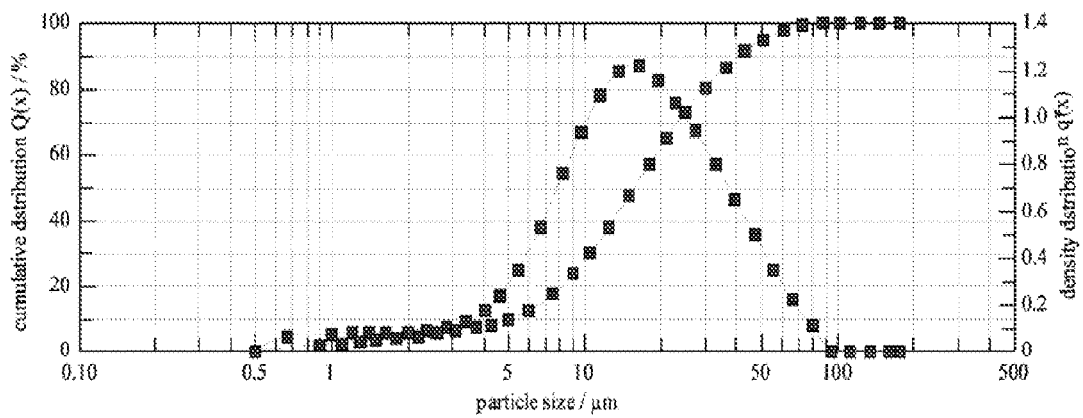
FIGS. 6A-6F provide results of particle size analysis as described in Example 6.
Figure 6B:
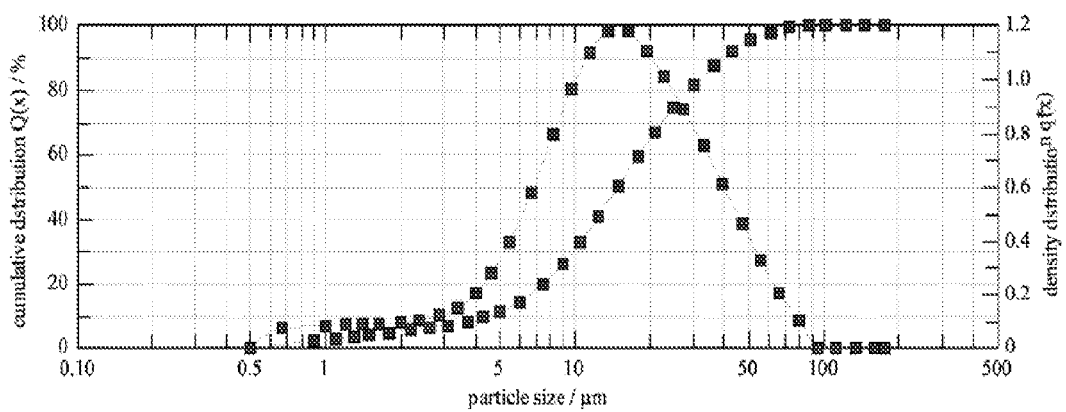
Figure 6C:
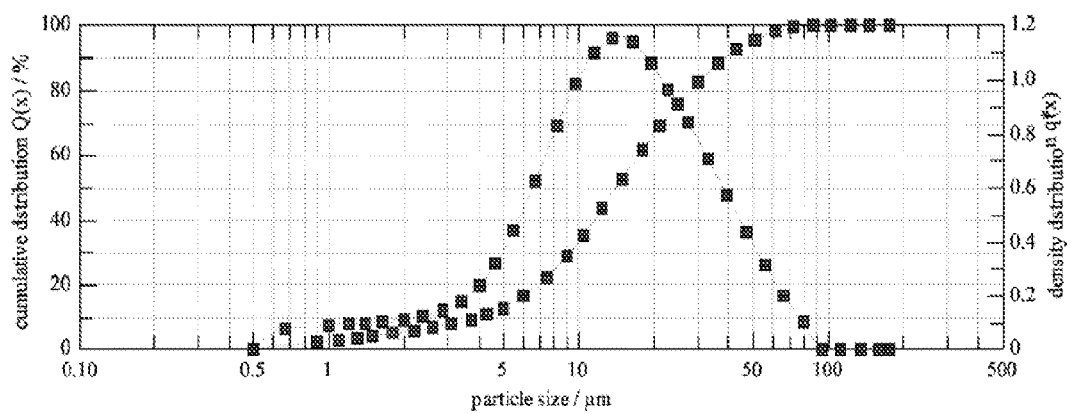
Figure 6D:
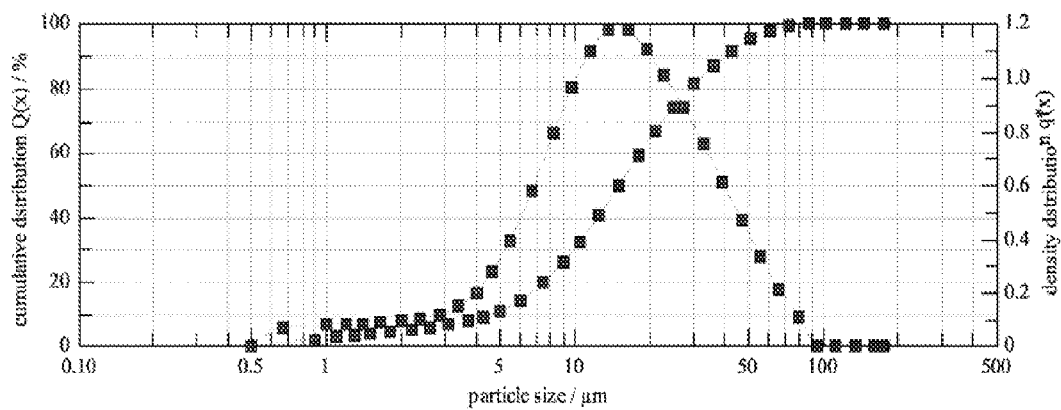
Figure 6E:
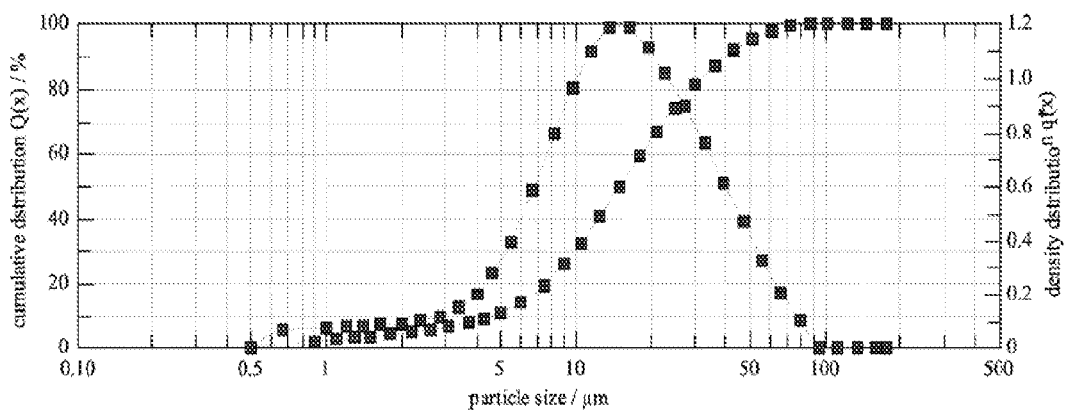
Figure 6F:
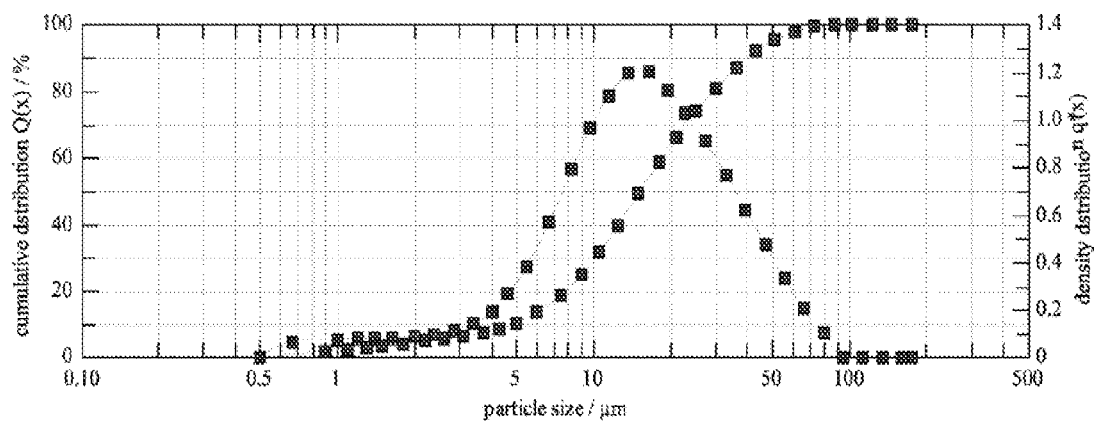

FIG. 4 depicts the photomicrograph for the reference sample comprising the commercially-available CoQ10 product. Large crystals (25 to 100 μm in diameter) of coenzyme Q10 are clearly visible in the image.

In contrast, as detailed herein, the CoQ10 powder composition of the present invention, prepared using the procedure described in Example 2, has much smaller particulates, with a plurality of the particulates having diameters in the sub-micron range. As a result of this small average particulate size, and as detailed elsewhere herein, the CoQ10 formulations of the present invention are believed to exhibit improved bioavailability as compared to the commercially-available CoQ10 product.

Example 5

Exemplary Composition

The following details a particulate exemplary CoQ10-containing composition of the present invention. All percentages are weight percents. The composition was prepared generally in accordance with the method described in Examples 1 and 2.

Succinylated starch (CAPSUL): 27.6% (56.3 g)
Sodium bicarbonate: 0.3% (0.6 g)
Lauroyl macrogolglycerides (GELUCIRE 44/14): 23.2% (47.4 g)
Ubiquinone (CoQ10): 32% (65.4 g)
Phosphatidyl choline component (PHOSPHOLIPON 90G): 4.8% (9.9 g)
Ascorbic acid: 9.2% (18.7 g)
Fumed silica: 3% (6 g)

Example 6

CoQ10 Starting Material Particle Size Analysis

This example details the results of particle size analysis for a commercially available CoQ10 starting material. Dry samples of KANEKA Q10 powder were analyzed using laser diffraction to obtain a measurement of particle size characteristics.

Particle size analysis of the CoQ10 starting material was conducted using a dry dispersion method. A Symantec HELOS equipped with a RODOS dispersion module and a R3 lens was employed for the analysis. Prior to the analysis the sample was evaluated using optical microscopy. Particles were well dispersed and ranged in size from approximately 5 microns to approximately 90 microns.

FIGS. 5A-5F include the resulting data for 6 analyses (A-F). Generally, the results show a median particle size of approximately 0.76 µm, with approximately 90% of the individual particulates having a largest dimension less than about 1.28 µm. Table 1 includes a summary of the results for each of samples A-F.

TABLE 1

CoQ10 Particulate Size Distribution (Number Basis)

| | $x_{10}$ | $x_{50}$ | $x_{90}$ | $x_{95}$ | $x_{99}$ |
|---|---|---|---|---|---|
| A | 0.55 | 0.76 | 1.28 | 1.74 | 5.13 |
| B | 0.55 | 0.77 | 1.29 | 1.77 | 4.98 |
| C | 0.55 | 0.77 | 1.32 | 1.80 | 4.93 |
| D | 0.55 | 0.77 | 1.30 | 1.78 | 5.14 |
| E | 0.55 | 0.77 | 1.30 | 1.79 | 5.20 |
| F | 0.55 | 0.77 | 1.30 | 1.79 | 5.30 |
| Avg. | 0.55 | 0.77 | 1.30 | 1.78 | 5.11 |

Calculation of the particle size distribution on the basis of total volume, however, reveals that the KANEKA Q10 powder is substantially non-uniform. A significant portion of the total powder volume is in the form of large particulates, with more than 50% of the total volume attributable to particulates greater than 15 µm in diameter.

FIGS. 6A-6F include data resulting from 6 analyses. Table 2 summarizes the data for the six analyses (A-F).

TABLE 2

CoQ10 Particulate Size Distribution (Volume Basis)

| | $x_{10}$ | $x_{50}$ | $x_{90}$ | $x_{95}$ | $x_{99}$ |
|---|---|---|---|---|---|
| A | 5.21 | 15.89 | 41.41 | 51.76 | 71.75 |
| B | 4.63 | 15.04 | 40.36 | 50.62 | 71.16 |
| C | 4.16 | 14.37 | 39.46 | 49.96 | 70.79 |
| D | 4.77 | 15.15 | 40.75 | 51.11 | 71.66 |

TABLE 2-continued

CoQ10 Particulate Size Distribution (Volume Basis)

| | $x_{10}$ | $x_{50}$ | $x_{90}$ | $x_{95}$ | $x_{99}$ |
|---|---|---|---|---|---|
| E | 4.80 | 15.15 | 40.46 | 50.68 | 71.20 |
| F | 4.99 | 15.36 | 40.65 | 50.84 | 71.36 |
| Avg. | 4.76 | 15.16 | 40.52 | 50.83 | 71.32 |

Example 7

CoQ10 Particulate Size Analysis

This example details the results of particle size analysis for the microparticulates of CoQ10 and surfactants encapsulated in a starch matrix and spray dried according to the methods described herein (e.g., Examples 1 and 2). Samples of spray dried powder were suspended in water.

The spray-dried CoQ10 sample was analyzed using a wet dispersion method. A Malvern Mastersizer 2000 equipped with a Hydro2000S sample dispersion unit. Since the spray-dried CoQ10 includes CoQ10 particles within a water-soluble starch shell, the sample was dispersed throughout the water using an ultrasonic probe, causing the starch matrix of the powder to dissolve and release particles of CoQ10 associated with surfactants. Samples were analyzed to determine particle size distributions after 60 seconds and 120 seconds of sonication.

Figure 7A:
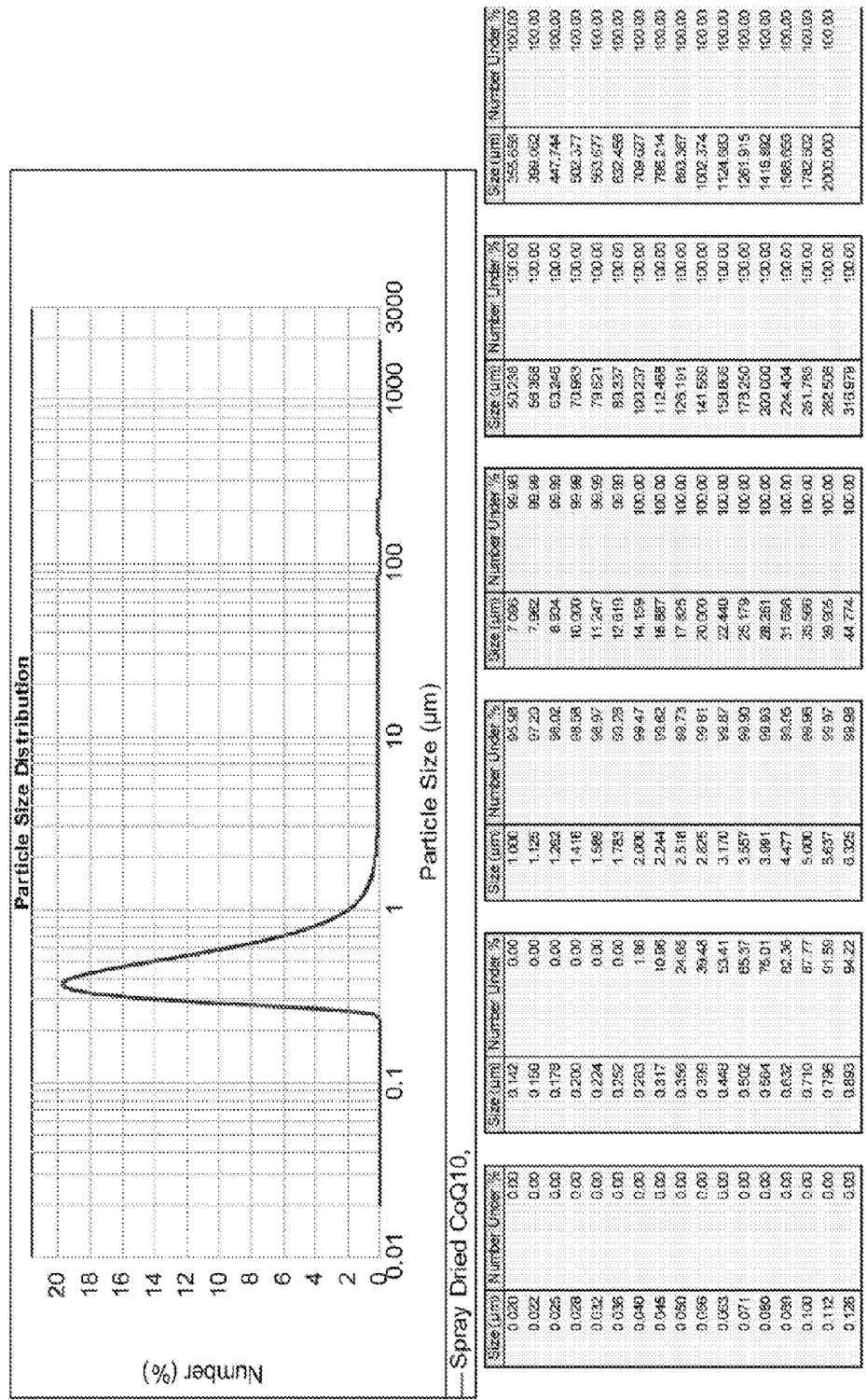
FIGS. 7A and 7B provide results of particle size analysis as described in Example 7.
Figure 7B:
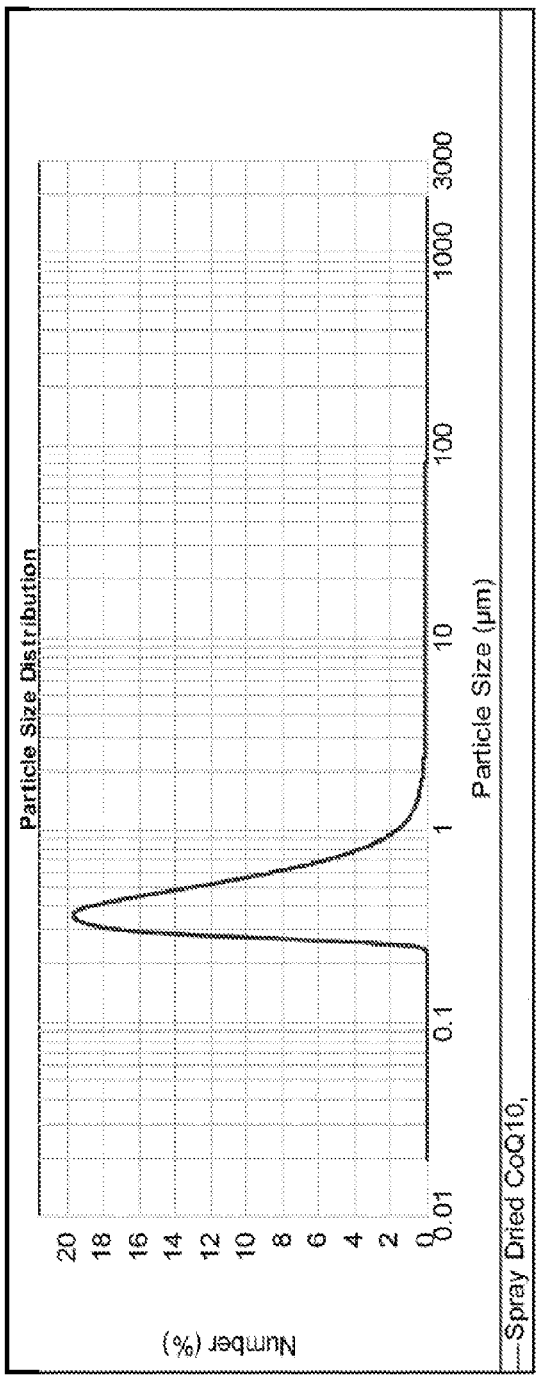
Figure 8A:
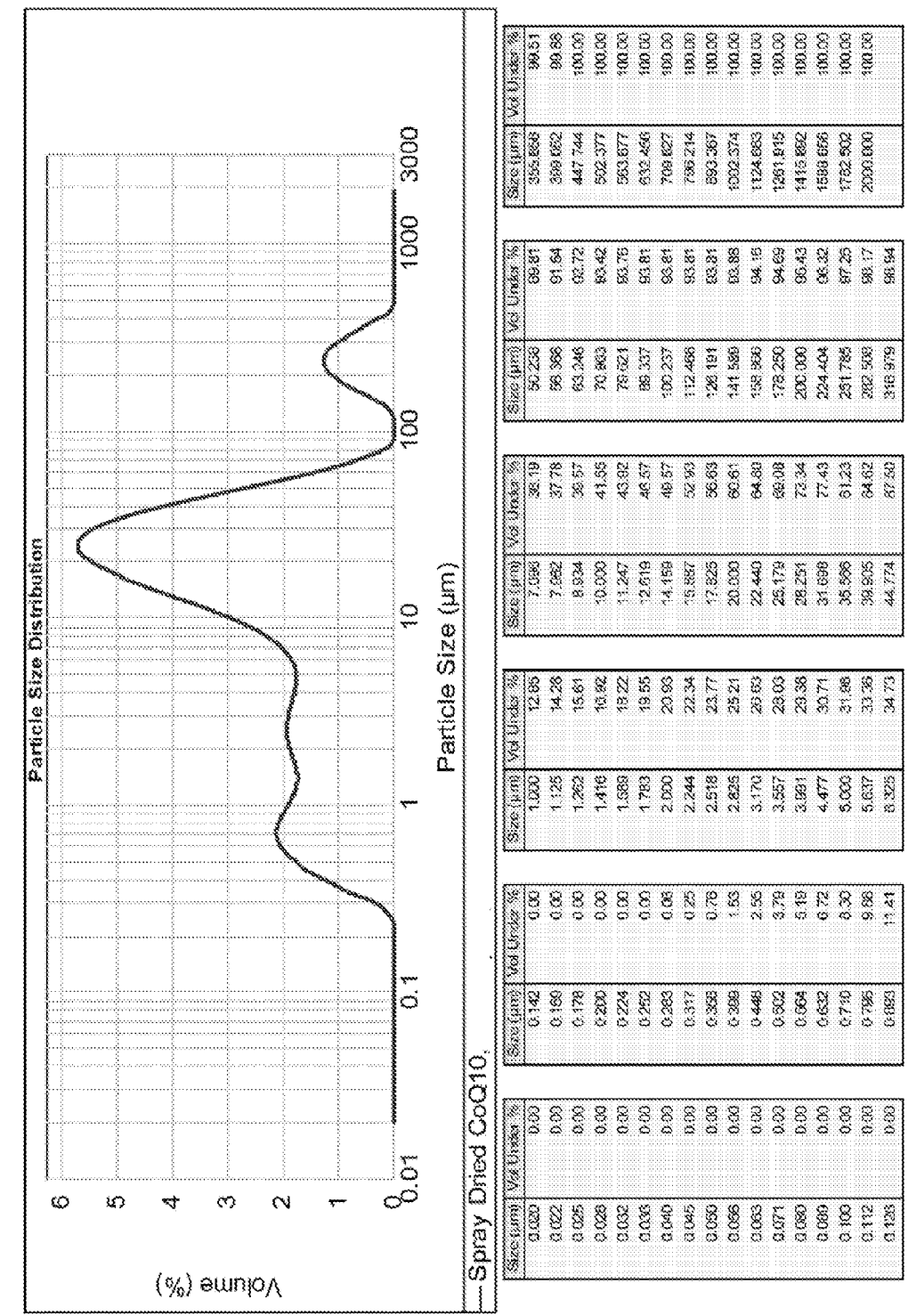
FIGS. 8A and 8B provide results of particle size analysis as described in Example 7.
Figure 8B:
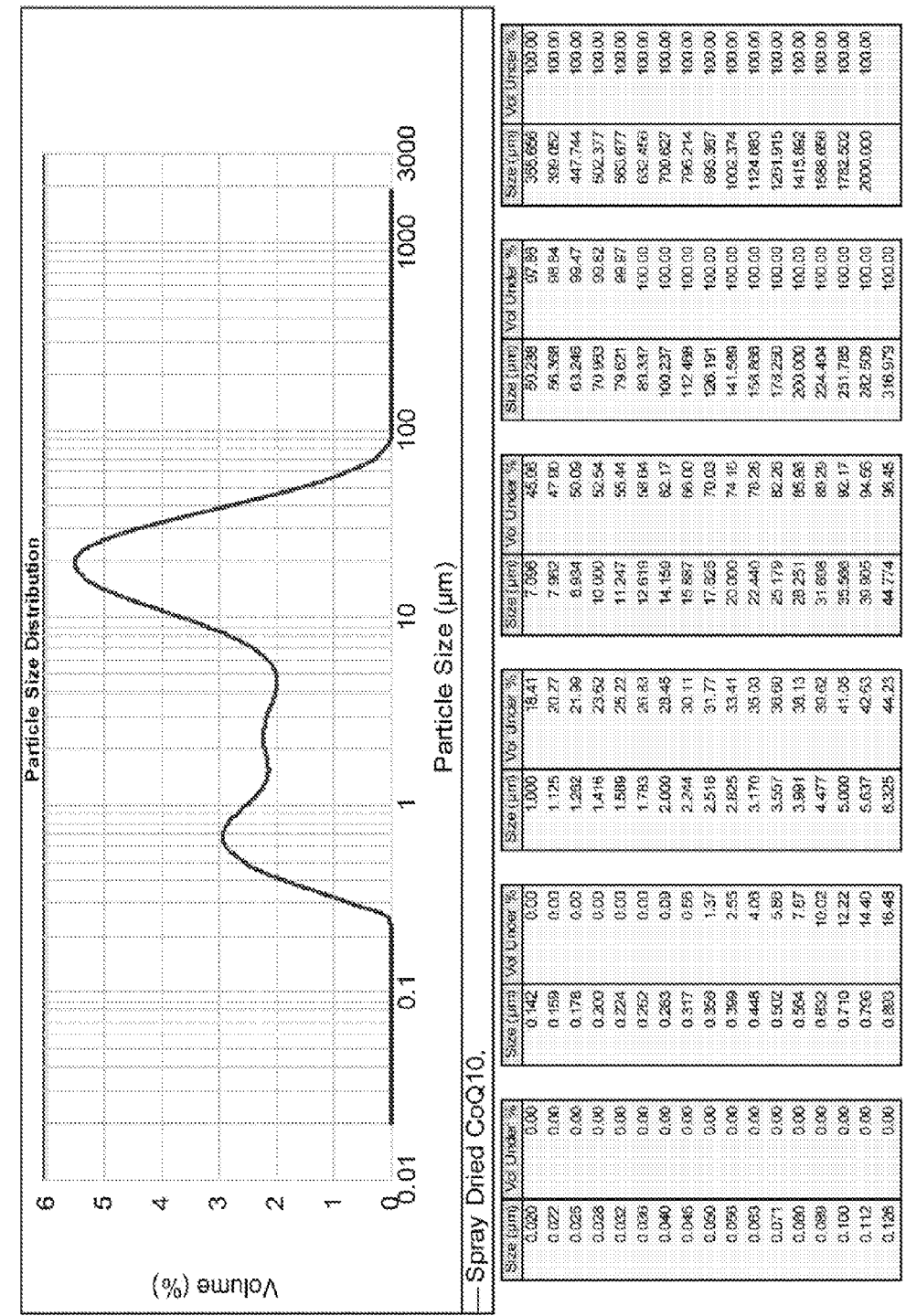
Figure 9A:
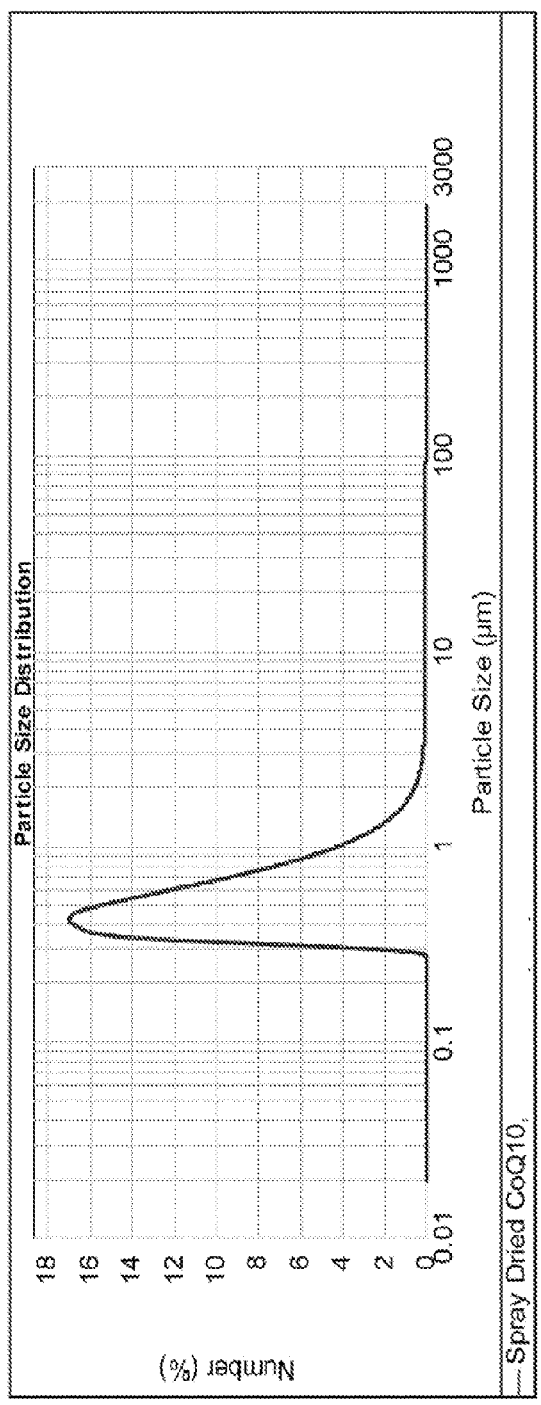
FIGS. 9A-9K provide results of particle size analysis as described in Example 7.
Figure 9B:
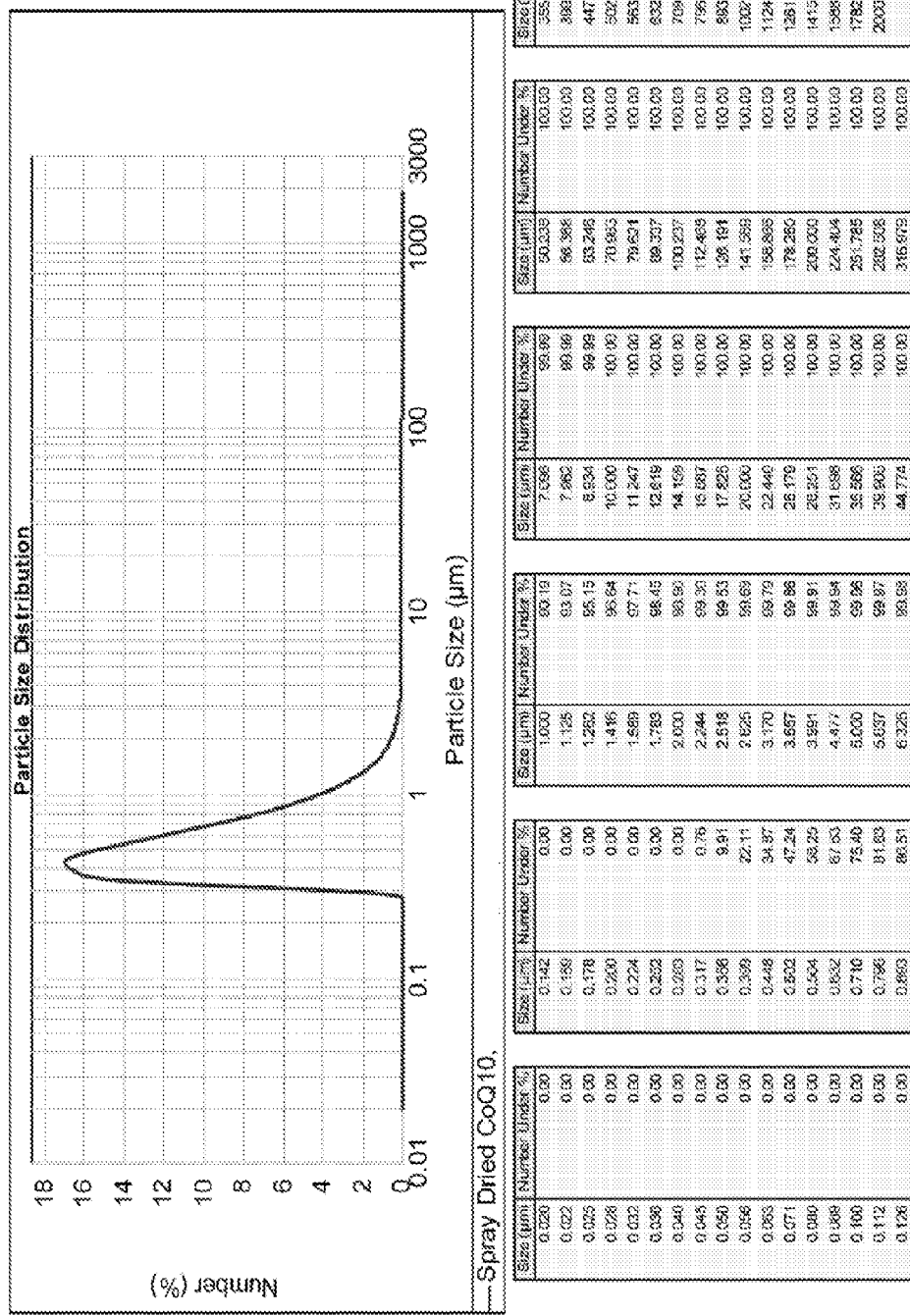
Figure 9C:
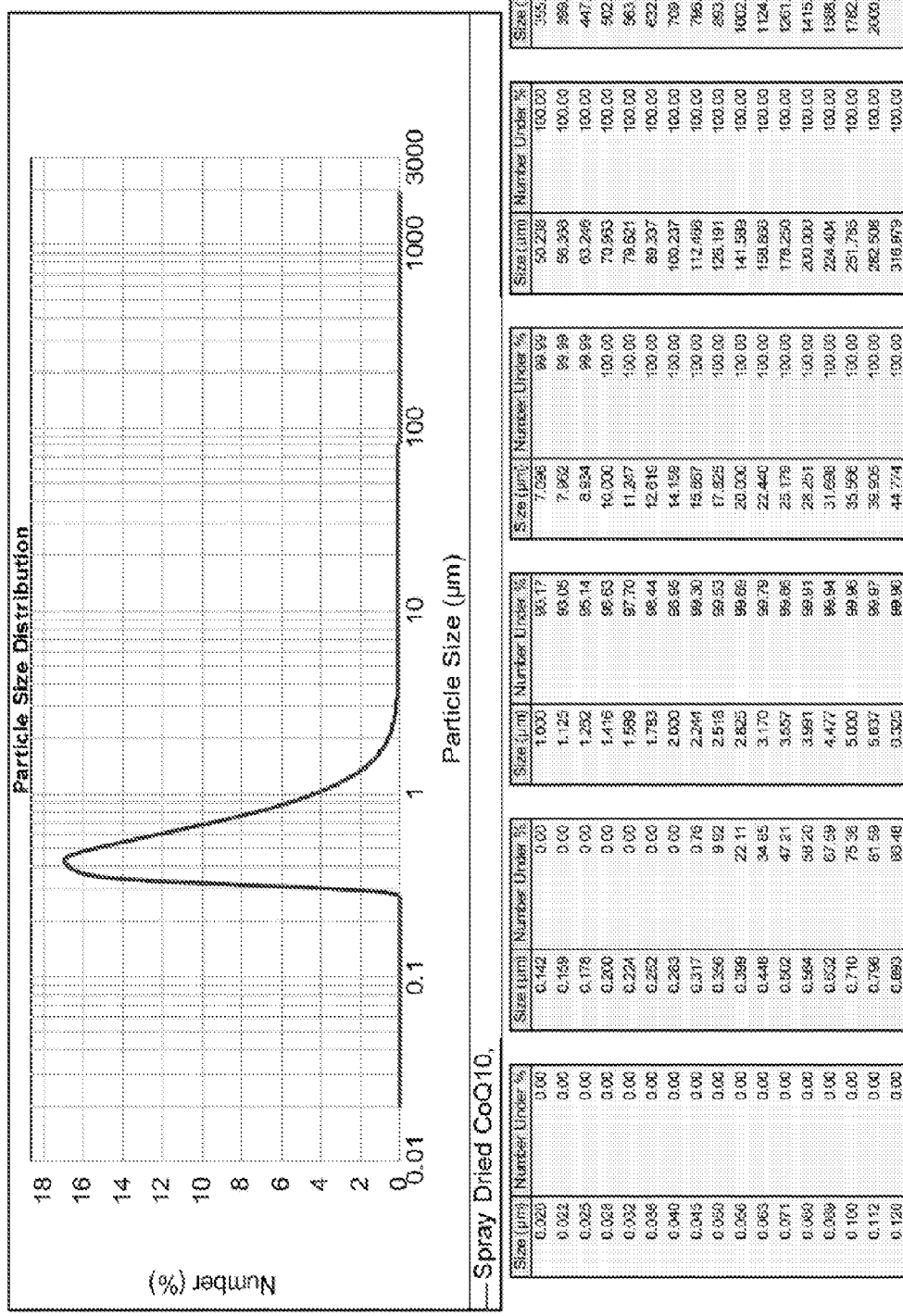
Figure 9D:
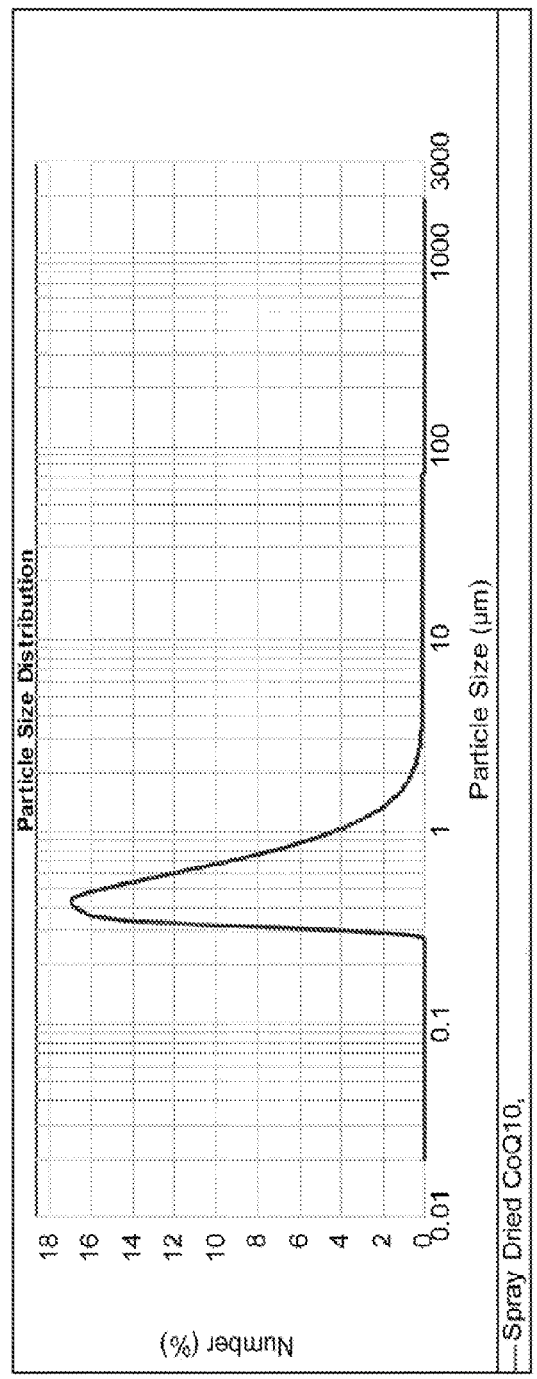
Figure 9E:
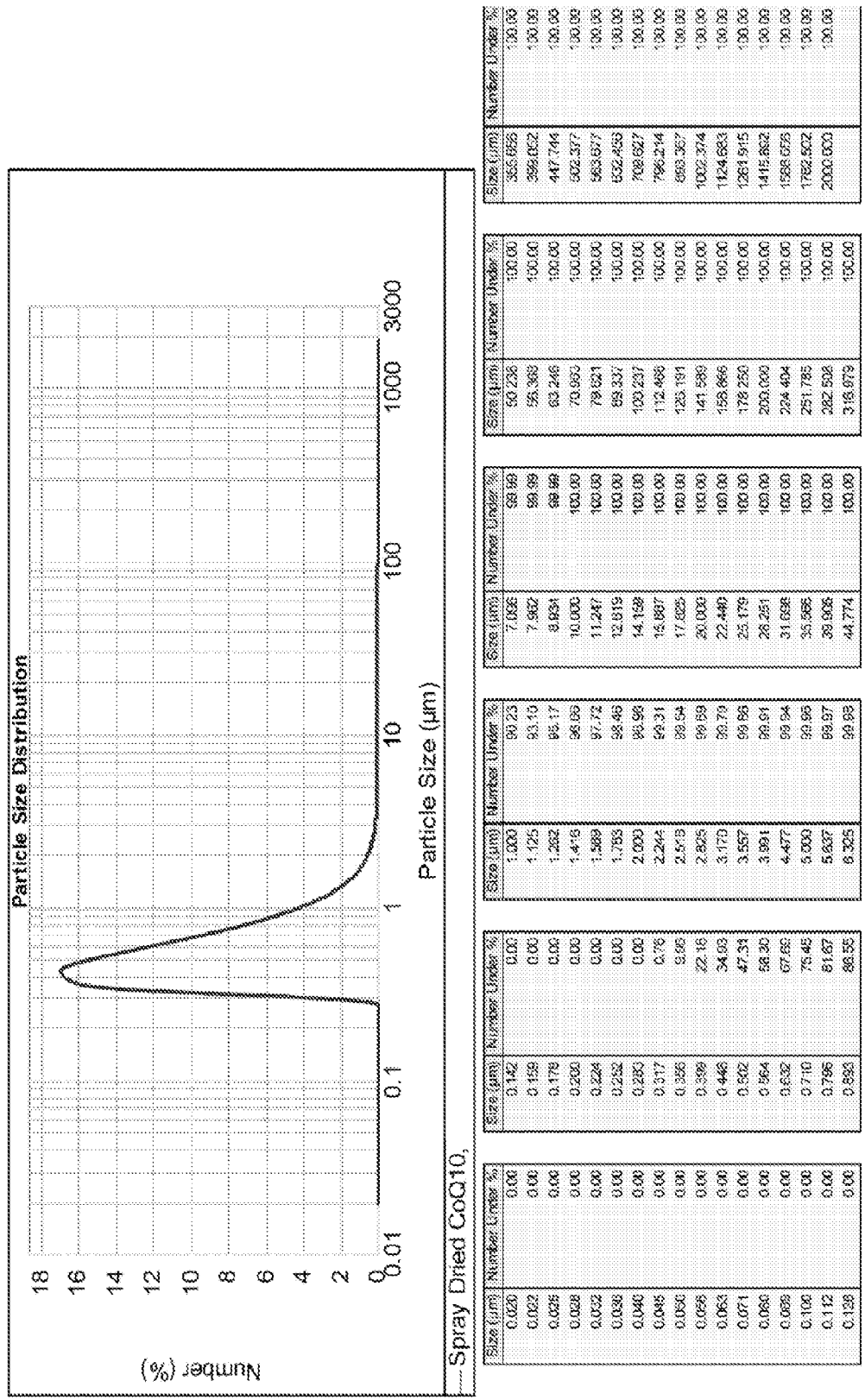
Figure 9F:
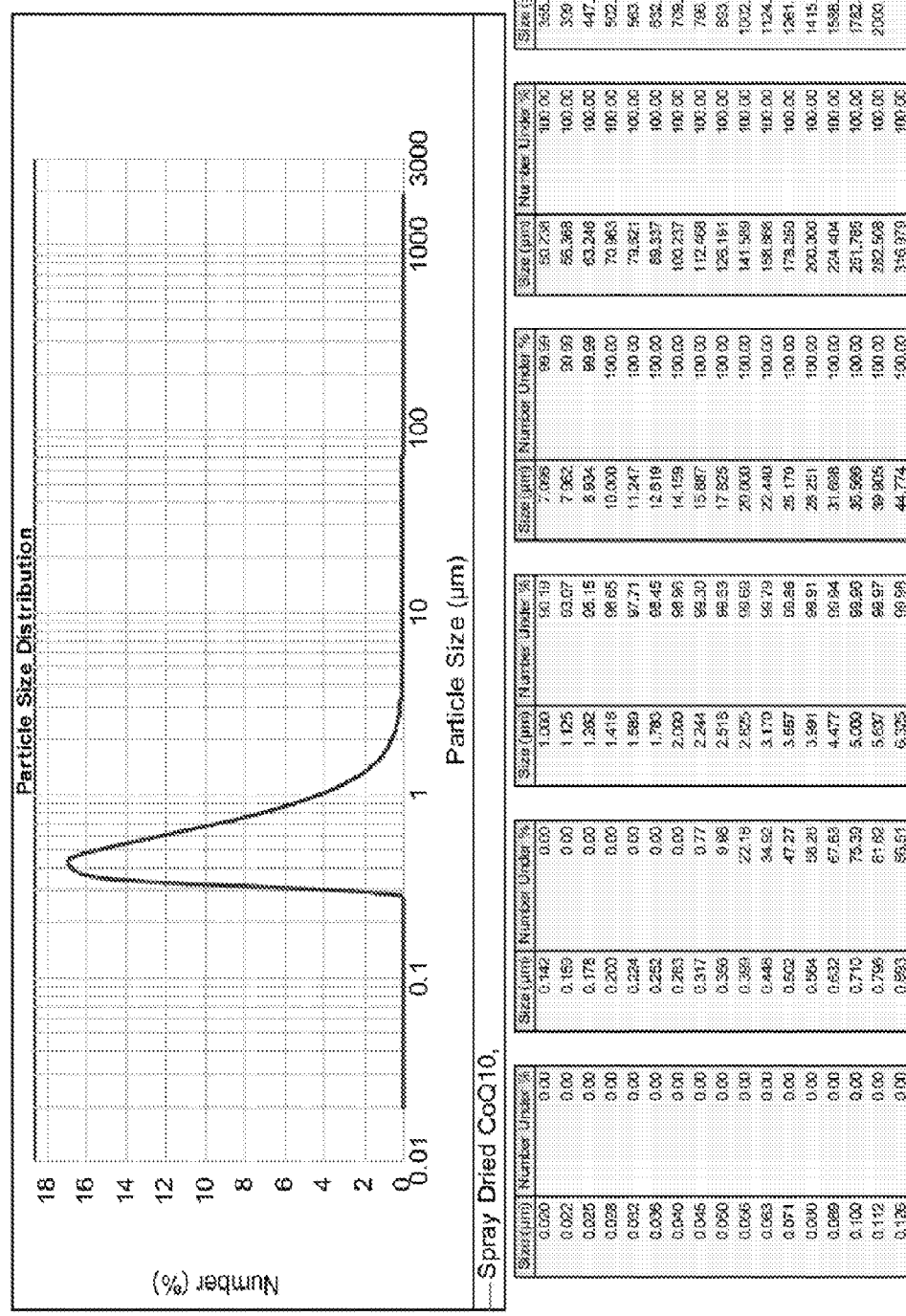
Figure 9G:
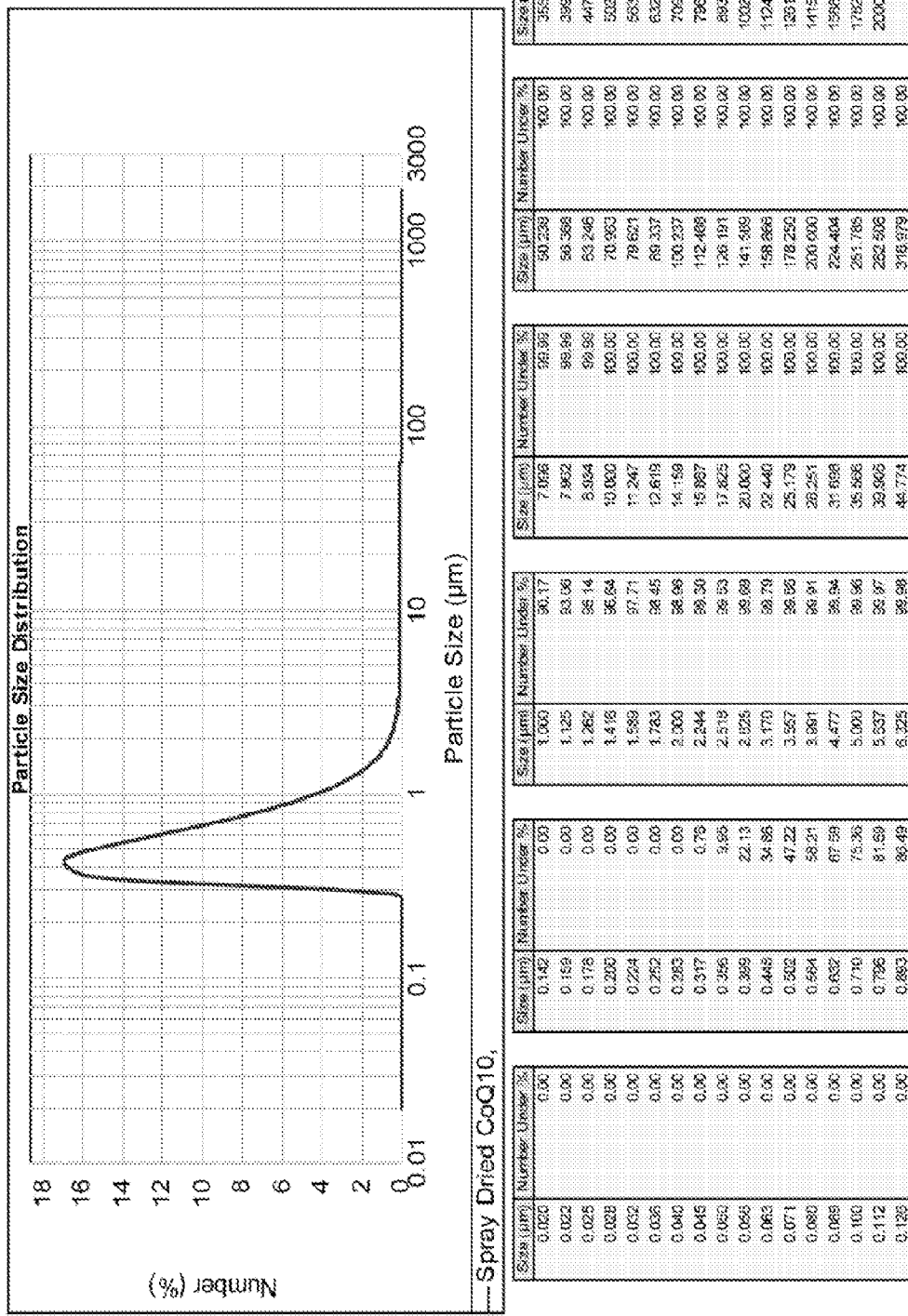
Figure 9H:
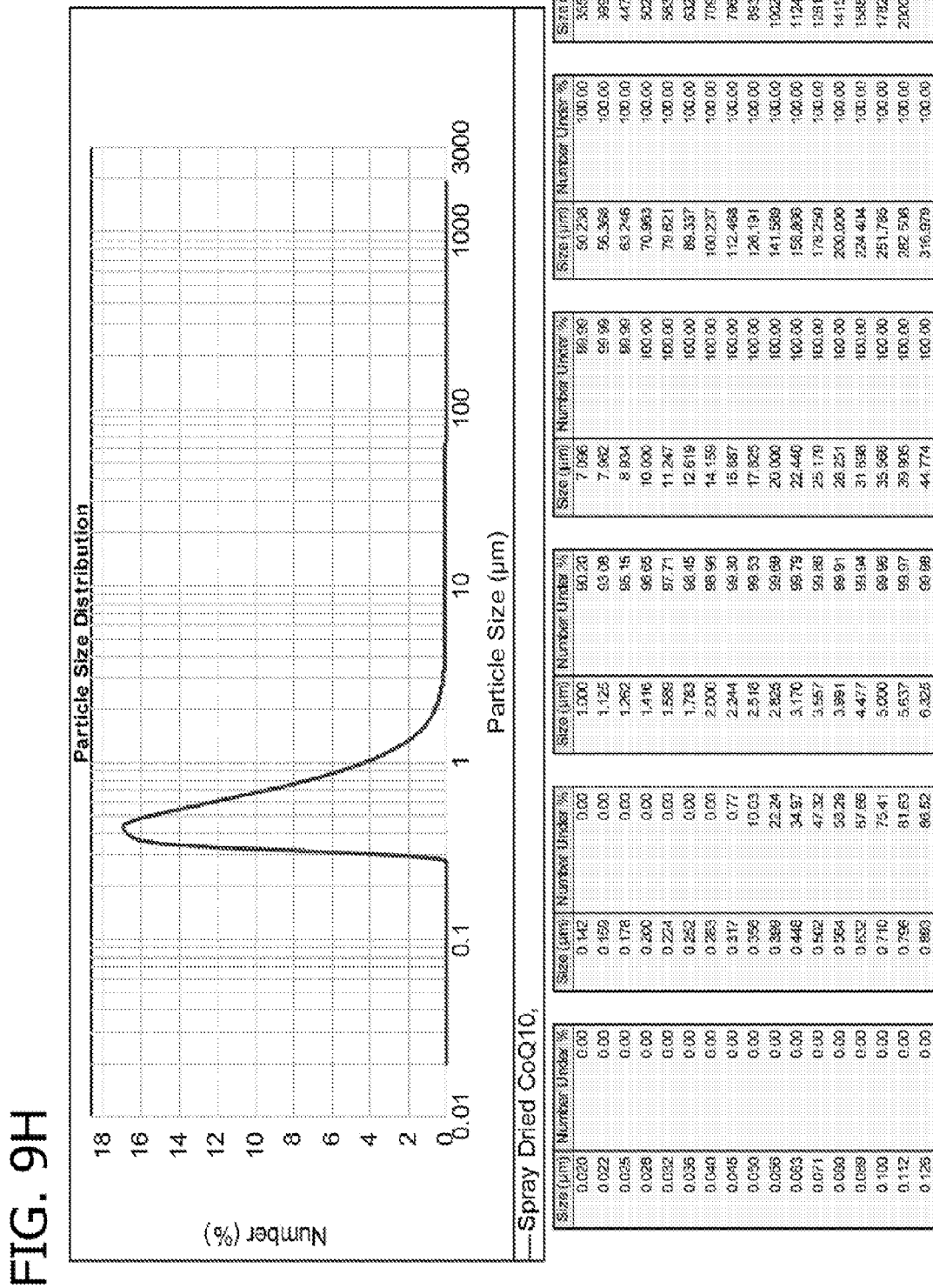
Figure 9I:
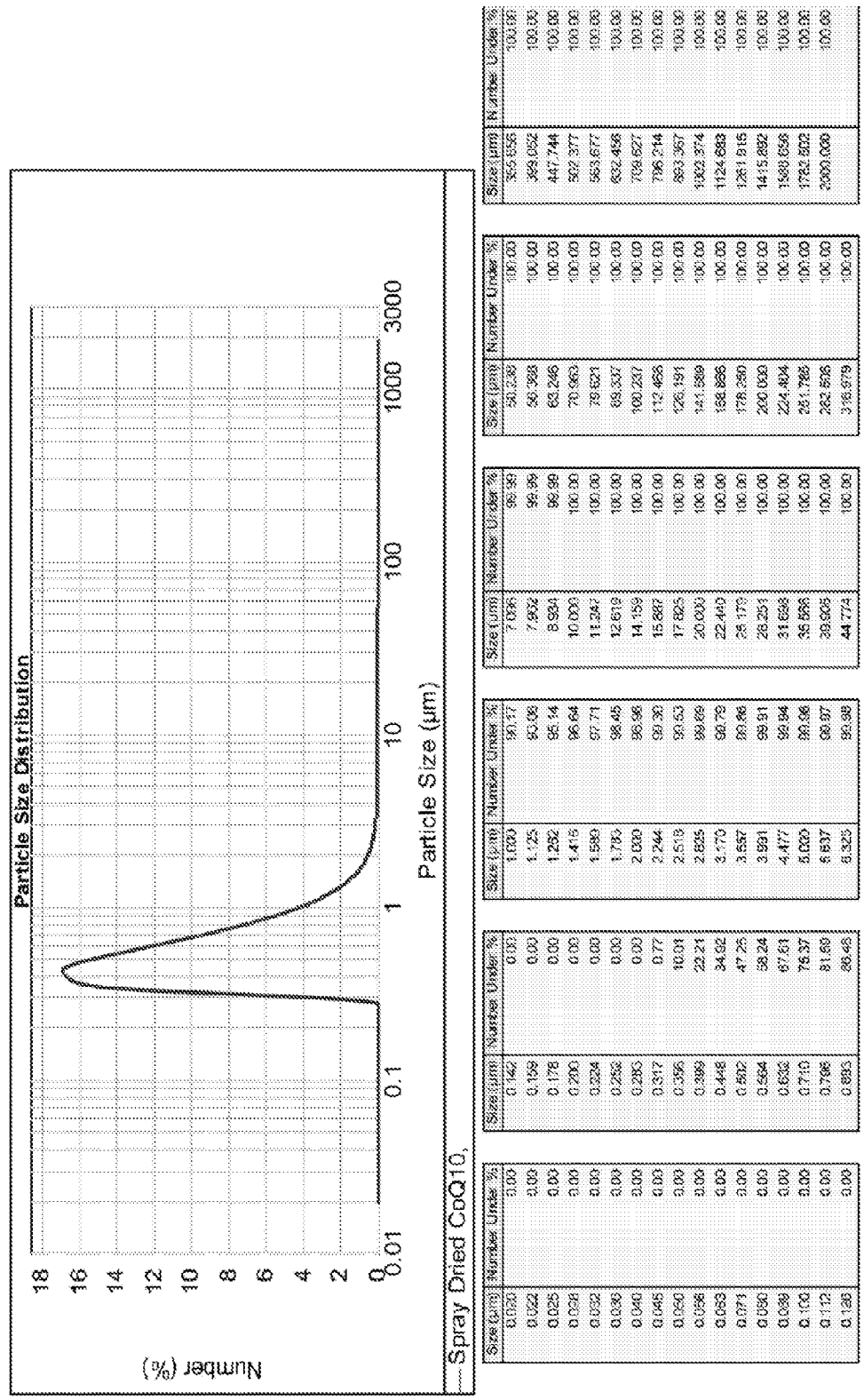
Figure 9J:
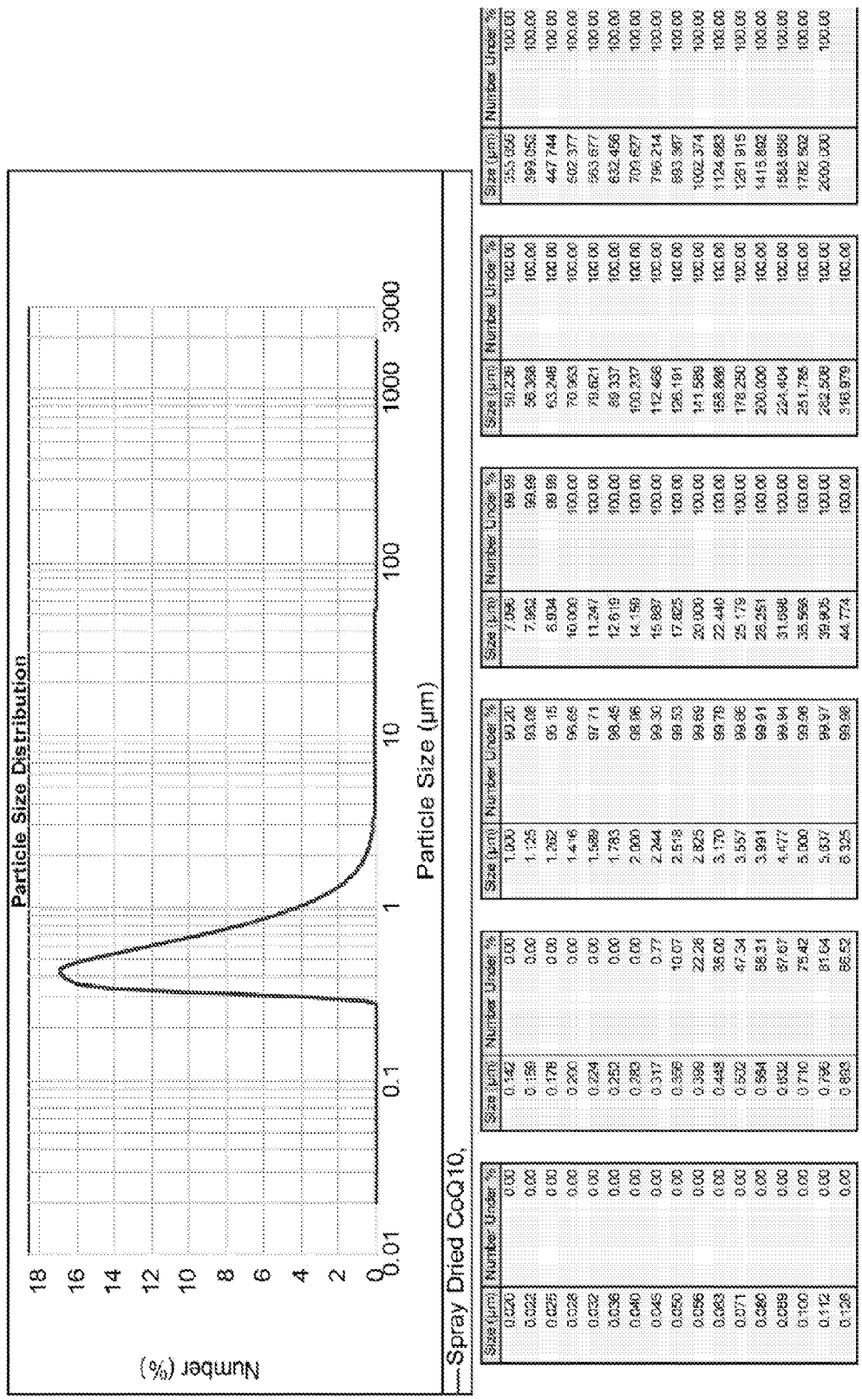
Figure 9K:
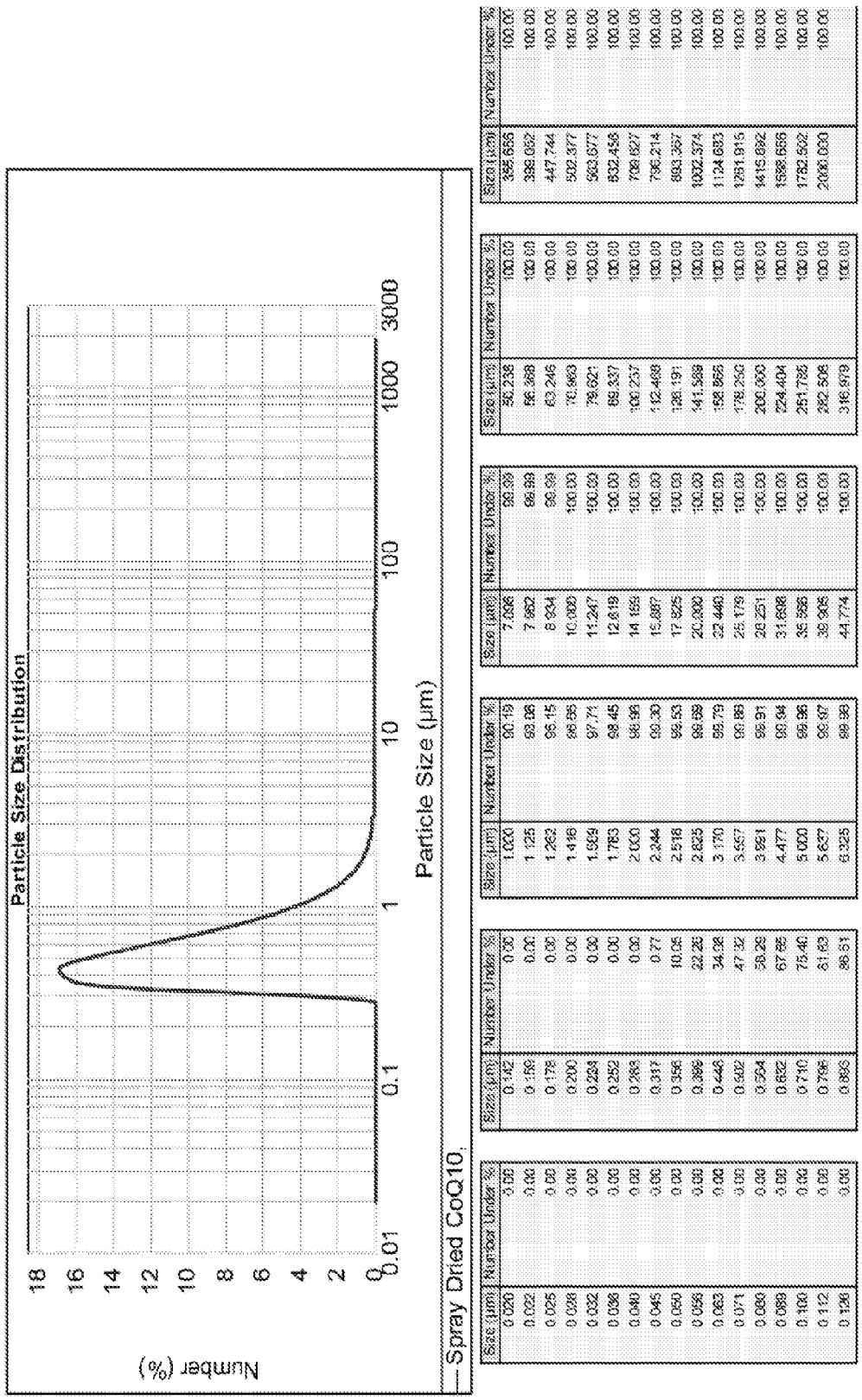
Figure 10A:
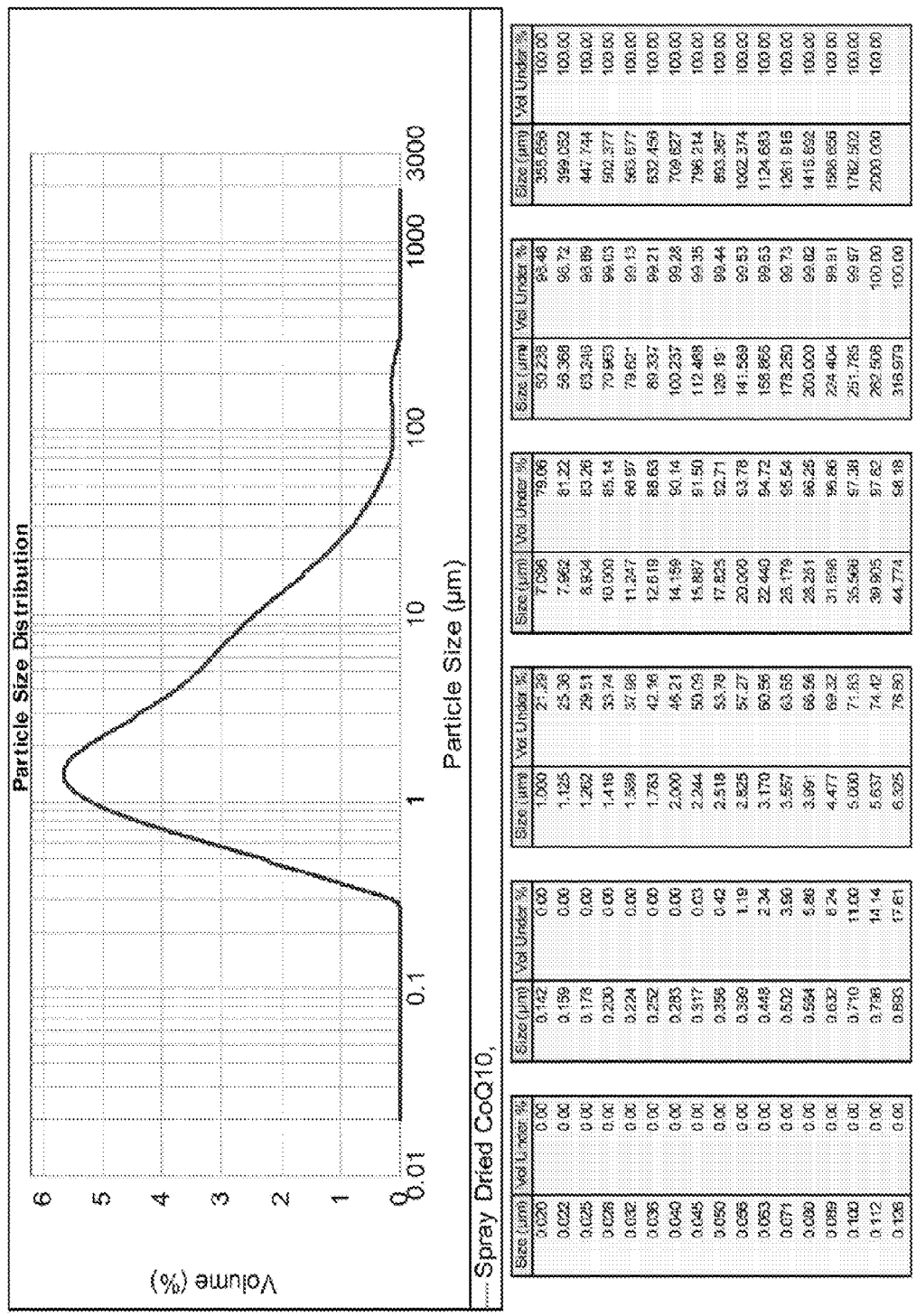
FIGS. 10A-10K provide results of particle size analysis as described in Example 7.
Figure 10B:
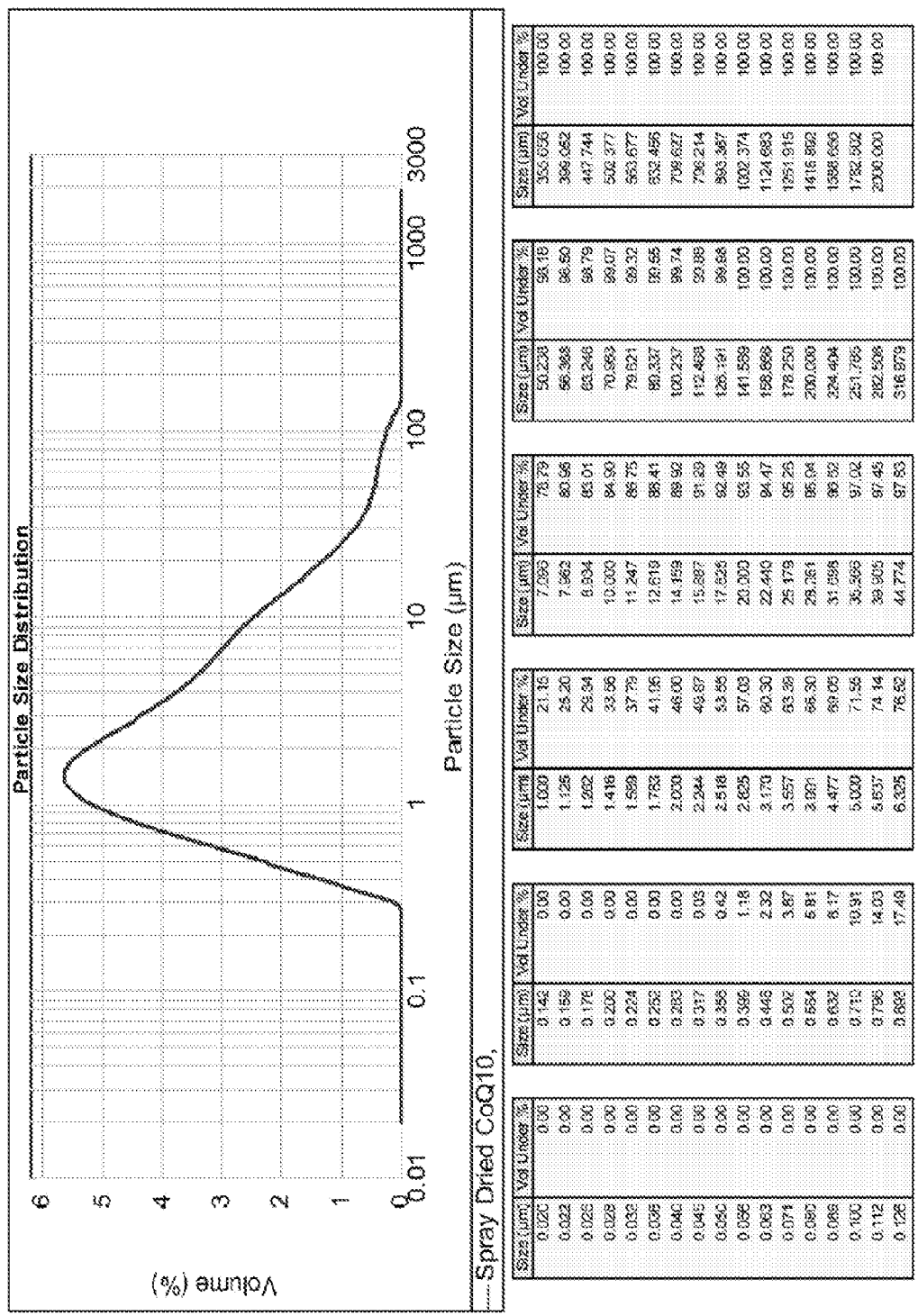
Figure 10C:
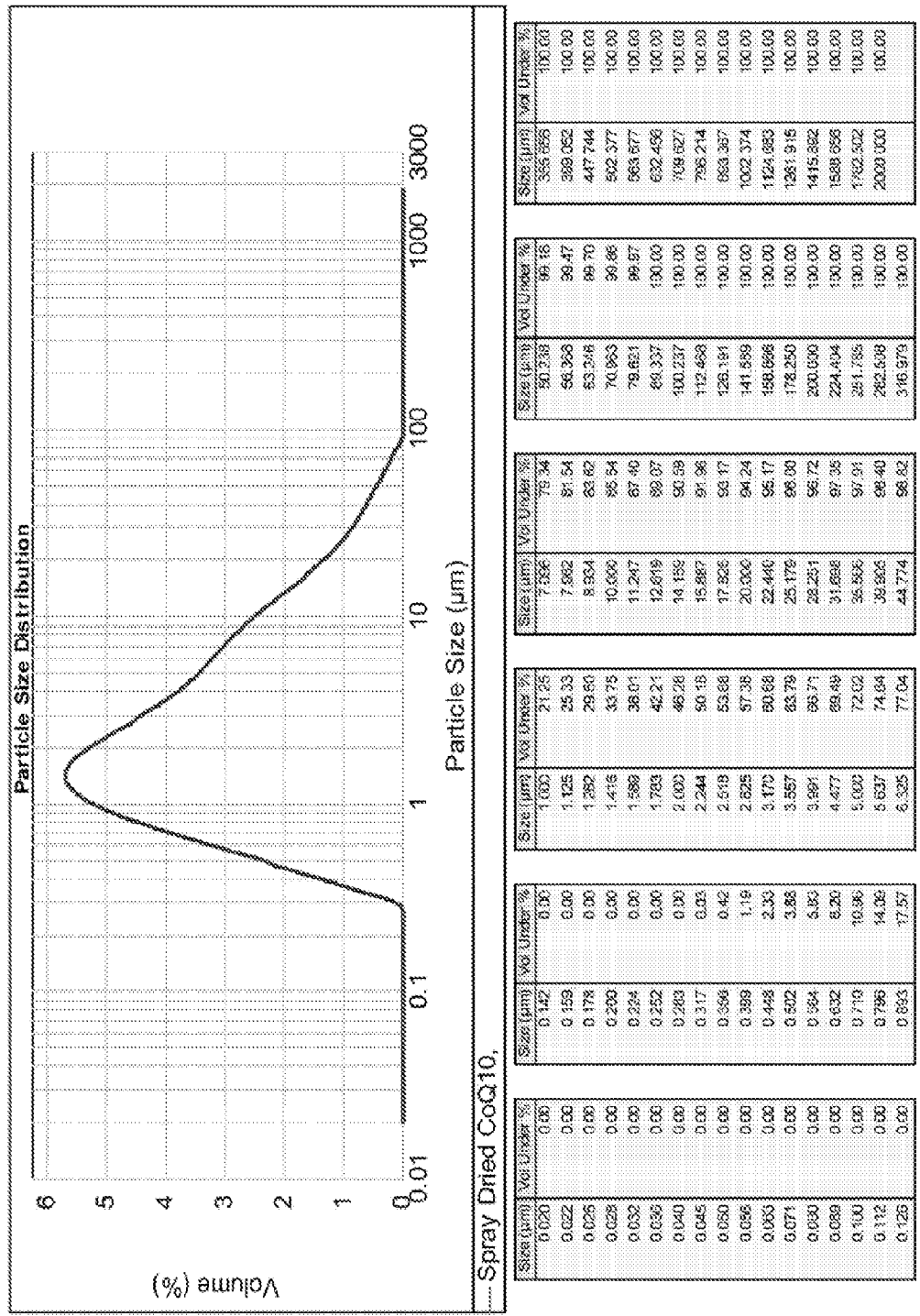
Figure 10D:
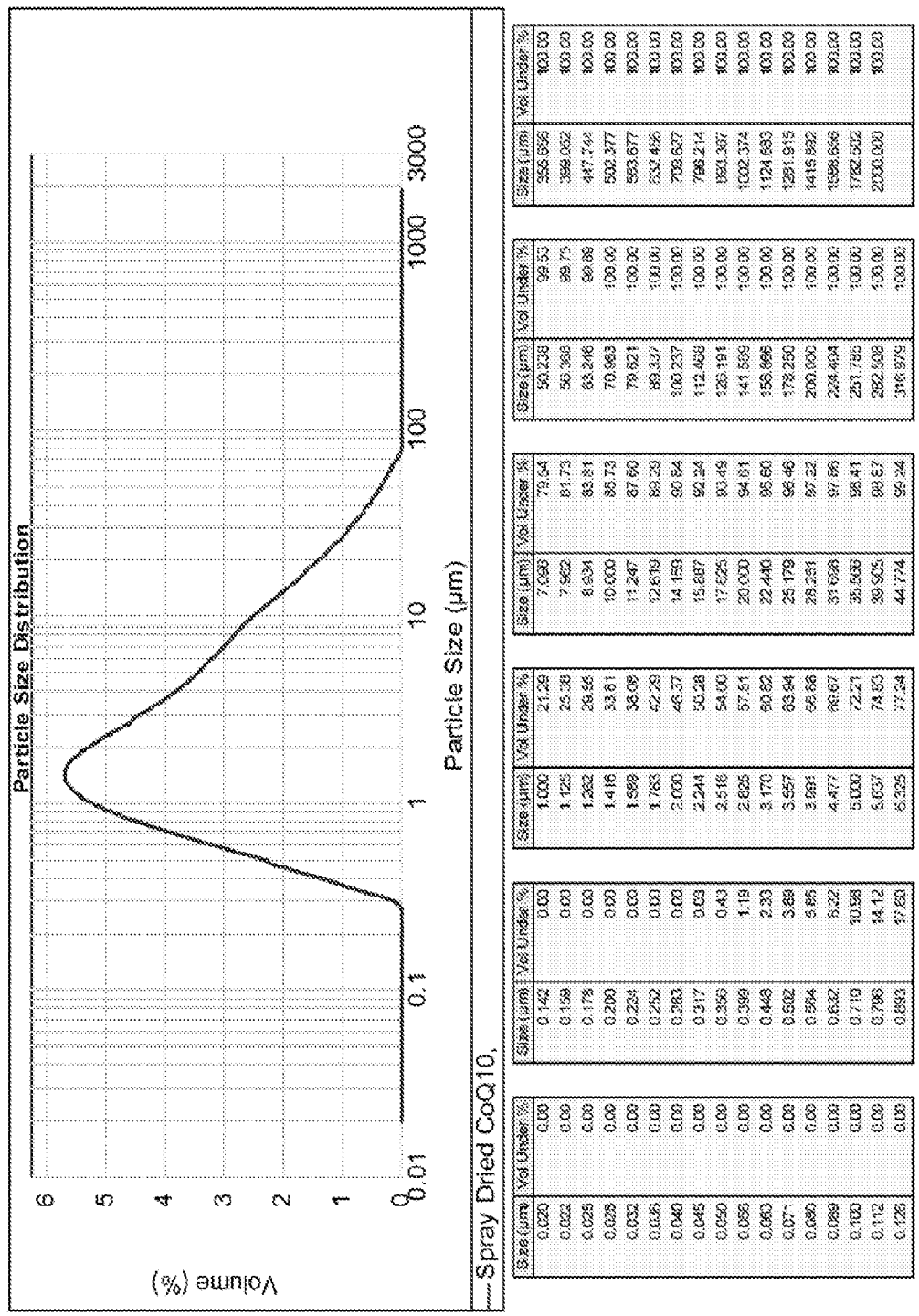
Figure 10E:
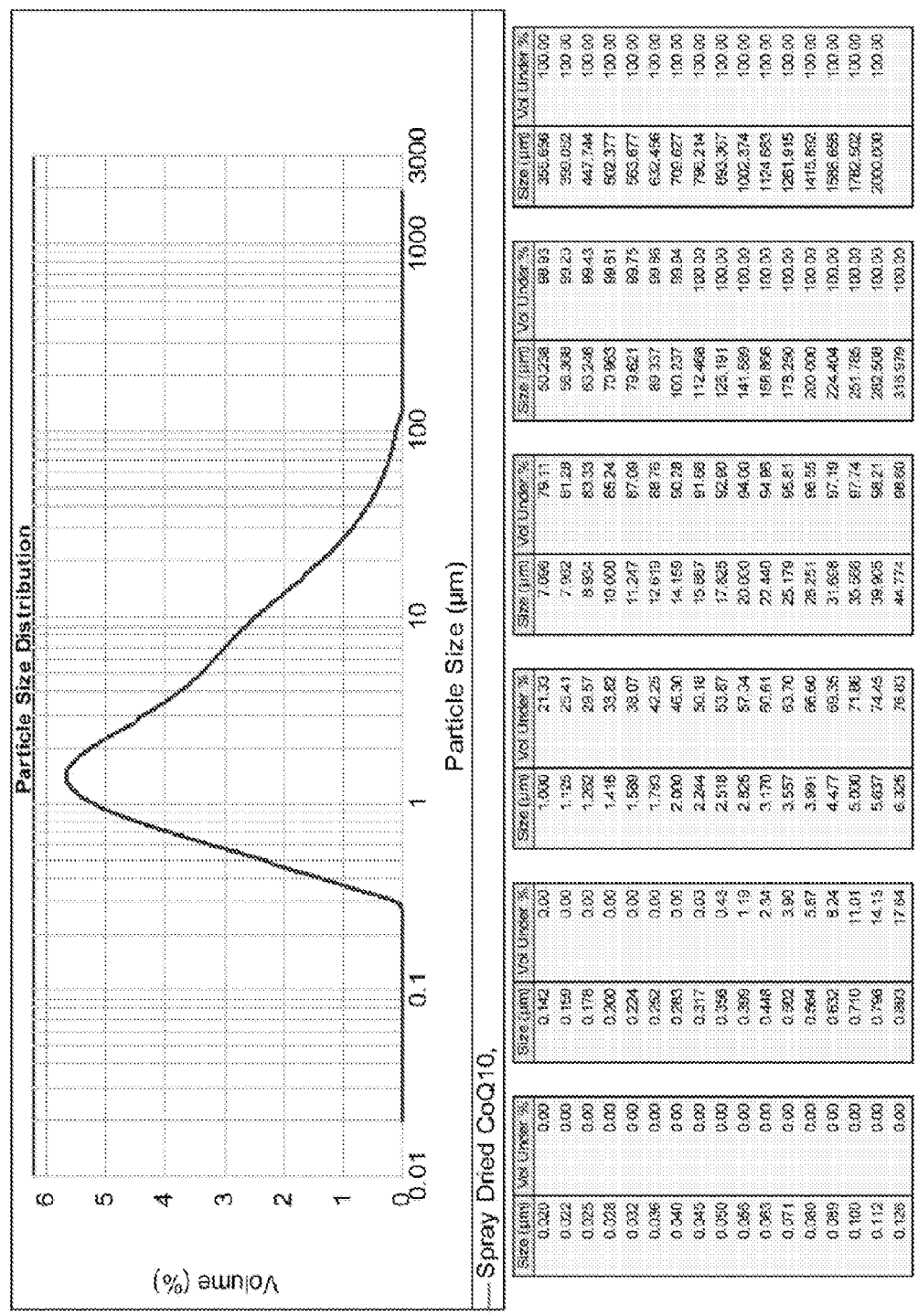
Figure 10F:
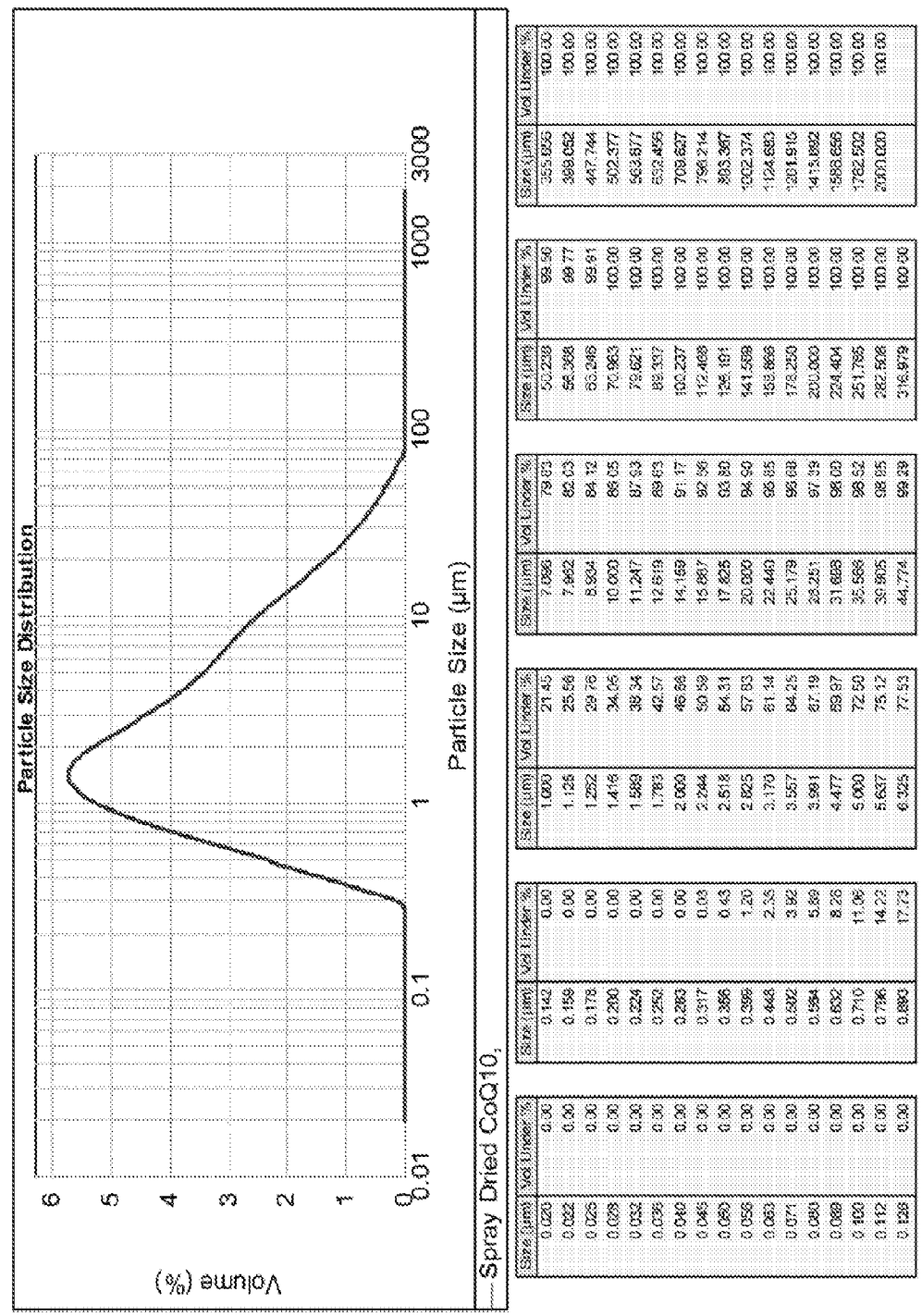
Figure 10G:
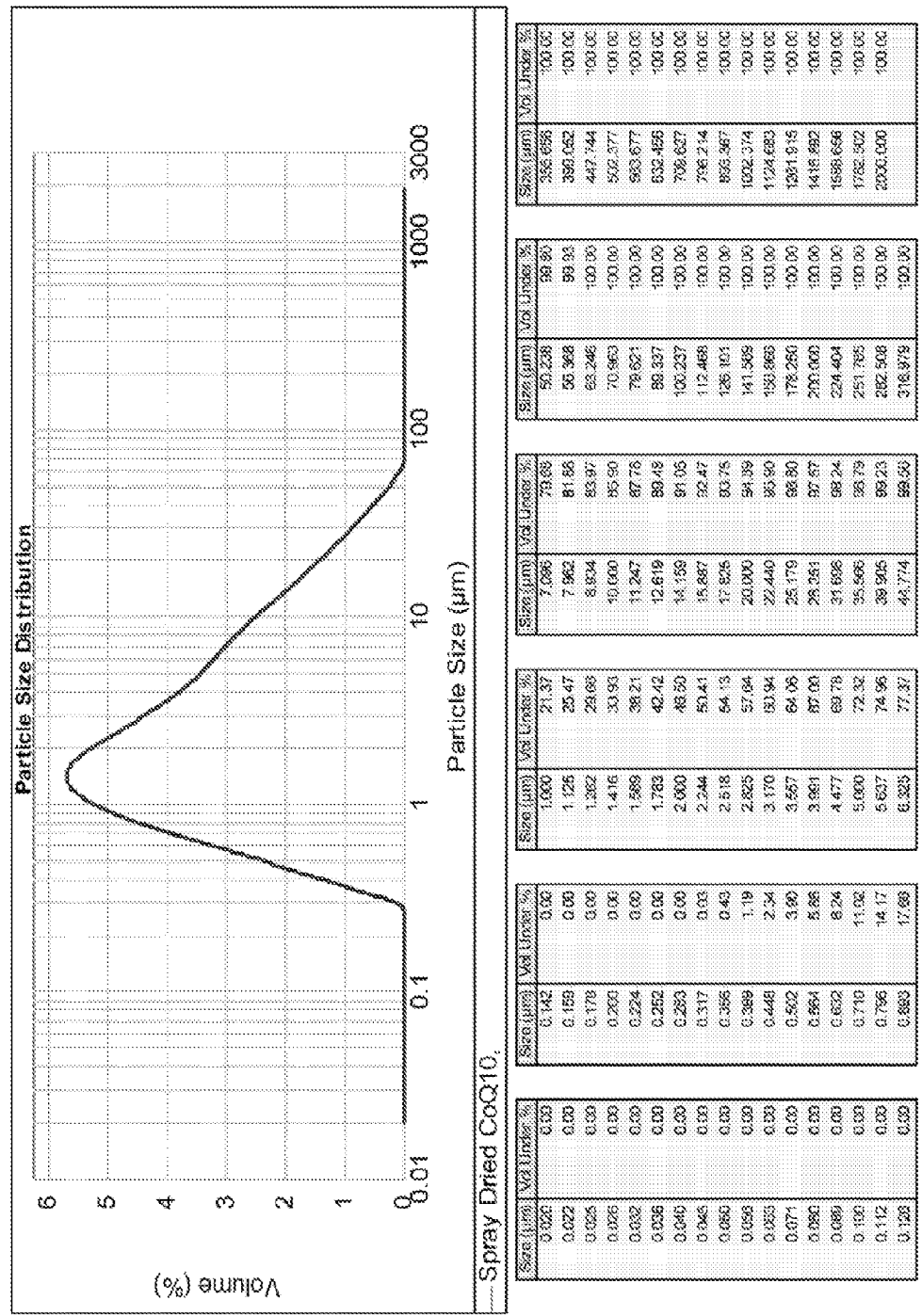
Figure 10H:
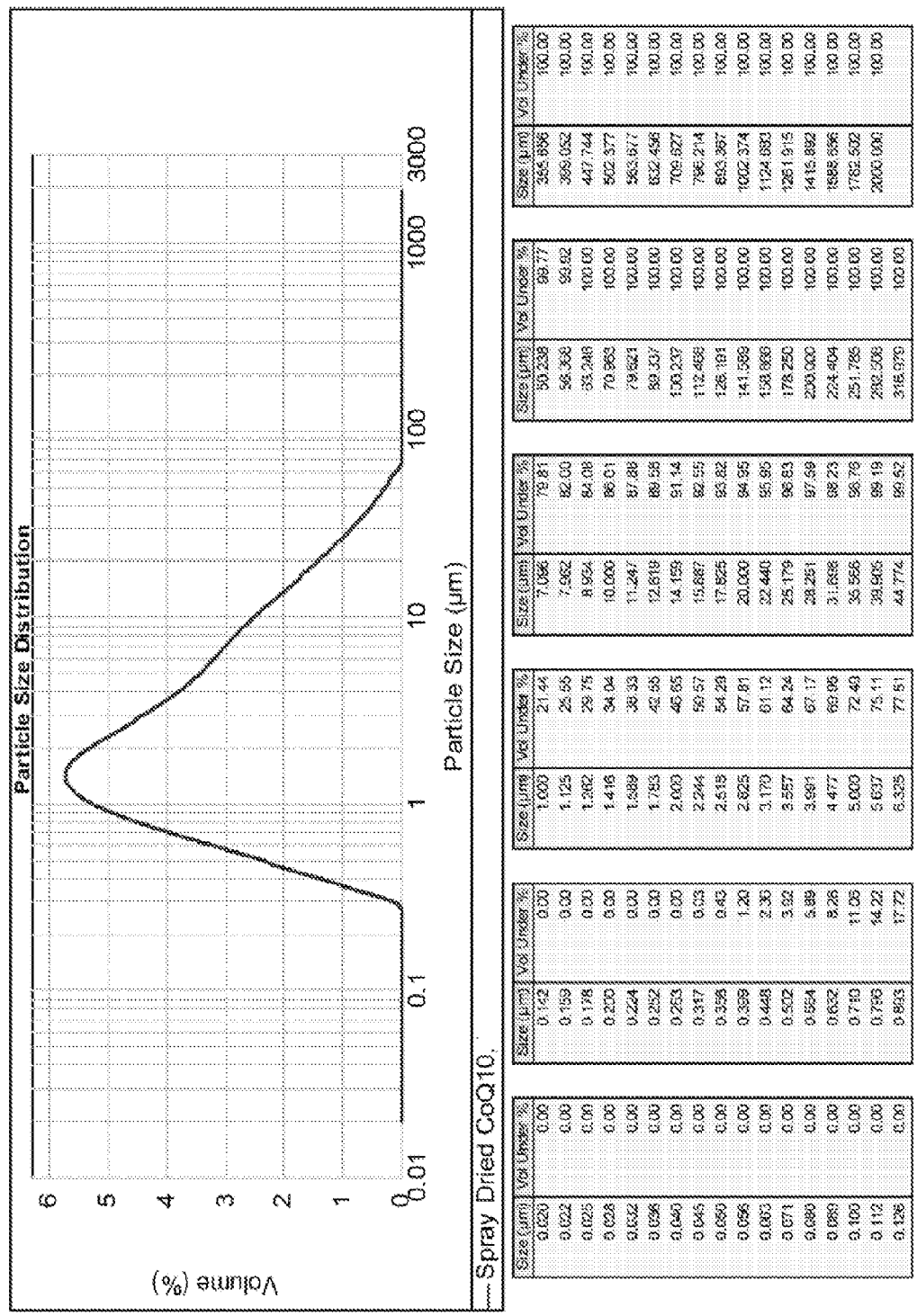
Figure 10I:
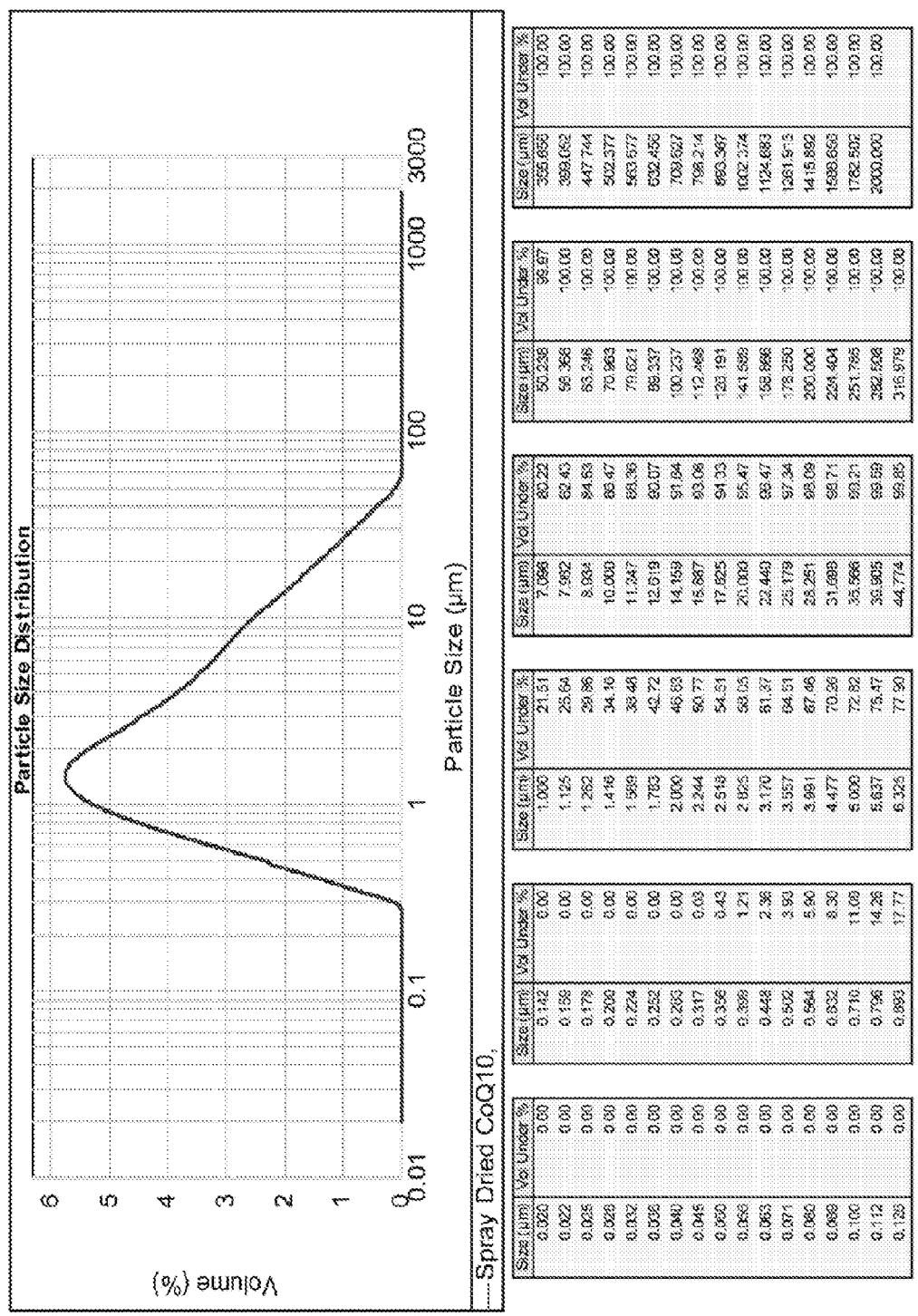
Figure 10J:
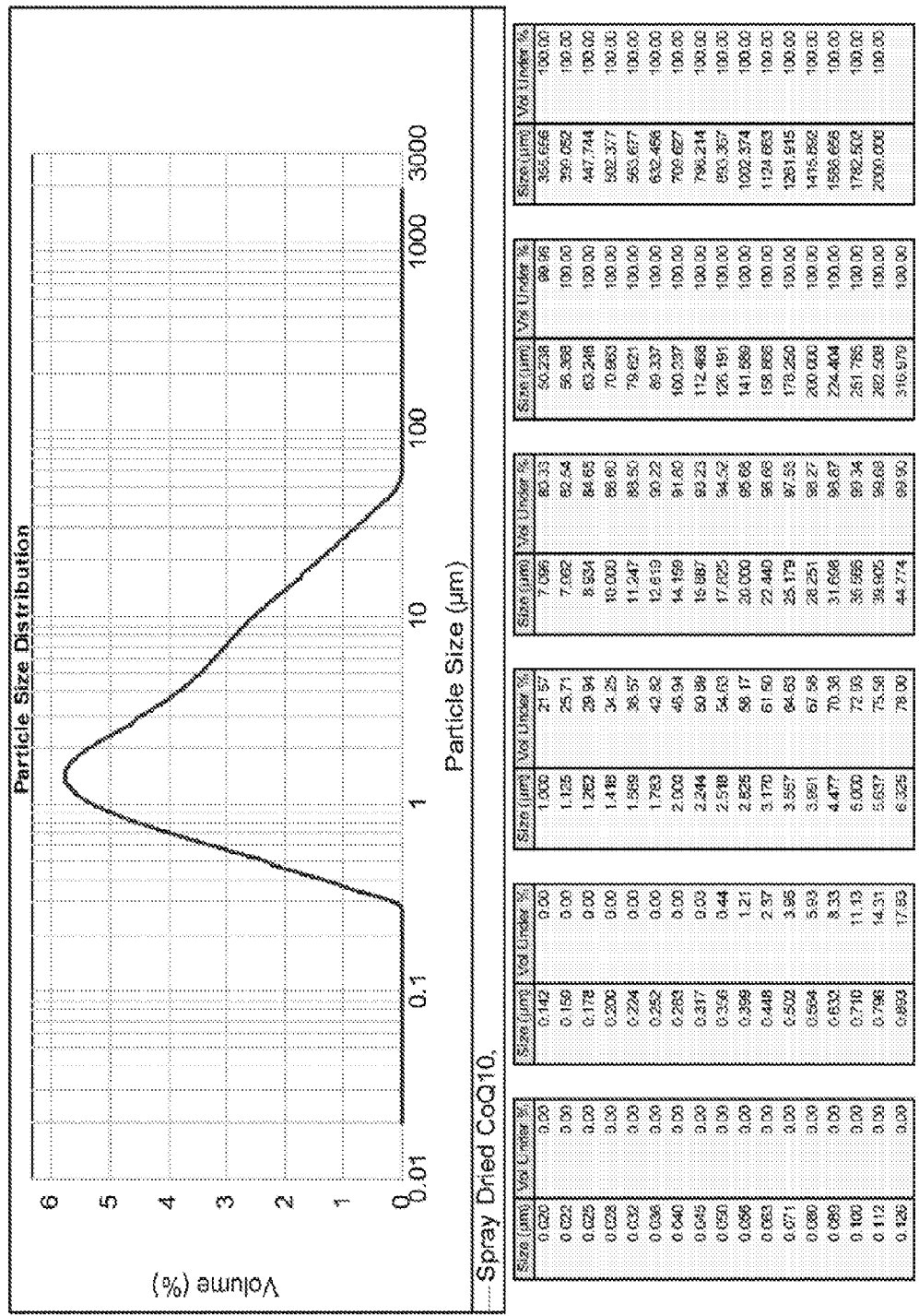
Figure 10K:
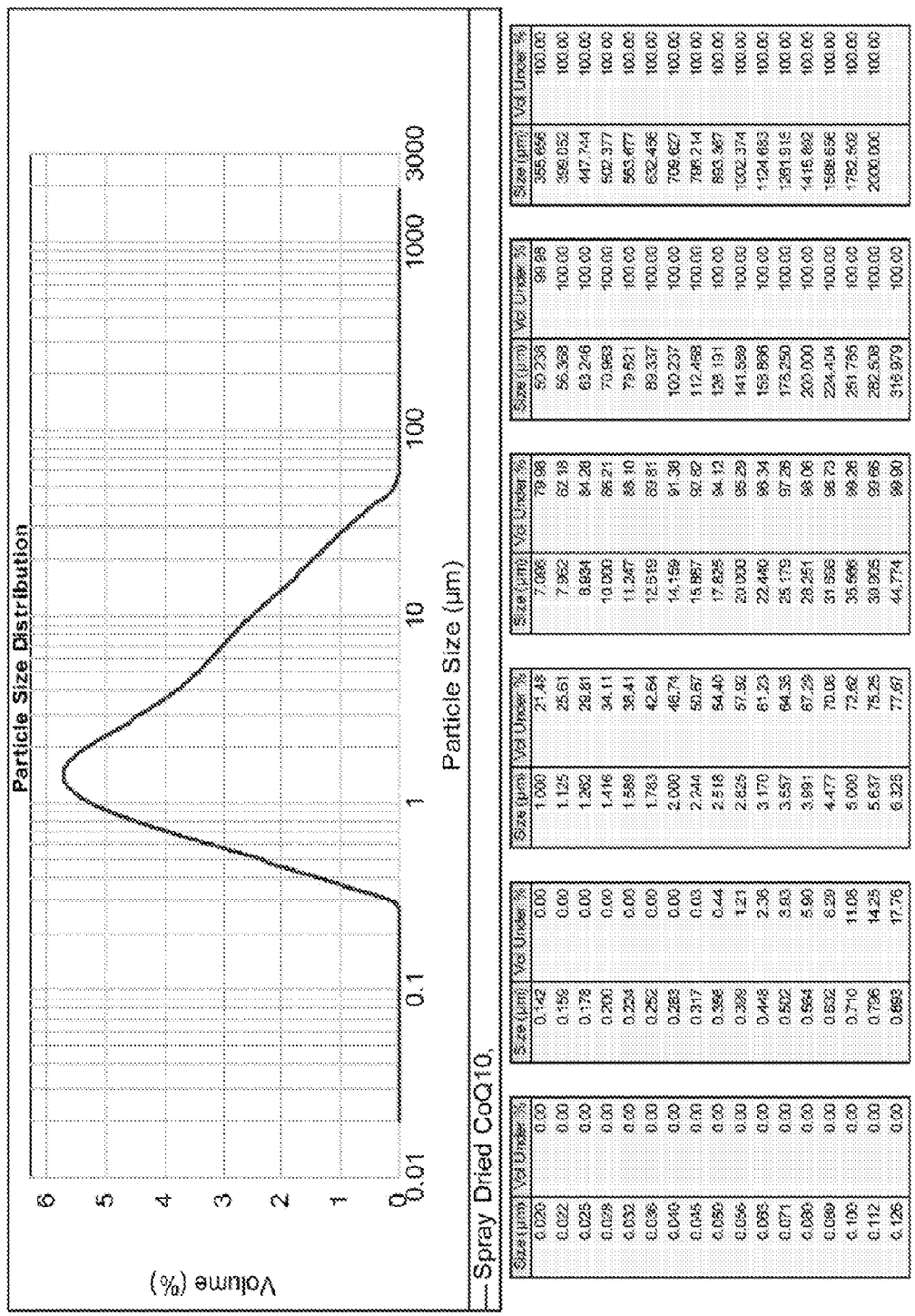

After 60 seconds of sonication, the resulting mixture was analyzed using laser diffraction to obtain a measurement of the CoQ10 particulate size characteristics. FIGS. 7A and 7B include the results of these analyses based on number % of particles. FIGS. 8A and 8B include the results of these analyses based on volume % of particles. The results of these measurements, taken independently for two samples of the spray dried powder, are summarized in Table 3 (FIGS. 7A and 7B) and Table 4 (FIGS. 8A and 8B) below.

TABLE 3

CoQ10 Particulate Size Distribution (Number Basis, 60 Seconds Sonication)

| | <0.40 µm (Number %) | <0.50 µm (Number %) | <0.80 µm (Number %) | <1.00 µm (Number %) | <2.00 µm (Number %) |
|---|---|---|---|---|---|
| A | 39.48 | 65.37 | 91.59 | 95.98 | 99.47 |
| B | 44.17 | 68.91 | 92.89 | 96.73 | 99.60 |
| Avg. | 41.83 | 67.14 | 92.24 | 96.36 | 99.54 |

TABLE 4

CoQ10 Particulate Size Distribution (Volume Basis, 60 Seconds Sonication)

| | <0.50 µm | <2.00 µm | <10.00 µm | <20.00 µm | <50.00 µm | <200.00 µm |
|---|---|---|---|---|---|---|
| A | 3.79 | 20.93 | 41.55 | 60.61 | 89.81 | 95.43 |
| B | 5.86 | 28.45 | 41.05 | 74.16 | 97.86 | 100 |
| Avg. | 4.825 | 24.69 | 41.3 | 67.385 | 93.835 | 97.715 |

The wide variance in the volume distribution table shown above indicates that sonicating the samples for 60 seconds was insufficient to achieve a uniform dispersion of the powder. As a result, subsequent samples were subjected to 120 seconds of sonication, which resulted in a significantly more uniform distribution of measured particle sizes.

The dispersion and sonication process was repeated for 11 additional samples, which resulted in multiple independent measurements of the particulate size data. The data for these analyses are included in FIGS. 9A-9K. These results are summarized in Table 5.

TABLE 5

CoQ10 Particulate Size Distribution (Number Basis, 120 Seconds Sonication)

| | <0.40 μm (Number %) | <0.50 μm (Number %) | <0.80 μm (Number %) | <1.00 μm (Number %) | <2.00 μm (Number %) |
|---|---|---|---|---|---|
| 1/A | 22.11% | 47.29% | 81.68% | 90.32% | 98.96% |
| 2/B | 22.11% | 47.24% | 81.63% | 90.19% | 99.30% |
| 3/C | 22.11% | 47.21% | 81.59% | 90.17% | 98.95% |
| 4/D | 22.12% | 47.22% | 81.59% | 90.17% | 98.95% |
| 5/E | 22.18% | 47.31% | 81.67% | 90.23% | 98.96% |
| 6/F | 22.18% | 47.27% | 81.62% | 90.19% | 98.96% |
| 7/G | 22.13% | 47.22% | 81.59% | 90.17% | 98.96% |
| 8/H | 22.24% | 47.32% | 81.63% | 90.20% | 98.96% |
| 9/I | 22.21% | 47.26% | 81.59% | 90.17% | 98.96% |
| 10/J | 22.28% | 47.34% | 81.64% | 90.20% | 98.96% |
| 11/K | 22.26% | 47.32% | 81.63% | 90.19% | 98.96% |
| Avg. | 22.18% | 47.27% | 81.62% | 90.20% | 98.99% |

As shown in the table above, greater than 90% by number basis of the CoQ10 microparticulates had a largest dimension of less than 1 micron. This represents a significant reduction in particulate size as compared to the commercially available CoQ10 starting material.

The particle size results were also analyzed on a volume basis. The results of these analyses are included in FIGS. 10A-10K and summarized in Table 6.

TABLE 6

CoQ10 Particulate Size Distribution (Volume Basis, 120 Seconds Sonication)

| | <0.50 μm | <1.00 μm | <2.00 μm | <5.00 μm | <10.00 μm | <20.00 μm |
|---|---|---|---|---|---|---|
| 1/A | 3.90% | 21.29% | 46.21% | 71.83% | 85.14% | 93.78% |
| 2/B | 3.87% | 21.15% | 46.00% | 71.55% | 84.90% | 93.55% |
| 3/C | 3.88% | 21.25% | 46.28% | 72.02% | 85.54% | 94.24% |
| 4/D | 3.89% | 21.29% | 46.37% | 72.21% | 85.73% | 94.61% |
| 5/E | 3.90% | 21.33% | 46.30% | 71.86% | 85.24% | 94.00% |
| 6/F | 3.90% | 21.45% | 46.66% | 72.50% | 86.05% | 94.90% |
| 7/G | 3.90% | 21.37% | 46.50% | 72.32% | 85.90% | 94.89% |
| 8/H | 3.92% | 21.44% | 46.65% | 74.49% | 86.01% | 94.95% |
| 9/I | 3.93% | 24.51% | 46.83% | 72.82% | 86.47% | 95.47% |
| 10/J | 3.95% | 21.57% | 46.94% | 72.93% | 86.60% | 95.66% |
| 11/K | 3.93% | 21.48% | 46.74% | 72.62% | 86.21% | 95.29% |
| Avg. | 3.91% | 21.65% | 46.50% | 72.47% | 85.80% | 94.67% |

On average, 50% by volume of the microparticulates had a largest dimension of less than 2.217 μm, with 90% by volume having a largest dimension of less than 13.248 μm. These results indicate a highly significant reduction in the presence of large CoQ10 particulates as compared to the starting material.

Example 8

Pharmacokinetic Data

The pharmacokinetics of CoQ10 absorption was studied using single and multiple oral 60 mg (2×30 mg) dose administration in 6 subjects per group. In a parallel study, one group received the test formulation of the present invention (prepared generally in accordance with the present invention, i.e., Examples 1 and 2), while a second group was given a reference product comprising crystalline CoQ10 (KANEKA Q10).

Blood was collected at 0, 1, 2, 4, 6, 8, 10, and 24 hours after subjects received a single dose of the test or reference product (RD). The subjects continued to orally ingest the test or reference product once per day for 6 additional days. Blood was collected 1 hour prior to dosing on Day 7 (167 hours) and at 8 hours post-dose (175 hours). The resulting plasma was analyzed for total, reduced and oxidized CoQ10 and cholesterol at each time point. Plasma CoQ10 concentrations were baseline corrected using the lowest initial value for each subject.

Figure 11:
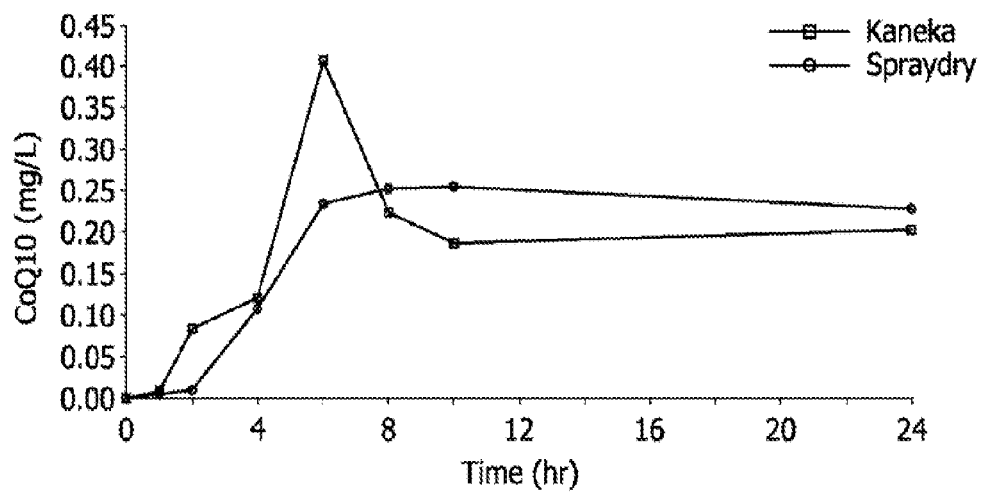
FIGS. 11-13 provide results of pharmacokinetic testing as described in Example 8.

Mean plasma CoQ10 concentration results are listed in Table 5 below, and are presented in graphical form in FIG. 11 (Spraydry refers to the test formulation prepared in accordance with the present invention; Kaneka refers to the reference formulation).

TABLE 7

Mean Plasma CoQ10 Concentration

| | Test Formulation | | Reference Formulation | |
|---|---|---|---|---|
| Time (h) | Mean | SD | Mean | SD |
| Day 1 | | | | |
| 0 | 0 | 0 | 0 | 0 |
| 1 | 0.0098 | 0.0195 | 0.0058 | 0.0143 |
| 2 | 0.0845 | 0.0920 | 0.0107 | 0.0166 |
| 4 | 0.1218 | 0.0862 | 0.1085 | 0.0934 |
| 6 | 0.4063 | 0.2940 | 0.2347 | 0.1769 |
| 8 | 0.2245 | 0.1688 | 0.2535 | 0.1780 |
| 10 | 0.1875 | 0.0622 | 0.2558 | 0.1354 |
| 24 | 0.2033 | 0.1118 | 0.2278 | 0.109 |
| Day 7 | | | | |
| 167 | 0.3373 | 0.1528 | 0.5612 | 0.1279 |
| 175 | 0.4493 | 0.1610 | 0.6413 | 0.2156 |

As summarized in Table 6 below, maximum plasma concentrations ($C_{max}$) were achieved faster (median $T_{max}$) for the test formulation (6 h) than for the reference formulation (10 h). Peak exposure ($C_{max}$) was higher for the test formulation (0.430 mg/L) than for the reference formulation (0.293 mg/L). Mean plasma CoQ10 concentrations were higher for the test formulation than the RD from 1 to 6 hours after a single dose, reaching a plateau from 8 to 24 hours post-dose.

TABLE 8

Results Overview

| $AUC_{0-24\,h}$ (mg · h/L) | $C_{max}$ (mg/L) | $T_{lag}$ (h) | $T_{max}$ (h) |
|---|---|---|---|
| Test Formulation | | | |
| 4.564 | 0.43 | 1 | 6 |
| Reference Formulation | | | |
| 4.857 | 0.293 | 2 | 10 |

Figure 12:
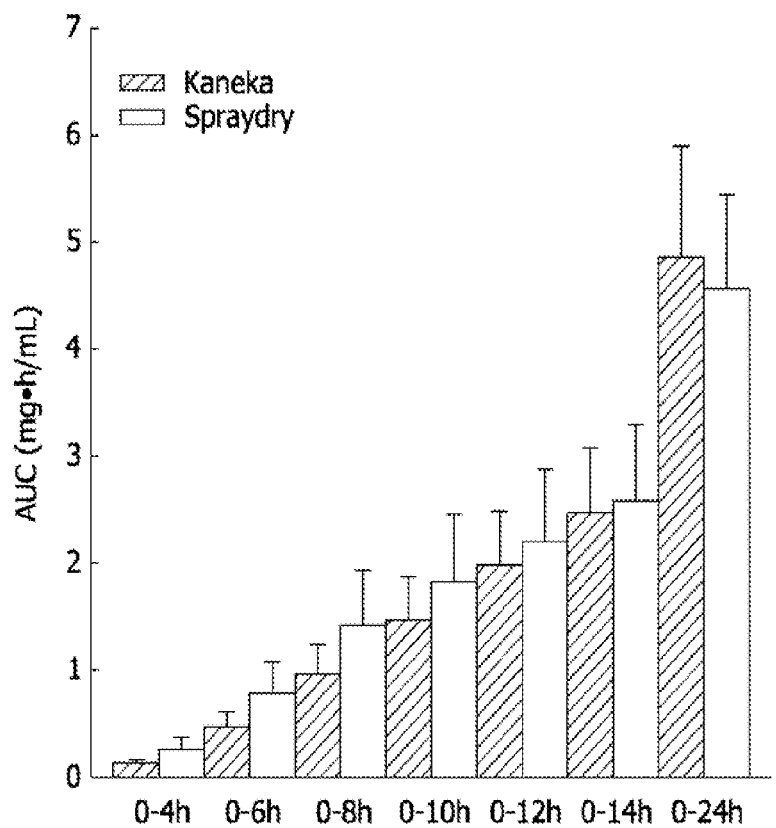

In addition, partial areas under the curve (pAUCs) were estimated using the trapezoidal rule from time 0 to each sample collection time point. The results of these calculations are summarized in Table 7 and shown in FIG. 12 (Spraydry refers to the test formulation prepared in accordance with the present invention; Kaneka refers to the reference formulation), with the mean values provided in mg·h/L and the standard deviations for each measurement provided in parenthesis.

TABLE 9

Summary of pAUC Calculations

| | Test | Reference |
|---|---|---|
| $AUC_{0-4\,h}$ | 0.258 | 0.130 |
| | (0.225) | (0.093) |
| $AUC_{0-6\,h}$ | 0.786 | 0.474 |
| | (0.579) | (0.341) |
| $AUC_{0-8\,h}$ | 1.417 | 0.962 |
| | (1.032) | (0.680) |
| $AUC_{0-10\,h}$ | 1.829 | 1.471 |
| | (1.250) | (0.979) |
| $AUC_{0-12\,h}$ | 2.206 | 1.979 |
| | (1.344) | (1.231) |
| $AUC_{0-14\,h}$ | 2.588 | 2.478 |
| | (1.423) | (1.475) |

Mean exposure (pAUC) to CoQ10 from the test formulation was consistently higher than for the reference formulation for all time intervals up to 14 hours post-dose. Total exposure over 24 hours ($AUC_{0-24h}$) was approximately the same for the test formulation and the reference formulation (4.56 mg·h/L vs. 4.86 mg·h/L).

Figure 13:
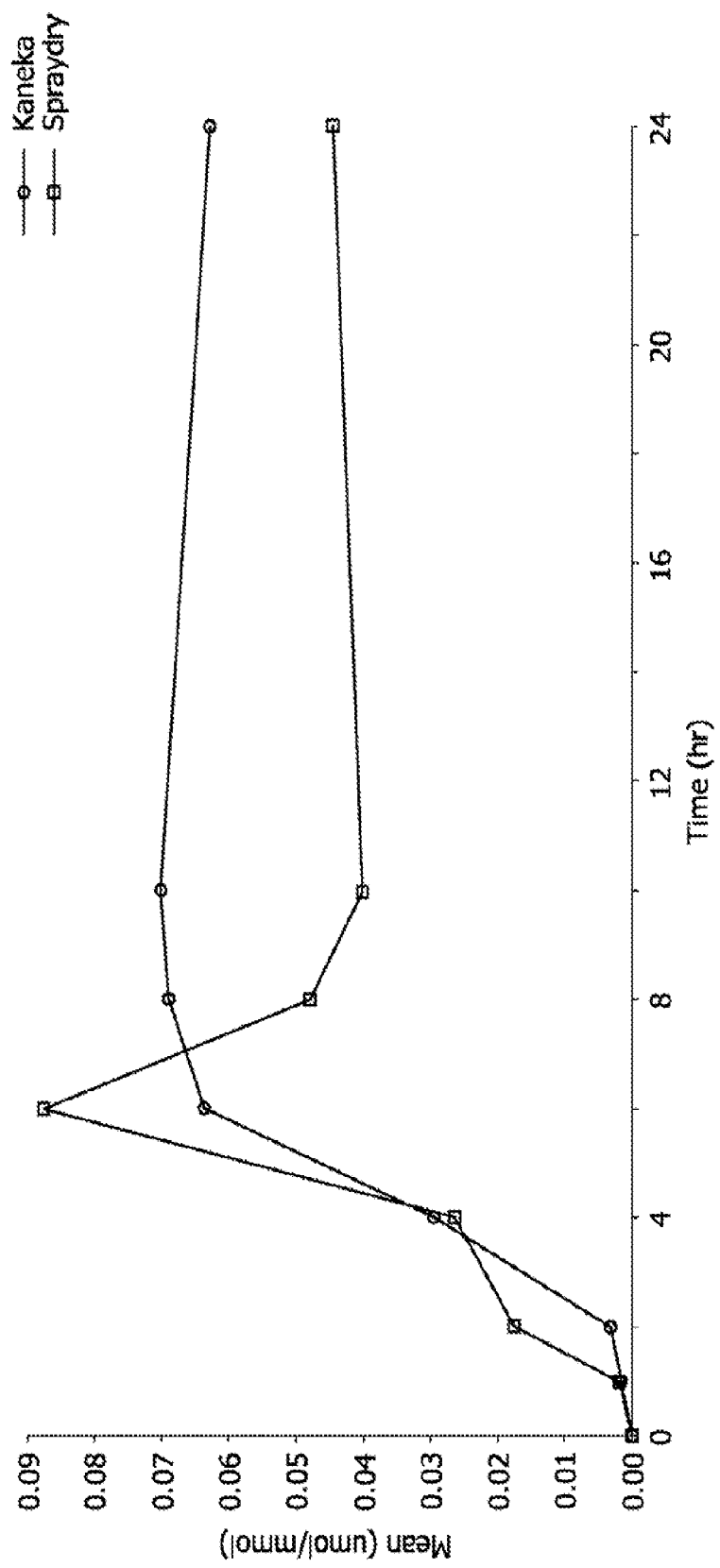

Additional calculations were performed to correct for differences in cholesterol levels between subjects in the Test group and the Reference group. The cholesterol-corrected data are presented in Tables 10 and 11 below, as well as in FIG. 13 (Spraydry refers to the test formulation prepared in accordance with the present invention; Kaneka refers to the reference formulation).

TABLE 10

Cholesterol-Corrected Results Overview

| $AUC_{0-24\,h}$ (mg · h/L) | $C_{max}$ (mg/L) | $T_{lag}$ (h) | $T_{max}$ (h) |
|---|---|---|---|
| Test Formulation | | | |
| 0.9839 | 0.0929 | 1 | 6 |
| Reference Formulation | | | |
| 1.332 | 0.0805 | 2 | 10 |

TABLE 11

Mean Cholesterol-Corrected Plasma CoQ10 Concentration

| | Test Formulation | | Reference Formulation | |
|---|---|---|---|---|
| Time (h) | Mean | SD | Mean | SD |
| Day 1 | | | | |
| 0 | 0 | 0 | 0 | 0 |
| 1 | 0.0020 | 0.0040 | 0.0017 | 0.0042 |
| 2 | 0.0175 | 0.0183 | 0.0033 | 0.0051 |
| 4 | 0.0263 | 0.0168 | 0.0293 | 0.0256 |
| 6 | 0.0876 | 0.0647 | 0.0638 | 0.0441 |
| 8 | 0.0479 | 0.0416 | 0.0690 | 0.0464 |
| 10 | 0.0400 | 0.0180 | 0.0702 | 0.0395 |
| 24 | 0.0446 | 0.0332 | 0.0628 | 0.0346 |
| Day 7 | | | | |
| 167 | 0.0748 | 0.0444 | 0.1531 | 0.0600 |
| 175 | 0.0979 | 0.0445 | 0.1691 | 0.0742 |

Example 9

Comparison Testing

The test formulation studied in Example 9 above was also compared to other products on the market, based on published data from a group at DSM R&D, based in Kaiseraugst, Switzerland. See Ullmann U, Metzner J, Schulz C, Perkins J, Leuenberger B., A new Coenzyme Q10 tablet-grade formulation (all-Q) is bioequivalent to Q-Gel and both have better bioavailability properties than Q-SorB, Journal of Medicinal Food (2005) 8(3): 397-399.

The comparative data presented in Ullman et al. are reproduced in Table 12 below.

TABLE 12

Comparative Testing Data

| | CoQ10 Concentration in Plasma (µg/ml) | | |
|---|---|---|---|
| Time (hours) | Q-Gel | DSM | Nature's Bounty |
| 0 | 0 | 0 | 0 |
| 0.5 | 0.00869 | 0.01304 | 0.01304 |
| 1 | 0.02174 | 0.01739 | 0.01739 |
| 1.5 | 0.02609 | 0.02174 | 0.02174 |
| 2 | 0.03043 | 0.02609 | 0.02609 |
| 3 | 0.10435 | 0.14783 | 0.03043 |
| 4 | 0.15217 | 0.20869 | 0.03478 |
| 5 | 0.36956 | 0.34783 | 0.13913 |
| 6 | 0.66957 | 0.53913 | 0.26521 |
| 7 | 0.74348 | 0.68261 | 0.46087 |
| 8 | 0.5913 | 0.54783 | 0.40869 |
| 10 | 0.47826 | 0.44348 | 0.30435 |
| 12 | 0.3913 | 0.35652 | 0.25217 |
| 14 | 0.31739 | 0.29565 | 0.20869 |
| 24 | 0.27826 | 0.25217 | 0.22609 |

The data reported in the Ullmann et al. paper was based a CoQ10 oral dose of 120 mg. Because the dose administered in the study of Example 9 was 60 mg, plasma concentrations from the publication were dose-adjusted to 60 mg. This represents a good assumption, as CoQ10 exhibits linear kinetics in this dosing range. It is only at dose levels well above 300 mg that there CoQ10 begins to exhibit reduced percent absorption with increased dosage.

The dose-adjusted data are presented in Table 13 below.

TABLE 13

Comparative Testing Data (Dose-Adjusted)

| | CoQ10 Concentration in Plasma (µg/ml) | | |
|---|---|---|---|
| Time (hours) | Q-Gel | DSM | Nature's Bounty |
| 0 | 0 | 0 | 0 |
| 0.5 | 0.004345 | 0.00652 | 0.00652 |
| 1 | 0.01087 | 0.008695 | 0.008695 |
| 1.5 | 0.013045 | 0.01087 | 0.01087 |
| 2 | 0.015215 | 0.013045 | 0.013045 |
| 3 | 0.052175 | 0.073915 | 0.015215 |
| 4 | 0.076085 | 0.104345 | 0.01739 |
| 5 | 0.18478 | 0.173915 | 0.069565 |
| 6 | 0.334785 | 0.269565 | 0.132605 |
| 7 | 0.37174 | 0.341305 | 0.230435 |
| 8 | 0.29565 | 0.273915 | 0.204345 |
| 10 | 0.23913 | 0.22174 | 0.152175 |
| 12 | 0.19565 | 0.17826 | 0.126085 |
| 14 | 0.158695 | 0.147825 | 0.104345 |
| 24 | 0.13913 | 0.126085 | 0.113045 |

Figure 14:
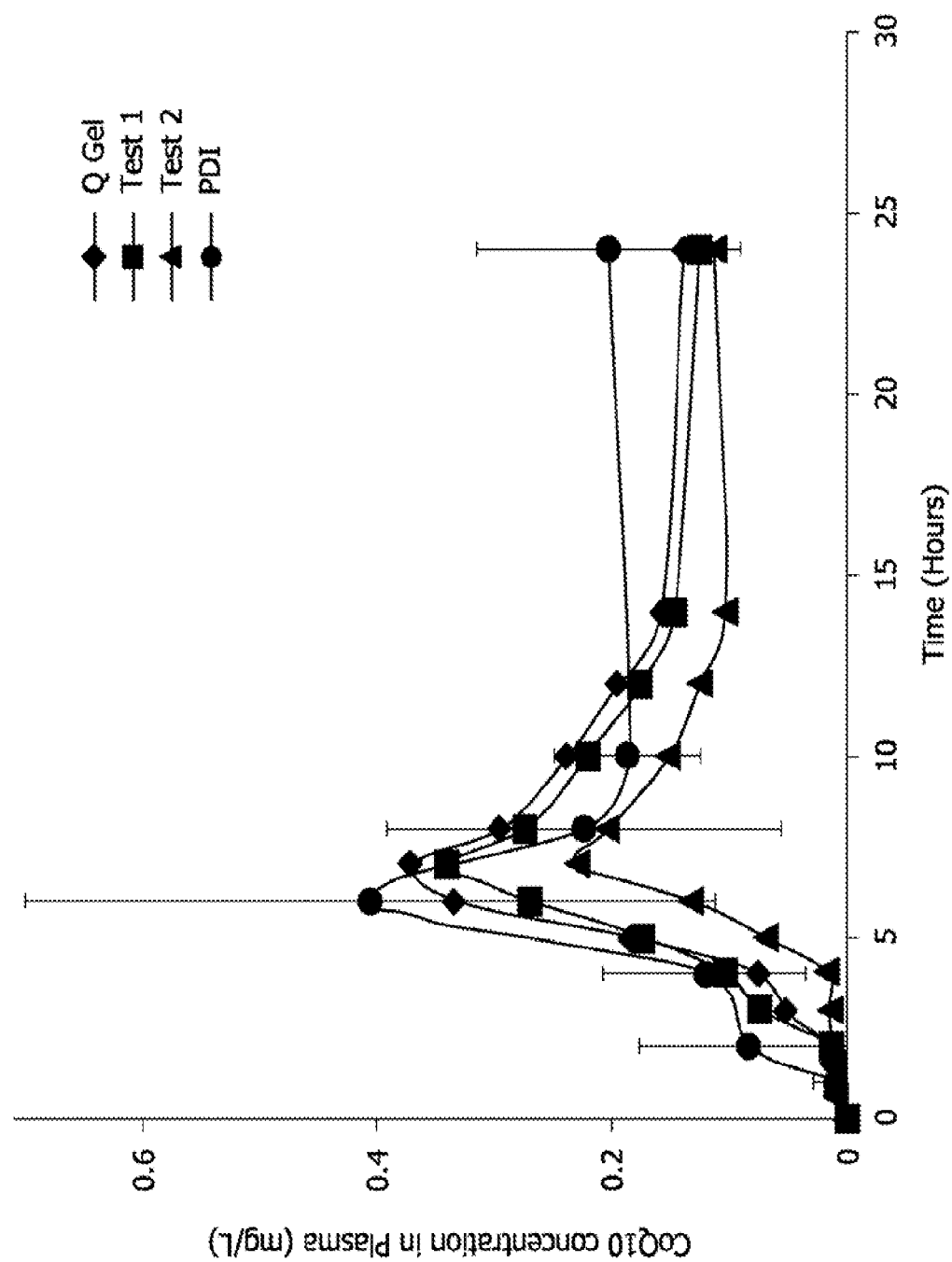
FIG. 14 provides the results of formulation testing as described in Example 9.

The dose-adjusted data from Table 13 are represented in graphical form in FIG. 14. For comparative purposes, FIG.

14 also includes a representation of the test formulation data collected in Example 9. As shown in FIG. 14, Test 1 refers to the Q-SORB nano-beadlet product available from DSM; Test 2 refers to the Q-SORB product from NATURE'S BOUNTY; PDI refers to the composition prepared in accordance with the present invention.

The data indicate that the test formulation is considerably better absorbed, with a higher $C_{max}$ and a much larger area under the curve than the Nature's Bounty product. More specifically, the test formulation has an $AUC_{0-14h}$ of 2.588 mg·h/L vs. 1.78 mg·h/L for Nature's Bounty, 2.30 mg·h/L for the DSM product and 2.49 mg·h/L for the Tishcon Q-gel. One item of particular note is that the test formulation maintains blood levels longer at an elevated level, so long term therapy should be more beneficial for patients using the test formulation in view of its extended release profile.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A method for preparing a particulate composition comprising coenzyme Q10, the method comprising:
   combining an organic phase and an aqueous phase, thereby forming an oil-in-water emulsion having the organic phase dispersed throughout the aqueous phase; and
   drying the emulsion, thereby forming a composition comprising solid particles comprising coenzyme Q10, wherein:
   the organic phase comprises coenzyme Q10, a solvent, and a first surfactant, the first surfactant comprising tocopherol polyethylene glycol succinate or a polyoxyglyceride selected from the group consisting of lauroyl macroglycerides, stearoyl macroglycerides, and combinations thereof;
   the aqueous phase comprises water, starch, and an organic acid selected from the group consisting of citric acid, succinic acid, ascorbic acid and mixtures thereof;
   the organic phase and/or aqueous phase further comprises a second surfactant comprising phosphatidyl choline; and
   wherein the solid particles comprising coenzyme Q10 have a particle size distribution such that at least about 90% by weight of the particulates have a particle size of from about 1 to about 4 μm.

2. The method of claim 1 wherein the solvent comprises an organic solvent selected from the group consisting of hexanol, ethanol, butanol, heptanol, 2-methyl-1-pentanol, methyl ethyl ketone, acetone, propylene glycol, ethyl acetate, and mixtures thereof.

3. The method of claim 1 wherein the first surfactant comprises tocopherol polyethylene glycol succinate.

4. The method of claim 1 wherein the first surfactant comprises a polyoxyglyceride selected from the group consisting of lauroyl macroglycerides, stearoyl macroglycerides, and combinations thereof.

5. The method of claim 1 wherein the organic phase comprises the second surfactant comprising phosphatidyl choline.

6. The method of claim 1 wherein the aqueous phase comprises the second surfactant comprising phosphatidyl choline.

7. The method of claim 1 wherein the aqueous phase further comprises a base selected from the group consisting of sodium bicarbonate, sodium carbonate, sodium hydroxide, and mixtures thereof.

8. The method of claim 1 wherein the emulsion comprises discrete microdroplets of coenzyme Q10 associated with at least one surfactant.

9. The method of claim 1 wherein the solid particles are in the form of colloidal particles comprising discrete microparticulates dispersed throughout a solid matrix, wherein the microparticulates comprise coenzyme Q10 associated with at least one surfactant.

10. The method of claim 1, wherein:
    the organic phase comprises an organic solvent selected from the group consisting of hexanol, ethanol, butanol, heptanol, 2-methyl-1-pentanol, methyl ethyl ketone, acetone, propylene glycol, ethyl acetate, and mixtures thereof;
    the first surfactant comprises tocopherol polyethylene glycol succinate; and
    the aqueous phase comprises a chemically modified starch.

11. The method of claim 10, wherein:
    the organic phase comprises hexanol as a solvent.

12. The method of claim 1, wherein:
    the organic phase comprises an organic solvent selected from the group consisting of hexanol, ethanol, butanol, heptanol, 2-methyl-1-pentanol, methyl ethyl ketone, acetone, propylene glycol, ethyl acetate, and mixtures thereof;
    the first surfactant comprises a polyoxyglyceride selected from the group consisting of lauroyl macroglycerides, stearoyl macroglycerides, and combinations thereof; and
    the aqueous phase comprises a chemically modified starch.

13. The method of claim 12, wherein:
    the organic phase comprises hexanol as a solvent.

14. The method of claim 1, wherein the first surfactant comprises tocopherol polyethylene glycol succinate and the aqueous phase comprises the second surfactant.

15. The method of claim 1, wherein the first surfactant comprises a polyoxyglyceride selected from the group consisting of lauroyl macroglycerides, stearoyl macroglycerides, and combinations thereof and the aqueous phase comprises the second surfactant.

* * * * *